US009586985B2

(12) United States Patent
Compton et al.

(10) Patent No.: US 9,586,985 B2
(45) Date of Patent: Mar. 7, 2017

(54) ORGANIC COMPOUNDS AS PROANTIGENS FOR NATURAL KILLER T CELLS

(71) Applicant: Callaghan Innovation Research Limited, Lower Hutt (NZ)

(72) Inventors: Benjamin Jason Compton, Lower Hutt (NZ); Colin Malcolm Hayman, Lower Hutt (NZ); Ian Francis Hermans, Wellington (NZ); David Samuel Larsen, Dunedin (NZ); Gavin Frank Painter, Lower Hutt (NZ); Regan J. Anderson, Lower Hutt (NZ)

(73) Assignee: VICTORIA LINK LIMITED, Wellington (NZ)

( * ) Notice: Subject to any disclaimer, the term of this patent is extended or adjusted under 35 U.S.C. 154(b) by 90 days.

(21) Appl. No.: 14/417,487

(22) PCT Filed: Jul. 26, 2013

(86) PCT No.: PCT/NZ2013/000133
§ 371 (c)(1),
(2) Date: Jan. 26, 2015

(87) PCT Pub. No.: WO2014/017928
PCT Pub. Date: Jan. 30, 2014

(65) Prior Publication Data
US 2015/0191503 A1    Jul. 9, 2015

(30) Foreign Application Priority Data
Jul. 26, 2012   (NZ) ........................... 601473

(51) Int. Cl.
| C07H 15/04 | (2006.01) |
| A61K 39/39 | (2006.01) |
| C07H 15/06 | (2006.01) |
| A61K 39/00 | (2006.01) |

(52) U.S. Cl.
CPC ............. *C07H 15/04* (2013.01); *A61K 39/39* (2013.01); *C07H 15/06* (2013.01); A61K 2039/55511 (2013.01)

(58) Field of Classification Search
CPC .................. C07H 15/06; C07H 15/04; A61K 2039/55511; A61K 39/39
USPC ................... 536/17.1, 17.8, 17.9; 424/283.1
See application file for complete search history.

(56) References Cited

U.S. PATENT DOCUMENTS 6,635,622 B2 * 10/2003 Tomiyama ............... C07H 7/02
514/23
2006/0024691 A1    2/2006 Benz

FOREIGN PATENT DOCUMENTS

WO   WO 2008/128062    * 10/2008   ............. C07H 15/10
WO   WO-2008128062 A1    10/2008

OTHER PUBLICATIONS

International Search Report of PCT/NZ2013/000133, dated Sep. 11, 2013.
Alexander et al., "(Acyloxy)alkyl Carbamates as Novel Bioreversible Prodrugs for Amines: Increased Permeation through Biological Membranes," *Journal of Medicinal Chemistry* 31:318-322, 1998.
Alexander et al., "Investigation of (Oxodioxolenyl)methyl Carbamates as Nonchiral Bioreversible Prodrug Moieties for Chiral Amines," *Journal of Medicinal Chemistry* 39:480-486, 1996.
Amsberry et al., "Amine Prodrugs Which Utilize Hydroxy Amide Lactonization. I. A Potential Redox-Sensitive Amide Prodrug," *Pharmaceutical Research* 8(3):323-330, 1991.
Amsberry et al., "Amine Prodrugs Which Utilize Hydroxy Amide Lactonization. II. A Potential Esterase-Sensitive Amide Prodrug," *Pharmaceutical Research* 8(4):455-461, 1991.
Baadsgaard et al., "201. Zure Kenntnis der komplexen Wolframcyanide $K_4[W(CN)_a]$, 2 $H_2O$ and $K_3[W(CN)_a]$, $H_2O$," *Helvetica Chimica Acta* 38(7):1669-1679, 1955, with English Abstract, 12 pages.
Badovinac et al., "$CD8^+$ T cell contraction is controlled by early inflammation," *Nature Immunology* 5(8):809-817, Aug. 2004.
Baek et al., "The 3-Deoxy Analogue of α-GalCer: Disclosing the Role of the 4-Hydroxyl Group for CD1d-Mediated NKT Cell Activation," *ACS Medicinal Chemistry Letters* 2:544-548, 2011.
Banchet-Cadeddu et al., "The stimulating adventure of KRN 7000," *Organic & Biomolecular Chemistry* 9:3080-3104, 2011.
Bendelac et al., "The Biology of NKT Cells," *Annual Review of Immunology* 25:297-336, 2007.
Brossart et al., "Identification of HLA-A2-Restricted T-Cell Epitopes Derived From the MUC1 Tumor Antigen for Broadly Applicable Vaccine Therapies," *Blood* 93(12):4309-4317, Jun. 1999.
Butler et al., "Reaction of Fatty Acids with Amines. Part 2. Sequential Thermal Reactions of Stearic (Octadecanoic) Acid with Some 1,2- and 1,3-Amino-alcohols and Bis-amines," *Journal of the Chemical Society, Perkin Transactions 1*:373-377, 1978.
Carpino et al., "Reductive Lactonization of Strategically Methylated Quinone Propionic Acid Esters and Amides," *Journal of Organic Chemistry* 54(14):3303-3310, 1989.
Chen et al., "Efficient Synthesis of α-C-Galactosyl Ceramide Immunostimulants: Use of Ethylene-Promoted Olefin Cross-Metathesis," *Organic Letters* 6(22):4077-4080, 2004.
Davidson et al., "Effect of TA-CIN (HPV 16 L2E6E7) booster immunisation in vulval intraepithelial neoplasia patients previously vaccinated with TA-HPV (vaccinia virus encoding HPV 16/18 E6E7)," *Vaccine* 22:2722-2729, 2004.
Deng et al., "Impact of sugar stereochemistry on natural killer T cell stimulation by bacterial glycolipids," *Organic & Biomolecular Chemistry* 9:7659-7662, 2011.

(Continued)

*Primary Examiner* — Ganapathy Krishnan
(74) *Attorney, Agent, or Firm* — Seed IP Law Group LLP

(57) ABSTRACT

This invention relates to sphingoglycolipid analogs, compositions comprising these compounds, processes for preparing the compounds, and methods of treating or preventing diseases or conditions using the compounds, such as diseases or conditions relating to infection, atopic disorders, autoimmune disease, diabetes or cancer.

20 Claims, 10 Drawing Sheets

(56) References Cited

OTHER PUBLICATIONS

Dere et al., "The First Synthesis of a Thioglycoside Analogue of the Immunostimulant KRN7000," *Organic Letters* 10(20):4641-4644, 2008.
Drefahl et al., "Stereoselektive Darstellung and konfigurative Zuordnung der diastereomeren DL-3-Amino-1.2-diphenyl-propanole-(1) (zum Mechanismus der Ringschlußreaktion von Aminoalkoholen mit Benzimidsäureester)," *Chemische Berichte* 94(6):1641-1656, 1961, with English Abstract, 17 pages.
Du et al., "Efficient, one-pot syntheses of biologically active α-linked glycolipids," *Chemical Communications* 23:2336-2338, 2007.
Ebensen et al., "A Pegylated Derivative of α-Galactosylceramide Exhibits Improved Biological Properties," *Journal of Immunology* 179:2065-2073, 2007, 11 pages.
Fujii et al., "Activation of Natural Killer T Cells by a α-Galactosylceramide Rapidly Induces the Full Maturation of Dendritic Cells In Vivo and Thereby Acts as an Adjuvant for Combined CD4 and CD8 T Cell Immunity to a Coadministered Protein," *The Journal of Experimental Medicine* 198(2):267-279, Jul. 2003.
Fujii et al., "Prolonged IFN-γ-producing NKT response induced with α-galactosylceramide-loaded DCs," *Nature Immunology* 3(9):867-874, Sep. 2002.
Gangwar et al., "Synthesis of a Novel Esterase-Sensitive Cyclic Prodrug of a Hexapeptide Using an (Acyloxy)alkoxy Promoiety," *Journal of Organic Chemistry* 62:1356-1362, 1997.
Greenwald et al., "Drug Delivery Systems Based on Trimethyl Lock Lactonization: Poly(ethylene glycol) Prodrugs of Amino-Containing Compounds," *Journal of Medicinal Chemistry* 43:475-487, 2000.
Greenwald et al., "Drug Delivery Systems Employing 1,4- or 1,6-Elimination: Poly(ethylene glycol) Prodrugs of Amine-Containing Compounds," *Journal of Medicinal Chemistry* 42:3657-3667, 1999.
Gryko et al., "Thiol-Derivatized Porphyrins for Attachment to Electroactive Surfaces," *Journal of Organic Chemistry* 64:8635-8647, 1999.
Hermans et al., "NKT Cells Enhance $CD4^+$ and $CD8^+$ T Cell Responses to Soluble Antigen In Vivo through Direct Interaction with Dendritic Cells," *The Journal of Immunology* 171:5140-5147, 2003, 9 pages.
Hillery et al., "Stereopopulation Control. 9. Rate and Equilibrium Enhancement in the Lactonization of (o-Hydroxyphenyl)acetic Acids," *Journal of Organic Chemistry* 48:3465-3471, 1983.
Hong et al., "The natural killer T-cell ligand α-galactosylceramide prevents autoimmune diabetes in non-obese diabetic mice," *Nature Medicine* 7(9):1052-1056, Sep. 2001.
Howell et al., "Approaches to the preparation of sphinganines," *Tetrahedron* 60:11327-11347, 2004.
Iha et al., "Complex, Degradable Polyester Materials via Ketoxime Ether-Based Functionalization: Amphiphilic, Multifunctional Graft Copolymers and Their Resulting Solution-State Aggregates," *Journal of Polymer Science: Part A: Polymer Chemistry* 48:3553-3563, 2010.
Ingram et al., "Introduction of 2,2,2-Trichloroethyl-Protected Sulfates into Monosaccharides with a Sulfuryl Imidazolium Salt and Application to the Synthesis of Sulfated Carbohydrates," *Angewandte Chemie International Edition* 45:3503-3506, 2006.
Johansen et al., "Synthesis of Carbasugars from Aldonolactones: Ritter-Type Epoxide Opening in the Synthesis of Polyhydroxylated Aminocyclopentanes," *Synthesis* 1:171-177, 1999.
Kawano et al., "CD1d-Restricted and TCR-Mediated Activation of $V_α14$ NKT Cells by Glycosylceramides," *Science* 278:1626-1629, Nov. 1997.
Kinjo et al., "Invariant natural killer T cells recognize glycolipids from pathogenic Gram-positive bacteria," *Nature Immunology* 12(10):966-975, Oct. 2011.
Lee et al., "Novel synthesis of α-galactosyl-ceramides and confirmation of their powerful NKT cell agonist activity," *Carbohydrate Research* 341:2785-2798, 2006.
Levy et al., "A melanoma multiepitope polypeptide induces specific $CD8^+$ T-cell response,", *Cellular Immunology* 250:24-30, 2008.
Li et al., "Identification of a WT1 protein-derived peptide, $WT1_{187}$, as a HLA-A*0206-restricted, WT1-specific CTL epitope,"*Microbiology & Immunology* 52:551-558, 2008.
Li et al., "The Vα14 invariant natural killer T cell TCR forces microbial glycolipids and CD1d into a conserved binding mode," *The Journal of Experimental Medicine* 207(11):2383-2393, Oct. 2010.
Liao et al., "Substituted Coumarins as Esterase-Sensitive Prodrug Moieties with Improved Release Rates," *Bioorganic & Medicinal Chemistry Letters* 9:1795-1800, 1999.
Lin et al., "A Continuous Procedure for Preparation of *para* Functionalized Aromatic Thiols using Newman-Kwart Chemistry," *Organic Preparations and Procedures International* 32(6):547-555, 2000.
Lin et al., "Mono and Bis Double Ester Prodrugs of Novel Aminomethyl-THF 1β-Methylcarbapenems," *Bioorganic & Medicinal Chemistry Letters* 7(14):1811-1816, 1997.
Lu et al., "Induction of the Epstein-Barr Virus Latent Membrane Protein 2 Antigen-specific Cytotoxic T Lymphocytes Using Human Leukocyte Antigen Tetramer-based Artificial Antigen-presenting Cells," *Acta Biochimic et Biophysica Sinica* 38(3):157-163, 2006.
Lu et al., "Synthesis and Evaluation of an α-C-Galactosylceramide Analogue that Induces Th1-biased Responses in Human Natural Killer T Cells," *ChemBioChem* 7:1750-1756, 2006.
Luo et al., "A Concise Synthesis of Tetrahydroxy-LCB, α-Galactosyl Ceramide, and 1,4-Dideoxy-1,4-imino-$_L$-ribitol via $_D$-Allosamines as Key Building Blocks," *The Journal of Organic Chemistry* 71:1226-1229, 2006.
Matto et al., "A General and Stereoselective Route to α- or β-Galactosphingolipids via a Common Four-Carbon Building Block," *The Journal of Organic Chemistry* 72:7757-7760, 2007.
Morita et al., "Structure-Activity Relationship of α-Galactosylceramides against B16-Bearing Mice," *The Journal of Medicinal Chemistry* 38:2176-2187, 1995.
Murata et al., "Total Synthesis of an Immunosuppressive Glycolipid, (2S, 3S, 4R)-1-O-(α-D-Galactosyl)-2-tetracosanoylamino-1,3,4-nonanetriol," *The Journal of Organic Chemistry* 70:2398-2401, 2005.
Nicolaou et al., "Phosphate Prodrugs for Amines Utilizing a Fast Intramolecular Hydroxy Amide Lactonization," *The Journal of Organic Chemistry* 61:8636-8641, 1996.
O'Reilly et al., "Synthesis of α-S-Glycosphingolipids Based on Uronic Acids," *Organic Letters* 13(19):5168-5171, 2011.
Parekh et al., "Glycolipid antigen induces long-term natural killer T cell anergy in mice," *The Journal of Clinical Investigation* 115(9):2572-2583, Sep. 2005.
Plettenburg et al., "Synthesis of α-Galactosyl Ceramide, a Potent Immunostimulatory Agent," *The Journal of Organic Chemistry* 67:4559-4564, 2002.
Pu et al., "*C*-Galactosylceramide diastereomers via Sharpless asymmetric epoxidation chemistry," *Tetrahedron* 64:8618-8629, 2008.
Raju et al., "Synthesis and evaluation of 3"- and 4"-deoxy and -fluoro analogs of the immunostimulatory glycolipid, KRN7000," *Bioorganic & Medicinal Chemistry Letters* 19:4122-4125, 2009.
Sakurai et al., "Design and synthesis of functionalized trisaccharides as p53-peptide mimics," *Tetrahedron Letters* 51:3724-3727, 2010.
Schneider et al., "Ritter-Reaction on Steroids: Ring Expansion of Steroid Oxethans into Dihydrooxazines," *Tetrahedron* 41(16):3377-3386, 1985.
Secrist III et al., "Amine Hydrochlorides by Reduction in the Presence of Chloroform," *Journal of Organic Chemistry* 37(2):335-336, 1972.
Silk et al., "Utilizing the adjuvant properties of CD1d-dependent NK T cells in T cell-mediated immunotherapy," *Journal of Clinical Investigation* 114(12):1800-1811, Dec. 2004.

(56) References Cited

OTHER PUBLICATIONS

Sullivan et al., "Mechanisms for Glycolipid Antigen-Driven Cytokine Polarization by V α14i NKT Cells," *The Journal of Immunology* 184:141-153, 2010.

Sun et al., "A general synthesis of dioxolenone prodrug moieties," *Tetrahedron Letters* 43:1161-1164, 2002.

Tashiro et al., "RCAI-17, 22, 24-26, 29, 31, 34-36, 38-40, and 88, the analogs of KRN7000 with a sulfonamide linkage: Their synthesis and bioactivity for mouse natural killer T cells to produce Th2-biased cytokines," *Bioorganic & Medicinal Chemistry* 16:8896-8906, 2008.

Taylor et al., "Rapid and efficient chemoselective and multiple sulfations of phenols using sulfuryl imidazolium salts," *Tetrahedron Letters* 52:3353-3357, 2011.

Trappeniers et al., "Synthesis and in vitro Evaluation of α-GalCer Epimers," *ChemMedChem* 3:1061-1070, 2008.

Tupin et al., "CD1d-dependent Activation of NKT Cells Aggravates Atherosclerosis," *The Journal of Experimental Medicine* 199(3):417-422, Jan. 2004.

Turner et al., "Synthesis of Two Metabolites of (+)-Propoxyphene," *Journal of Medicinal Chemistry* 20(8):1065-1068, 1977.

Uchimura et al., "Immunostimulatory Activities of Monoglycosylated α-D-Pyranosylceramides," *Bioorganic & Medicinal Chemistry* 5(12):2245-2249, 1997.

Veerapen et al., "Synthesis and biological activity of α-galactosyl ceramide KRN7000 and galactosyl (α1→2) galactosyl ceramide," *Bioorganic & Medicinal Chemistry Letters* 19:4288-4291, 2009.

Wipf et al., "Expedient Synthesis of the α-C-Glycoside Analogue of the Immunostimulant Galactosylceramide (KRN7000)," *Organic Letters* 8(15):3375-3378, 2006.

Wu et al., "Avidity of CD1d-ligand-receptor ternary complex contributes to T-helper 1 (TH1) polarization and anticancer efficacy," *Proceedings of the National Academy of Sciences* 108(42):17275-17280, Oct. 2011.

Zeng et al., "Activation of natural killer T cells in NZB/W mice induces Th1-type immune responses exacerbating lupus," *Journal of Clinical Investigation* 112(8):1211-1222, Oct. 2003.

Zhang et al., "The Total Synthesis of Immunostimulant α-Galactosylceramides from Naturally Configured α-Galactoside Raffinose," *Organic Letters* 13(17):4530-4533, 2011.

* cited by examiner

ORGANIC COMPOUNDS AS PROANTIGENS FOR NATURAL KILLER T CELLS

CROSS-REFERENCE TO RELATED APPLICATIONS

This application is the national phase under 35 U.S.C. §371 of PCT International Application No. PCT/NZ2013/000133, filed Jul. 26, 2013, which claims priority to New Zealand Application No. 601473, filed Jul. 26, 2012, the entire contents of the aforementioned application are hereby incorporated herein by reference.

FIELD OF INVENTION

This invention relates generally to certain sphingoglycolipid analogues, precursors and prodrugs of these compounds, compositions comprising these compounds, including pharmaceutical compositions and adjuvant compositions, processes for preparing the compounds, and methods of treating or preventing diseases or conditions using such compounds, especially diseases or conditions relating to infection, atopic disorders, autoimmune disease, diabetes or cancer.

BACKGROUND

Invariant natural killer T-cells (NKT) are a subset of T-cells that are implicated in a broad range of diseases. In some circumstances they can enhance the response to infection (Kinjo, Illarionov et al. 2011) and cancer (Wu, Lin et al. 2011) but also possess the ability to suppress autoimmune disease (Hong, Wilson et al. 2001) and type II diabetes. Activation of NKT cells can also lead to undesirable immune responses as related to allergy, (Wingender, Rogers et al. 2011) autoimmunity (Zeng, Liu et al. 2003) and atherosclerosis (Tupin, Nicoletti et al. 2004).

Unlike conventional T-cells that are restricted by major histocompatibility complex (MHC) molecules that present peptide antigens, NKT cells are uniquely restricted by CD1d proteins (Bendelac, Savage et al. 2007). CD1d proteins belong to the CD1 family that contains five members, CD1a-e. Like MHC molecules, the CD1 family members all contain an antigen binding region that is flanked by two anti-parallel α-helices that sit above a β-sheet. Unlike MHC molecules, the binding region of the CD1 proteins contain two large hydrophobic binding pockets that are suited to bind lipid antigens rather than peptide based antigens (Li, Girardi et al. 2010). α-Galactosylceramide (α-GalCer) is the most studied NKT cell antigen and potently activates human and mouse NKT cells (Kawano, Cui et al. 1997). In animal studies, α-GalCer is reported to be useful in the treatment of a number of diseases including cancer, (Morita, Motoki et al. 1995; Motoki, Morita et al. 1995) and autoimmune disease (Hong, Wilson et al. 2001). The compound has also been shown to function as a potent vaccine adjuvant in the treatment and prophylaxis of cancer and infectious disease (Silk, Hermans et al. 2004). This adjuvant activity has been attributed to stimulatory interactions between activated NKT cells and dendritic cells (DCs), the most potent antigen-presenting cells in the body. As a consequence, the DCs are rendered capable of promoting strong adaptive immune responses (Fujii, Shimizu et al. 2003; Hermans, Silk et al. 2003).

Although α-GalCer has considerable biological activity it does have limitations such as poor solubility, (Ebensen, Link et al. 2007) lack of efficacy in human clinical trials, (Giaccone, Punt et al. 2002) promotion of T-cell anergy (Parekh, Wilson et al. 2005) and the generation of both Th1 and Th2 cytokines that may contribute to mixed results in model studies.

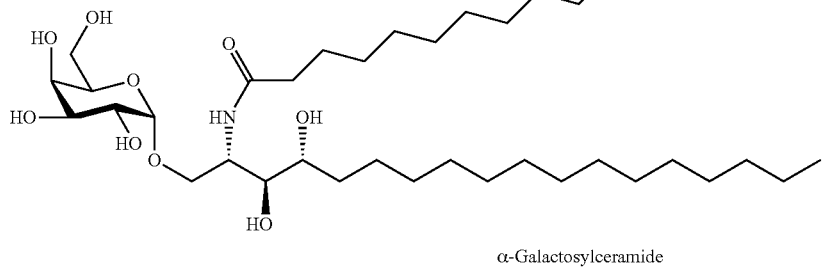

α-Galactosylceramide

It is therefore an object of the invention to provide novel compounds useful as agents for treating diseases or conditions relating to infection, autoimmune disease, atopic disorders or cancer, or to at least provide a useful alternative.

STATEMENTS OF INVENTION

In a first aspect, the invention provides a compound of formula (I):

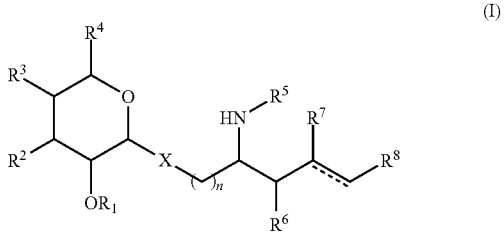

wherein:

R[1] is H or glycosyl, provided that if R[1] is glycosyl then R[2] and R[3] are both OH and R[4] is $CH_2OH$;

R[2] is selected from the group consisting of H, OH, F and $OR^{10}$, provided that if R[2] is H, F or $OR^{10}$, then R[1] is H, R[3] is OH and R[4] is $CH_2OH$;

R[3] is selected from the group consisting of H, OH, F and $OR^{10}$; provided that if R[3] is H, F or $OR^{10}$, then R[1] is H, R[2] is OH and R[4] is $CH_2OH$;

R[4] is $CH_3$, $CH_2OH$, $CH_2OCOR^{11}$, $CH_2OR^{10}$, $CH_2OR^{11}$, $CH_2OSO_3H$, $CH_2SH$, $CH_2SR^{11}$, $CH_2SOR^{11}$, $CH_2SO_2R^{11}$, $CH_2PO_3H_2$, $CH_2OP(O)(OH)_2$, $CH_2OP(O)(OH)(OR^{11})$, $CH_2OP(O)(OR^{11})_2$, $CO_2H$, $CH_2NHCOR^{11}$, $CH_2NHCO_2R^{11}$, $CH_2NHCONH_2$, $CH_2NHCONHR^{11}$, $CH_2NHCON(R^{11})_2$, $CH_2N(R^{11})_2$, $CH_2NHSO_2R^{11}$; provided that if R[4] is other than $CH_2OH$, then R[1] is H and R[2] and R[3] are OH;

R[5] is H;

or R[5] is a radical of formula (i):

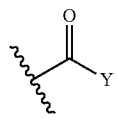
(i)

wherein Y is a radical of formula:

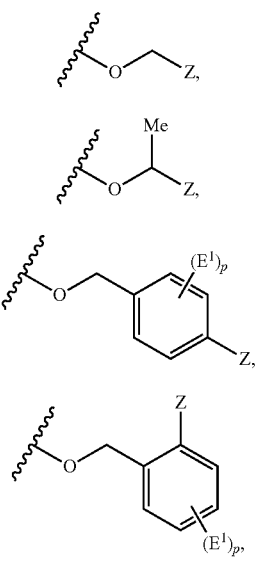
(a)
(b)
(c)
(d)
(e)
(f)

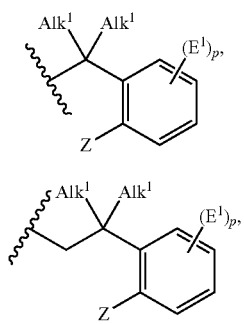

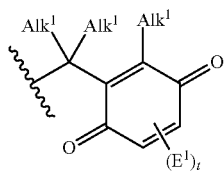
(g)

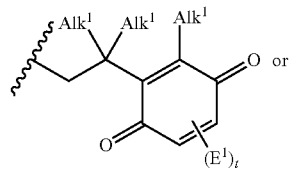
(h)

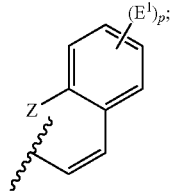
(j)

each E[1], the same or different, is independently selected from the group consisting of H, alkyl, alkoxy, halogen, nitroaryl; or, together with the ring to which it is attached, forms a fused bicyclic aryl group;

p is an integer from 1 to 4;

t is an integer from 1 to 2;

Alk[1] is $C_1$-$C_4$ straight chain alkyl;

wherein when Y is a radical of formula (a) or (b) then Z is:

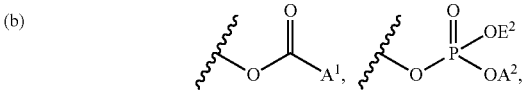

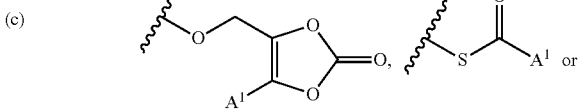

or wherein when Y is a radical of formula (c), (d), (e), (f) or (j) then Z is:

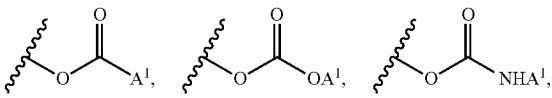

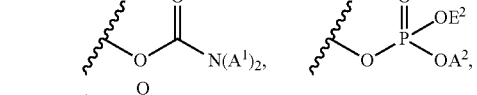

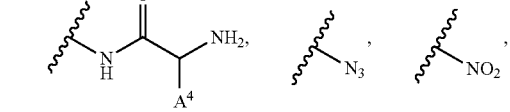

-continued

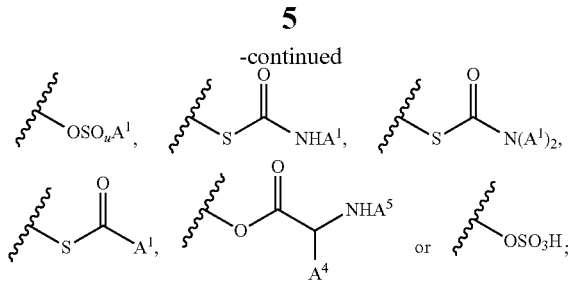

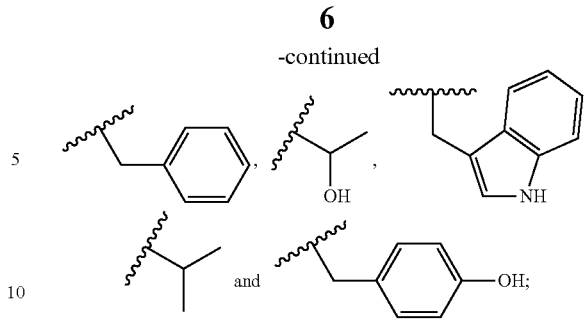

u is 1 or 2;
each $A^1$, the same or different, is independently selected from the group consisting of:
   alkyl which may be optionally substituted with one or more substituents selected from the group consisting of $(OCH_2CH_2)_mOMe$, $NHC(O)OR^{14}$, alkoxyimino, oxo, halogen, alkoxy, $NHCOCH_2(OCH_2CH_2)_mOMe$,

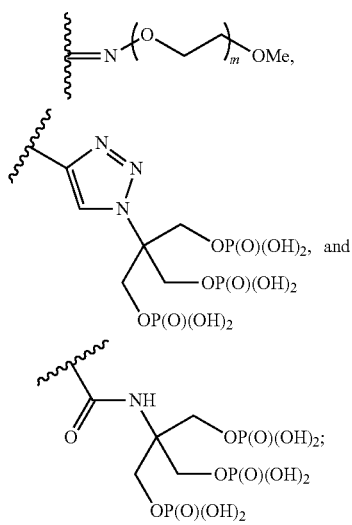

alkenyl which may be optionally substituted with one or more substituents selected from the group consisting of $(OCH_2CH_2)_mOMe$, alkoxyimino, oxo, halogen and alkoxy;
   aryl which may be optionally substituted with one or more substituents selected from the group consisting of $(OCH_2CH_2)_mOMe$, alkyl, alkoxy, dialkylamino, nitro, halogen; or
   aralkyl which may be optionally substituted with one or more substituents selected from the group consisting of $(OCH_2CH_2)_mOMe$, alkoxyimino, oxo, halogen, alkyl, alkoxy, dialkylamino and nitro;
m is an integer from 10 to 1500;
$E^2$ and $A^2$ are each independently selected from H and $A^1$;
$A^4$ is selected from the group consisting of H, methyl, $CH_2CH_2CH_2NHC(=NH)NH_2$, $CH_2C(=O)NH_2$, $CH_2C(=O)OH$, $CH_2SH$, $CH_2CH_2C(=O)OH$, $CH_2CH_2C(=O)NH_2$, $CH_2(CH_2)_3NH_2$, $CH_2CH_2SCH_3$, $CH_2OH$,

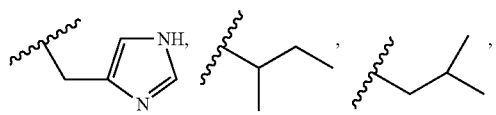

or $A^4$, together with the carbon to which it is attached and the nitrogen adjacent to that carbon, forms a pyrrolidine ring;
$A^5$ is H or benzyloxycarbonyl;
$R^6$ is $OR^{12}$, OH or H;
$R^7$ is $OR^{12}$, OH or H; provided that at least one of $R^6$ and $R^7$ is $OR^{12}$; wherein when $R^6$ is $OR^{12}$, $R^7$ is H, $R^8$ is $C_1$-$C_{15}$ alkyl and X is O, then ═══ denotes an optional double bond linking the carbon adjacent to $R^7$ with the carbon adjacent to $R^8$;
$R^8$ is H or $C_1$-$C_{15}$ alkyl having a straight or branched carbon chain, wherein the carbon chain optionally incorporates one or more double bonds, one or more triple bonds, one or more oxygen atoms and/or a terminal or non-terminal optionally substituted aryl group;
$R^{10}$ is glycosyl;
$R^{11}$ is lower alkyl, lower alkenyl or aralkyl;
$R^{12}$ is $C_6$-$C_{30}$ acyl having a straight or branched carbon chain optionally substituted with one or more hydroxy groups at positions 2 and/or 3 of the acyl group and/or an optionally substituted chain terminating aryl group and which optionally incorporates one or more double bonds, one or more triple bonds, and/or one or more optionally substituted arylene groups and wherein the carbon chain is optionally substituted with one or more deuterium atoms; wherein the optional substituents on the aryl and arylene groups may be selected from halogen, cyano, dialkylamino, $C_1$-$C_6$ amide, nitro, $C_1$-$C_6$ alkoxy, $C_1$-$C_6$ acyloxy and $C_1$-$C_6$ thioalkyl;
$R^{14}$ is an optionally substituted alkyl, aryl or aralkyl group;
X is O, $CH_2$ or S;
n is 1 when X is O or S; or n is 0 or 1 when X is $CH_2$;
wherein where X is $CH_2$ then the following must all be true: the stereochemistry of the 6-membered sugar ring in formula (I) is α-D-galacto; $R^1$ is H; $R^2$ and $R^3$ are both OH; $R^4$ is $CH_2OH$, $CH_2OR^{10}$ or $CH_2OR^{11}$; and:
$R^6$ is OH and $R^7$ is $OR^{12}$ and the stereochemistry at carbon atoms 2, 3 and 4 is (2S, 3S, 4R), (2S, 3S, 4S), (2R, 3S, 4S), (2R, 3S, 4R) or (2S, 3R, 4S); or
$R^6$ is $OR^{12}$ and $R^7$ is H, and $R^8$ is $C_{13}H_{27}$ and the stereochemistry at carbon atoms 2 and 3 is (2S, 3S);
wherein where X is S then the following must all be true: the stereochemistry of the 6-membered sugar ring in formula (I) is α-D-galacto; $R^1$ is H; $R^2$ and $R^3$ are both OH; $R^4$ is $CH_2OH$, $CH_2OR^{10}$, $CH_2OR^{11}$ or $CO_2H$; and:
$R^6$ is OH and $R^7$ is $OR^{12}$ and the stereochemistry at carbon atoms 2, 3 and 4 is (2S, 3S, 4R); or
$R^6$ is $OR^{12}$ and $R^7$ is H and the stereochemistry at the carbon atoms 2 and 3 is (2S, 3S);
or a pharmaceutically acceptable salt thereof.

Preferably, the compound of formula (I) is a compound of formula (Ia):

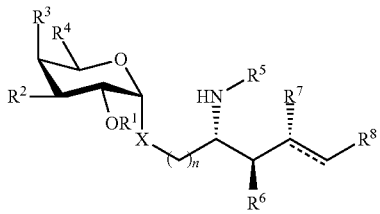

(Ia)

wherein X, $R^1$, $R^2$, $R^3$, $R^4$, $R^5$, $R^6$, $R^7$, $R^8$, $R^{10}$, $R^{11}$, $R^{12}$, $R^{14}$, $R^{15}$, $R^{16}$, Y, Z, $A^1$, $A^2$, $A^4$, $A^5$, $E^1$, $E^2$, $Alk^1$, p, t, m, u and n are all as defined above;
or a pharmaceutically acceptable salt thereof.

Preferably the stereochemistry of the 6-membered sugar ring of formula (I) is α-D-galacto.

Preferably X is O.

Preferably, n in formula (I) is 1, the stereochemistry of the 6-membered sugar ring of formula (I) is α-D-galacto, $R^6$ is OH and $R^7$ is $OR^{12}$. It is further preferred that n in formula (I) is 1, the stereochemistry of the 6-membered sugar ring of formula (I) is α-D-galacto, $R^6$ is OH, $R^7$ is $OR^{12}$ and the stereochemistry at carbon atoms 2, 3 and 4 is (2S, 3S, 4R).

Alternatively preferably, n in formula (I) is 0, X is $CH_2$, the stereochemistry of the 6-membered sugar ring of formula (I) is α-D-galacto, $R^6$ is OH and $R^7$ is $OR^{12}$. It is further preferred that n in formula (I) is 0, the stereochemistry of the 6-membered sugar ring of formula (I) is α-D-galacto, $R^6$ is OH, $R^7$ is $OR^{12}$ and the stereochemistry at carbon atoms 2, 3 and 4 is (2S, 3S, 4R).

Preferably, in formula (I) when X is O, $R^6$ is $OR^{12}$, $R^7$ is H, $R^8$ is $C_1$-$C_{15}$ alkyl and ===== is a double bond linking the carbon adjacent to $R^7$ with the carbon adjacent to $R^8$, then the stereochemistry at the carbon atoms 2, 3 is (2S, 3S).

Preferably $R^1$ is H.

It is also preferred that $R^2$ is OH. More preferably $R^1$ is H and $R^2$ is OH.

Preferably $R^3$ is OH.

Preferably $R^4$ is $CH_2OH$. It is also preferred that $R^4$ is $CH_2OH$ and $R^1$ is H. It is further preferred that $R^4$ is $CH_2OH$, $R^2$ is OH and $R^1$ is H. More preferably $R^4$ is $CH_2OH$, $R^1$ is H and $R^2$ and $R^3$ are both OH.

Preferably $R^6$ is OH. Alternatively it is preferred that $R^6$ is $OR^{12}$.

Preferably $R^7$ is $OR^{12}$. More preferably $R^7$ is $OR^{12}$ and $R^6$ is OH. Still more preferably $R^7$ is $OR^{12}$, $R^6$ is OH and X is O.

Alternatively it is preferred that $R^7$ is OH. More preferably $R^6$ is $OR^{12}$ and $R^7$ is OH.

Alternatively it is preferred that $R^6$ and $R^7$ are both $OR^{12}$.

Alternatively it is preferred that $R^7$ is H and $R^6$ is $OR^{12}$.

Preferably $R^8$ is $C_1$-$C_{15}$ alkyl. More preferably $R^8$ is $C_1$-$C_{15}$ alkyl having a straight or branched carbon chain containing no double bonds, triple bonds, oxygen atoms or aryl groups. Still more preferably $R^8$ is $C_{13}$ alkyl having a straight carbon chain containing no double bonds, triple bonds, oxygen atoms or aryl groups. Still more preferably $R^8$ is $C_1$-$C_{15}$ alkyl, $R^7$ is $OR^{12}$ and $R^6$ is OH. Still more preferably $R^8$ is $C_1$-$C_{15}$ alkyl, $R^7$ is $OR^{12}$, $R^6$ is OH and X is O.

Preferably $R^{11}$ is alkyl, more preferably lower alkyl.

Preferably $R^5$ is H.

Alternatively, it is preferred that $R^5$ is a radical of formula (i). More preferably X is O and $R^5$ is a radical of formula (i).

Preferably m is an integer from 10 to 25, more preferably m is an integer from 10 to 15. Alternatively preferably m is an integer from 100 to 150, more preferably m is an integer from 110 to 140. Still more preferably m is an integer from 120 to 130.

Preferably Y is

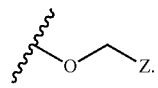

More preferably X is O and Y is

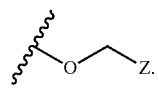

It is preferred that Z is

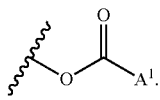

More preferably Z is

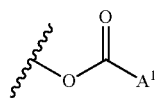

when Y is

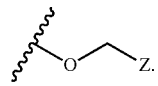

Alternatively, it is preferred that Z is

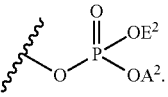

More preferably Z is

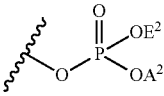

when Y is

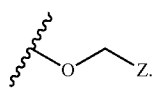

Preferably $A^1$ is alkyl, e.g. lower alkyl, e.g. methyl or t-butyl, or aryl, e.g. phenyl.

Alternatively preferably A' is alkyl substituted with one or more substitutents selected from the group consisting of $(OCH_2CH_2)_mOMe$, $NHC(O)OR^{14}$, alkoxyimino,

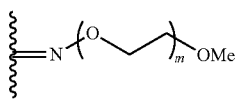

(where m is as defined herein, preferably an integer from 10 to 25, e.g. an integer from 10 to 15 or alternatively preferably an integer from 100 to 150, e.g. and integer from 105 to 140) and oxo; where m is an integer from 10 to 25, e.g. an integer from 10 to 15; $R^{14}$ is an optionally substituted alkyl, aryl or aralkyl group, e.g. a benzyl group. It is further preferred that $R^{14}$ is benzyl. Still more preferably $A^1$ is

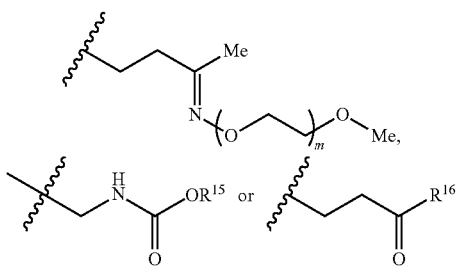

where m is as defined herein, preferably an integer from 10 to 25, e.g. an integer from 10 to 15, or alternatively preferably an integer from 100 to 150, e.g. and integer from 105 to 140; $R^{15}$ is aralkyl, e.g. benzyl; and $R^{16}$ is alkyl, e.g. lower alkyl, e.g. methyl.

Preferably $A^2$ is H. It is also preferred that $E^2$ is H. More preferably $A^2$ and $E^2$ are both H.

Preferably $R^5$ is a radical of formula (i) and $R^1$ is H, and $R^2$ and $R^3$ are OH. More preferably $R^5$ is a radical of formula (i) where Y is

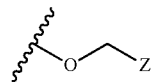

and $R^1$ is H, and $R^2$ and $R^3$ are OH. More preferably $R^5$ is a radical of formula (i) where Y is

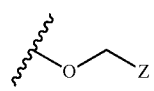

and $R^1$ is H, $R^2$ and $R^3$ are OH and $R^4$ is $CH_2OH$.

Preferably $R^{12}$ is acyl having a straight carbon chain from 6 to 30 carbon atoms long. More preferably $R^{12}$ is $C_{26}$ acyl.

More preferably $R^{12}$ is $C_{26}$ acyl having a straight carbon chain containing no double bonds, triple bonds, oxygen atoms, aryl groups and which is unsubstituted. More preferably X is O and $R^{12}$ is acyl having a straight carbon chain from 6 to 30 carbon atoms long.

Preferably any halogen in the compound of formula (I) or (Ia) is fluorine.

Preferably the compound of formula (I) is a compound selected from the group consisting of:

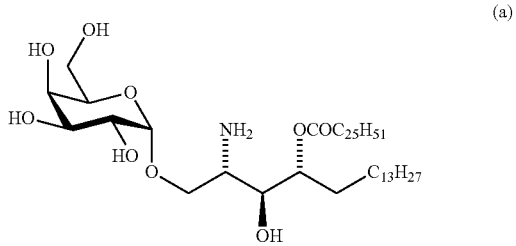

(a)

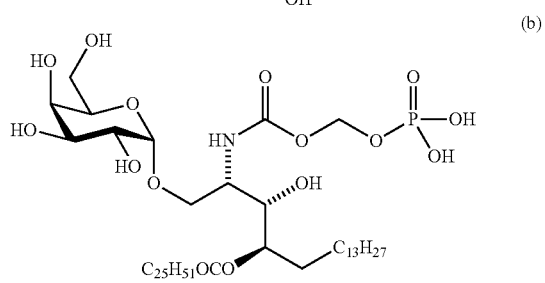

(b)

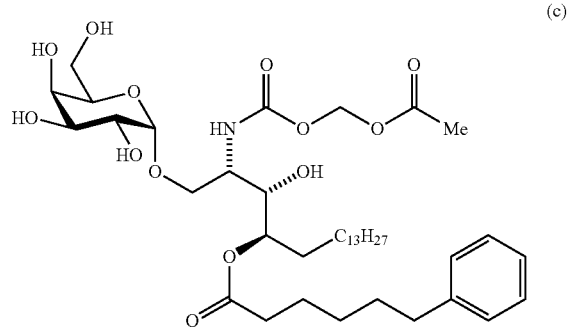

(c)

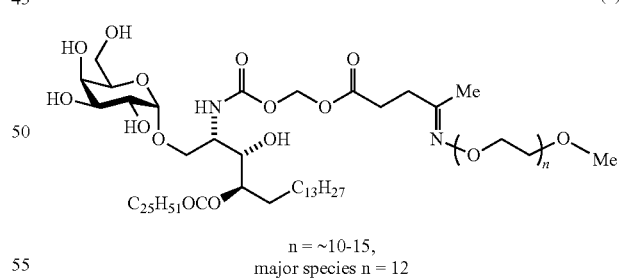

(d)

n = ~10-15, major species n = 12

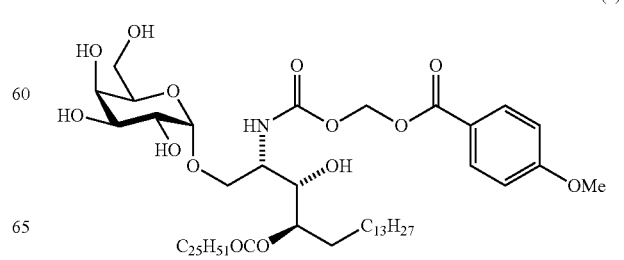

(e)

or a pharmaceutically acceptable salt thereof.

It is also preferred that the compound of formula (I) is a compound selected from the group consisting of:

(n) [structure with n = ~95-140]

(o) [structure]

(p) [structure with n = ~105-140]

or a pharmaceutically acceptable salt thereof.

In another aspect the invention provides a pharmaceutical composition comprising a pharmaceutically effective amount of a compound of formula (I) and optionally a pharmaceutically acceptable carrier.

In another aspect the invention provides an immunogenic composition comprising a compound of formula (I), an antigen and a pharmaceutically acceptable diluent.

In another aspect the invention provides a vaccine comprising a compound of formula (I), an antigen and a pharmaceutically acceptable diluent.

The antigen may be a bacterium such as *Bacillus* Calmette-Guérin (BCG), a virus or peptide. Examples of suitable antigens include, but are not limited to, Wilms' Tumor 1 (WT1), (Li, Oka et al. 2008) tumor-associated antigen MUC1, (Brossart, Heinrich et al. 1999) latent membrane protein 2 (LMP2), (Lu, Liang et al. 2006) HPV E6E7, (Davidson, Faulkner et al. 2004) NY-ESO-1 (Karbach, Gnjatic et al. 2010) and glycoprotein 100 (gp100) (Levy, Pitcovski et al. 2007).

In still another aspect the invention provides a compound of formula (I) in combination with at least one other compound, e.g. a second drug compound, e.g. an anti-bacterial agent or an anti-cancer agent such as Vemurafenib (PLX4032), Imatinib or Carfilzomib.

In yet another aspect the invention provides the use of a compound of formula (I) as a medicament.

In another aspect the invention provides the use of a compound of formula (I) for treating or preventing an infectious disease, an atopic disorder, an autoimmune disease, diabetes or cancer.

In another aspect the invention provides the use of a pharmaceutical composition comprising a pharmaceutically effective amount of a compound of formula (I), for treating or preventing an infectious disease, an atopic disorder, an autoimmune disease, diabetes or cancer.

In another aspect the invention provides a compound of formula (I) for use in the manufacture of a medicament.

In another aspect the invention provides a pharmaceutical composition for treating or an infectious disease, an atopic disorder, an autoimmune disease, diabetes or cancer, comprising a compound of formula (I).

In another aspect the invention provides the use of a compound of formula (I) in the manufacture of a medicament for treating or preventing an infectious disease, an atopic disorder, an autoimmune disease, diabetes or cancer.

In another aspect the invention provides a method of treating or preventing an infectious disease, an atopic disorder, an autoimmune disease, diabetes or cancer comprising administering a pharmaceutically effective amount of a compound of formula (I) to a patient requiring treatment.

In another aspect the invention provides the use of a compound of formula (I) in combination with at least one other compound, e.g. a second drug compound, e.g. an anti-bacterial agent or an anti-cancer agent such as Vemurafenib (PLX4032), Imatinib or Carfilzomib for treating or preventing an infectious disease, an atopic disorder, an autoimmune disease, diabetes or cancer.

In another aspect the invention provides a method of treating or preventing an infectious disease, an atopic disorder, an autoimmune disease, diabetes or cancer comprising administering to a patient a pharmaceutically effective amount of a compound of formula (I) in combination with at least one other compound, e.g. a second drug compound, e.g. an anti-bacterial agent or an anti-cancer agent such as Vemurafenib (PLX4032), Imatinib or Carfilzomib. The compound of formula (I) and the other compound may be administered separately, simultaneously or sequentially.

The diseases or conditions include cancer, e.g. melanoma, prostate, breast, lung, glioma, lymphoma, colon, head and neck and nasopharyngeal carcinoma (NPV); infectious diseases; bacterial infections; atopic diseases; or autoimmune diseases.

In another aspect the invention provides a method of modifying an immune response in a patient, comprising administering a compound of formula (I) and an antigen to the patient.

Preferably the patient is a human.

The compound of formula (I) may be selected from the group consisting of compounds (a), (b), (c), (d), (e), (f), (g), (h), (j), (k), (n), (o), (p) and (m) as defined above.

Compounds of formula (I) are described herein as "compounds of the invention". A compound of the invention includes a compound in any form, e.g. in free form or in the form of a salt or a solvate.

It will be appreciated that any of the sub-scopes disclosed herein, e.g. with respect to X, $R^1$, $R^2$, $R^3$, $R^4$, $R^5$, $R^6$, $R^7$, $R^8$, $R^{10}$, $R^{11}$, $R^{12}$, $R^{14}$, $R^{15}$, $R^{16}$, Y, Z, $A^1$, $A^2$, $A^4$, $A^5$, $E^1$, $E^2$, $Alk^1$, p, t, u, m and n may be combined with any of the other sub-scopes disclosed herein to produce further sub-scopes.

DETAILED DESCRIPTION

Definitions

The term "cancer" and like terms refer to a disease or condition in a patient that is typically characterized by abnormal or unregulated cell growth. Cancer and cancer pathology can be associated, for example, with metastasis, interference with the normal functioning of neighbouring cells, release of cytokines or other secretory products at abnormal levels, cell proliferation, tumour formation or growth, suppression or aggravation of inflammatory or immunological response, neoplasia, premalignancy, malignancy, invasion of surrounding or distant tissues or organs, such as lymph nodes, etc. Particular cancers are described in detail herein. Examples include lung, glioma, lymphoma, colon, head and neck and nasopharyngeal carcinoma (NPV), melanoma, chronic myelogenous leukemia (CML), myeloma, prostate, breast, glioblastoma, renal cell carcinoma, hepatic cancers.

"Infections" and like terms refer to diseases or conditions of a patient comprising internal and/or external growth or establishment of microbes. Microbes include all living forms too small to be seen by eye, including bacteria, viruses, fungi, and protozoa. Included are aerobic and anaerobic bacteria, and gram positive and gram negative bacteria such as cocci, bacilli, spirochetes, and mycobacteria. Particular infectious disorders are described in detail herein. Examples include bacterial or viral infections.

"Atopic disorders" and like terms refer to a disease or condition of a patient that is typically characterized by an abnormal or up-regulated immune response, for example, an IgE-mediated immune response, and/or Th2-cell immune response. This can include hypersensitivity reactions (e.g., Type I hypersensitivity), in particular, as associated with allergic rhinitis, allergic conjunctivitis, atopic dermatitis, and allergic (e.g. extrinsic) asthma. Typically, atopic disorders are associated with one or more of rhinorrhea, sneezing, nasal congestion (upper respiratory tract), wheezing, dyspnea (lower respiratory tract), itching (e.g., eyes, skin), nasal turbinate edema, sinus pain on palpation, conjunctival hyperemia and edema, skin lichenification, stridor, hypotension, and anaphylaxis. Particular atopic disorders are described in detail herein.

The term "patient" includes human and non-human animals. Non-human animals include, but are not limited to birds and mammals, in particular, mice, rabbits, cats, dogs, pigs, sheep, goats, cows, horses, and possums.

"Treatment" and like terms refer to methods and compositions to prevent, cure, or ameliorate a medical disease, disorder, or condition, and/or reduce at least a symptom of such disease or disorder. In particular, this includes methods and compositions to prevent or delay onset of a medical disease, disorder, or condition; to cure, correct, reduce, slow, or ameliorate the physical or developmental effects of a medical disease, disorder, or condition; and/or to prevent, end, reduce, or ameliorate the pain or suffering caused by the medical disease, disorder, or condition.

The term "alkyl" means any saturated hydrocarbon radical having up to 30 carbon atoms and includes any $C_1$-$C_{25}$, $C_1$-$C_{20}$, $C_1$-$C_{15}$, $C_1$-$C_{10}$, or $C_1$-$C_6$ alkyl group, and is intended to include both straight- and branched-chain alkyl groups. Examples of alkyl groups include: methyl group, ethyl group, n-propyl group, iso-propyl group, n-butyl group, iso-butyl group, sec-butyl group, t-butyl group, n-pentyl group, 1,1-dimethylpropyl group, 1,2-dimethylpropyl group, 2,2-dimethylpropyl group, 1-ethylpropyl group, 2-ethylpropyl group, n-hexyl group and 1-methyl-2-ethylpropyl group.

The term "lower alkyl" means any saturated hydrocarbon radical having from 1 to 6 carbon atoms and is intended to include both straight- and branched-chain alkyl groups.

Any alkyl group may optionally be substituted with one or more substituents selected from the group consisting of hydroxy and halogen, e.g. fluorine.

The term "alkenyl" means any hydrocarbon radical having at least one double bond, and having up to 30 carbon atoms, and includes any $C_2$-$C_{25}$, $C_2$-$C_{20}$, $C_2$-$C_{15}$, $C_2$-$C_{10}$, or $C_2$-$C_6$ alkenyl group, and is intended to include both straight- and branched-chain alkenyl groups. Examples of alkenyl groups include: ethenyl group, n-propenyl group, iso-propenyl group, n-butenyl group, iso-butenyl group, sec-butenyl group, t-butenyl group, n-pentenyl group, 1,1-dimethylpropenyl group, 1,2-dimethylpropenyl group, 2,2-dimethylpropenyl group, 1-ethyipropenyl group, 2-ethylpropenyl group, n-hexenyl group and 1-methyl-2-ethylpropenyl group.

The term "lower alkenyl" means any hydrocarbon radical having at least one double bond, and having from 2 to 6 carbon atoms, and is intended to include both straight- and branched-chain alkenyl groups.

Any alkenyl group may optionally be substituted with one or more substituents selected from the group consisting of alkoxy, hydroxy and halogen, e.g. fluorine.

The term "aryl" means an aromatic radical having 4 to 18 carbon atoms and includes heteroaromatic radicals. Examples include monocyclic groups, as well as fused groups such as bicyclic groups and tricyclic groups. Examples include phenyl group, indenyl group, 1-naphthyl group, 2-naphthyl group, azulenyl group, heptalenyl group, biphenyl group, indacenyl group, acenaphthyl group, fluorenyl group, phenalenyl group, phenanthrenyl group, anthracenyl group, cyclopentacyclooctenyl group, and benzocyclooctenyl group, pyridyl group, pyrrolyl group, pyridazinyl group, pyrimidinyl group, pyrazinyl group, triazolyl group (including a 1-H-1,2,3-triazol-1-yl and a 1-H-1,2,3-triazol-4-yl group), tetrazolyl group, benzotriazolyl group, pyrazolyl group, imidazolyl group, benzimidazolyl group, indolyl group, isoindolyl group, indolizinyl group, purinyl group, indazolyl group, furyl group, pyranyl group, benzofuryl group, isobenzofuryl group, thienyl group, thiazolyl group, isothiazolyl group, benzothiazolyl group, oxazolyl group, and isoxazolyl group.

The term "aralkyl" means an aryl group which is attached to an alkylene moiety, where aryl is as defined above. Examples include benzyl group.

Any aryl or aralkyl group may optionally be substituted with one or more substituents selected from the group consisting of alkyl, halogen, cyano, dialkylamino, amide (both N-linked and C-linked: —NHC(O)R and —C(O)NHR), nitro, alkoxy, acyloxy and thioalkyl.

The term "alkoxy" means an OR group, where R is alkyl as defined above. The term "lower alkoxy" means an OR group, where R is "lower alkyl" as defined above.

The term "alkenyloxy" means an OR' group, where R' is alkenyl as defined above.

The term "aryloxy" means an OR" group, where R" is aryl as defined above.

The term "acyl" means C(=O)R'" group, where R'" is alkyl as defined above.

The term "glycosyl" means a radical derived from a cyclic monosaccharide, disaccharide or oligosaccharide by removal of the hemiacetal hydroxy group. Examples include α-D-glucopyranosyl, α-D-galactopyranosyl, β-D-galactopyranosyl, α-D-2-deoxy-2-acetamidogalactopyranosyl.

The term "amide" includes both N-linked (—NHC(O)R) and C-linked (—C(O)NHR) amides.

The term "pharmaceutically acceptable salt" is intended to apply to non-toxic salts derived from inorganic or organic acids, including, for example, the following acid salts: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, p-toluenesulfonate, salicylate, succinate, sulfate, tartrate, thiocyanate, and undecanoate.

For the purposes of the invention, any reference to the disclosed compounds includes all possible formulations, configurations, and conformations, for example, in free form (e.g., as a free acid or base), in the form of salts or hydrates, in the form of isomers (e.g., cis/trans isomers), stereoisomers such as enantiomers, diastereomers and epimers, in the form of mixtures of enantiomers or diastereomers, in the form of racemates or racemic mixtures, or in the form of individual enantiomers or diastereomers. Specific forms of the compounds are described in detail herein.

Any reference to prior art documents in this specification is not to be considered an admission that such prior art is widely known or forms part of the common general knowledge in the field.

As used in this specification, the words "comprises", "comprising", and similar words, are not to be interpreted in an exclusive or exhaustive sense. In other words, they are intended to mean "including, but not limited to".

The Compounds of the Invention

The compounds of the invention, particularly those exemplified, are useful as pharmaceuticals, particularly for the treatment or prevention of diseases or conditions relating to infection, atopic disorders, autoimmune disease or cancer. The compounds of the invention are also useful as vaccine adjuvants. For example, a compound of the invention may be formulated in a vaccine together with one or more antigens.

The compounds of the invention are useful in both free base form and in the form of salts and/or solvates.

The carbon atoms of the acyclic moiety of the compounds of formula (I) are numbered as shown below. This is the numbering used herein to denote these carbon atoms.

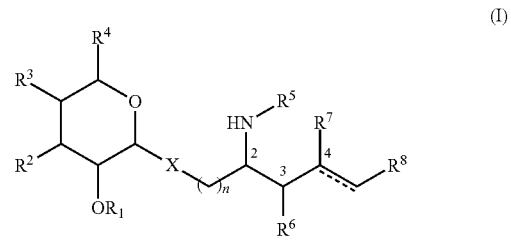

The invention relates to the surprising finding that, in the synthesis of α-GalCer, hydrogenolytic deprotection of compound 1 with Pd(OH)$_2$ leads to the isolation of significant quantities of CN089 (Scheme 1). In particular, when 1 is subjected to Pd(OH)$_2$-catalyzed hydrogenolysis in 3:7 CHCl$_3$/MeOH at 35° C., in addition to the expected product a more polar compound is isolated in 17% yield. This compound is determined to be amine CN089, an isomer of α-GalCer in which the C$_{26}$-acyl chain has undergone a 1,3 N→O migration. The location of the acyl group on O4 of the side-chain is established using 2D-NMR techniques. Although intramolecular N→O migrations of acyl groups are known in the literature they are usually promoted in strongly acidic media (Baadsgaard and Treadwell 1955; Drefahl and Hörhold 1961; Butler, O'Regan et al. 1978;

Schneider, Hackler et al. 1985; Johansen, Kornø et al. 1999). Without wishing to be bound by theory, the applicants hypothesise that, in the present case, it would appear that a certain amount of HCl is produced from the solvent $CHCl_3$ under the hydrogenolytic conditions, leading to the observed migration. A control experiment shows that, under similar reaction conditions, but in the absence of a $H_2$-atmosphere, α-GalCer does not isomerize to CN089. Although the formation of HCl from $CHCl_3$ by Pd-catalyzed hydrogenolysis has been reported, (Secrist and Logue 1972; Turner, Booher et al. 1977) its use (deliberate or otherwise) to isomerize amides to esters has not. Indeed, $CHCl_3$ has been successfully used as a co-solvent in the final deprotection step (hydrogenolysis) of other syntheses of α-GalCer or analogues thereof, with no report of acyl-migration side-reactions (Murata, Toba et al. 2005; Luo, Kulkarni et al. 2006; Matto, Modica et al. 2007; Park, Lee et al. 2008; Tashiro, Hongo et al. 2008; Cheng, Chee et al. 2011; Zhang, Zhao et al. 2011).

Scheme 1

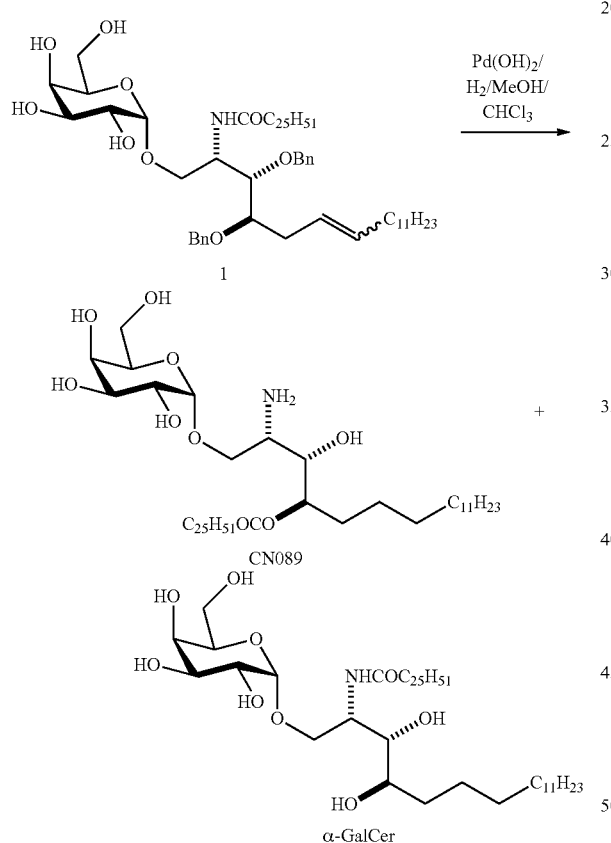

Alternative conditions for the formation of CN089 are as follows: when α-GalCer is heated in 1,4-dioxane with aq HCl, N→O migration of the $C_{26}$-acyl chain is effected and CN089 is isolated in 65-70% yield after chromatography.

When injected into mice CN089 potently activates DCs in an NKT cell-dependent manner, as defined by increased expression of the activation marker CD86 on the surface of splenic DCs (FIG. 1). The observed activity is due to reversion of CN089 to α-GalCer prior to injection. Within 1 hour of formulation of CN089, approximately 50% conversion to α-GalCer can be observed by LCMSMS. When the O→N acyl-migration is deliberately blocked by acetylation of the amino group (i.e. compound CN090), no activation of DCs is observed, suggesting that the positioning of the $C_{26}$-acyl chain on O4 (as in CN089) leads to an inactive construct.

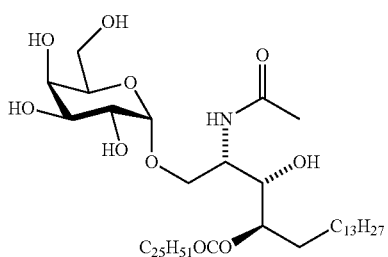

CN090

It has now been found that compounds of the invention (shown as compounds of formula (I') in Scheme 2) containing a "trigger" group ($R^5$) attached to the amino group of CN089 or its congeners are useful as pharmaceuticals. Without wishing to be bound by theory, the applicants propose that such are chemically stable, but can be cleaved enzymatically or at specific sites in vivo, and constitute useful prodrugs that can serve as precursors to amines (I") (e.g. CN089) which may in turn undergo O→N acyl-migration, leading to amides (II) (e.g. α-GalCer). Those skilled in the art will appreciate that compounds of formula (I") are also compounds of the invention, where $R^5$ is H.

Scheme 2

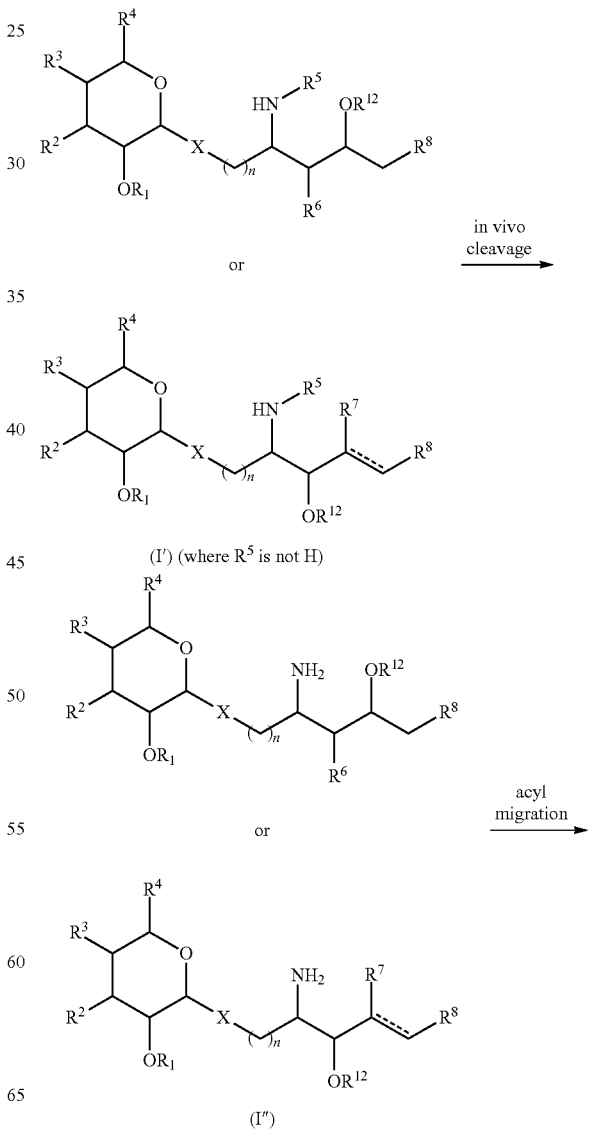

-continued

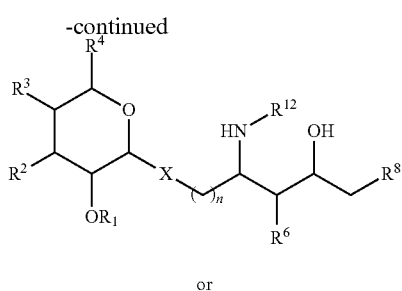

or

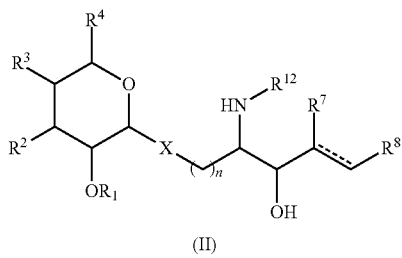

(II)

A benefit of the approach described herein is that $R^5$ can be varied widely to tune the physical properties and pharmacokinetics of the compounds of the invention, and yet a common product (e.g. α-GalCer) should be released after in vivo metabolism, whose capacity to interact with CD1d and activate NKT cells is identical to that of the parent compound (e.g. α-GalCer).

Thus, in a further embodiment of the invention, compounds (I″) can be chemically modified to produce a series of prodrug compounds, which are compounds of formula (I) of the invention (e.g. those shown in Table 1 and Scheme 3).

Scheme 3

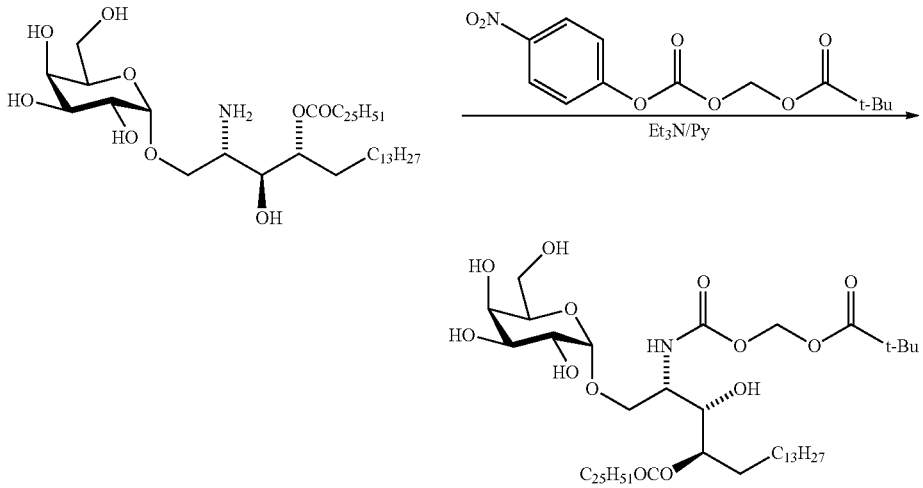

TABLE 1

Certain Compounds of the Invention

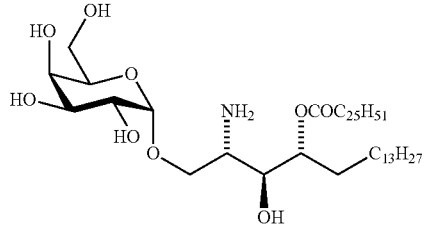
CN089

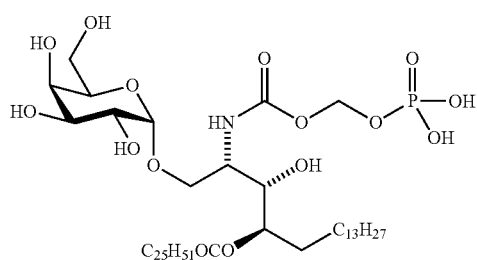
CN131

TABLE 1-continued
Certain Compounds of the Invention
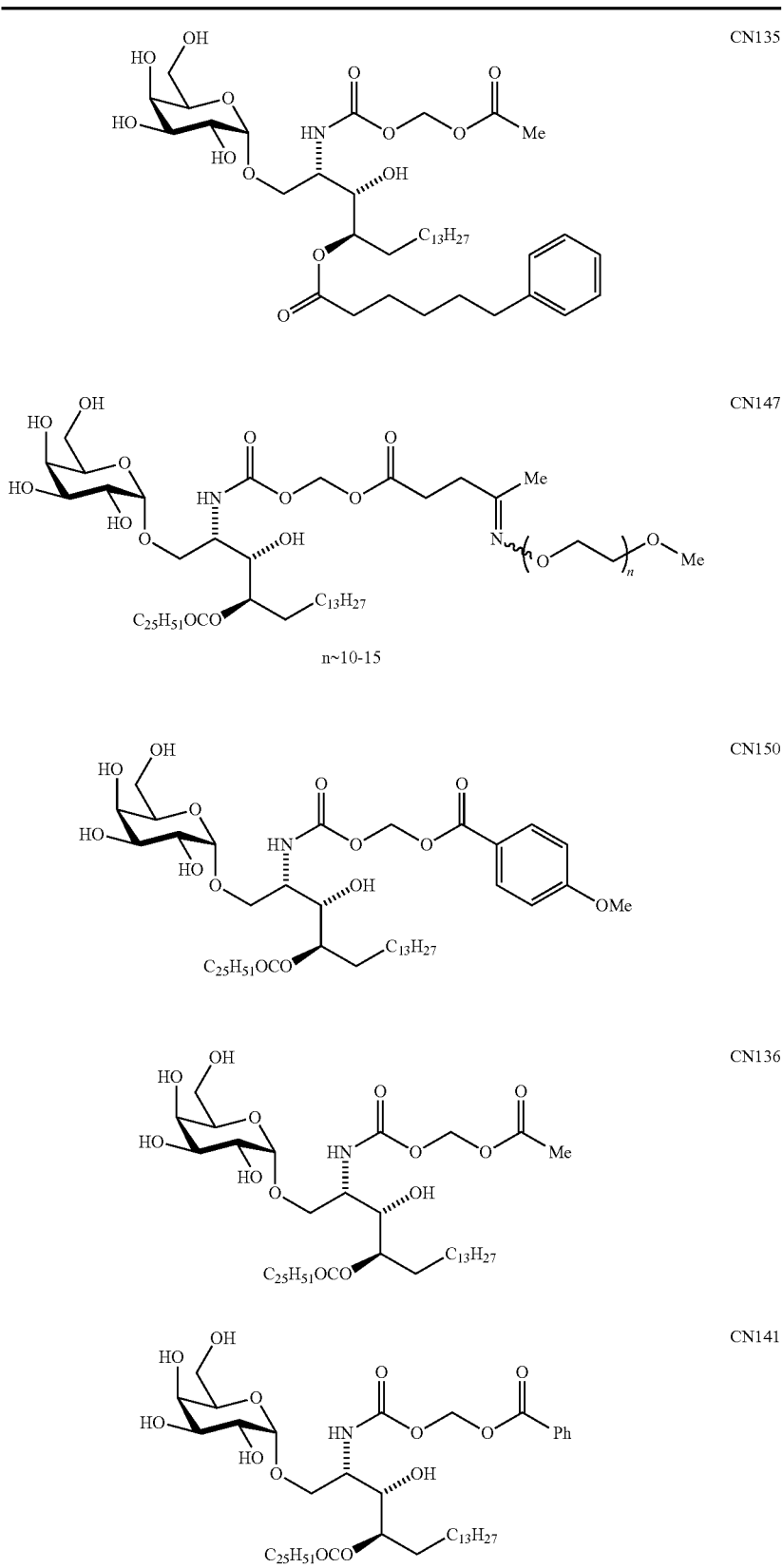

TABLE 1-continued
Certain Compounds of the Invention
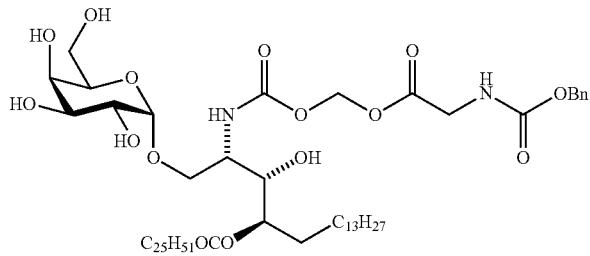
CN142
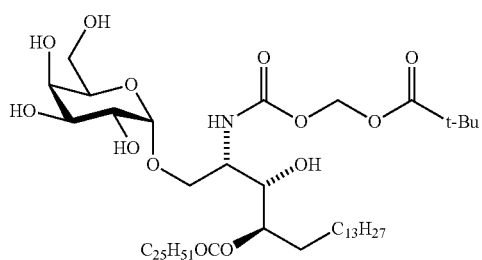
CN145
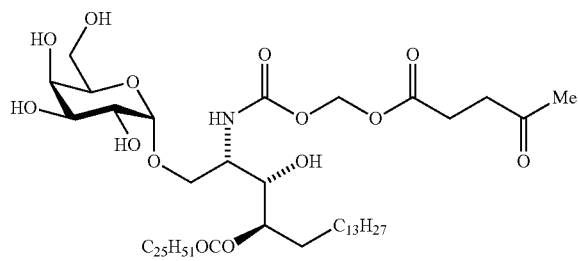
CN146
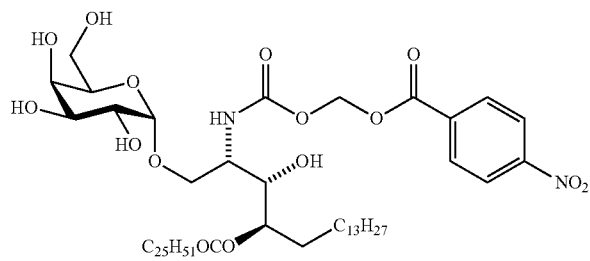
CN151
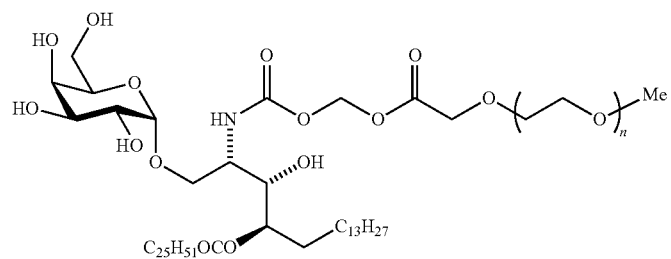
CN155
n~95-140

TABLE 1-continued

Certain Compounds of the Invention

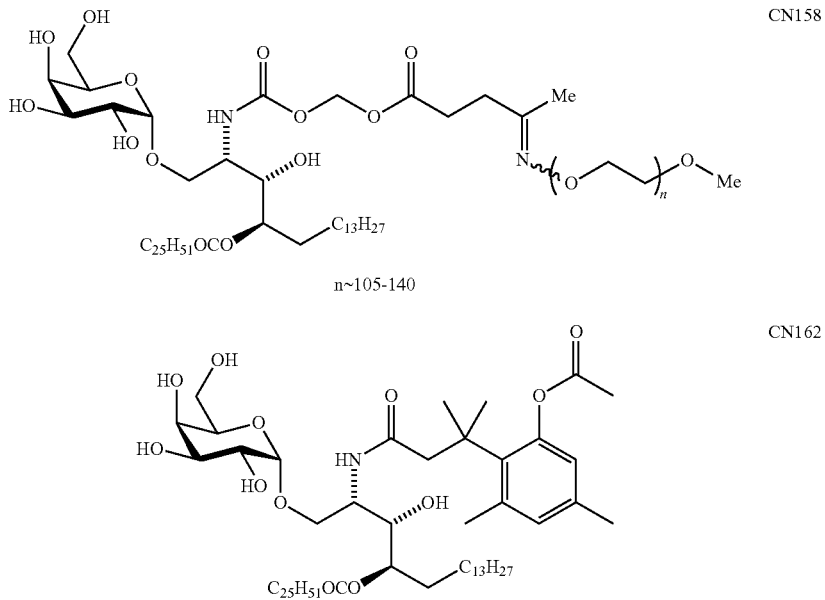

It is shown that, similarly to α-GalCer, the compounds of the invention stimulate NKT cells, as measured by DC activation in vivo (FIG. 2).

Surprisingly though, NKT cell activation by certain compounds of the invention, such as CN141, CN145, CN147 and CN158 induces the production of different cytokine profiles in vivo, as compared to those induced by α-GalCer (FIGS. 3 and 8). Injection of α-GalCer induces the production of a well-documented cytokine profile with IL-4 levels peaking in the serum after 2-3 h, followed by high levels of IL-12p70 peaking at 6 h, and IFN-γ peaking after 12 h. In contrast, the compounds CN141, CN145 and CN147 produce profiles with a higher ratio of IFN-γ to IL-4 than that of α-GalCer, and levels of IL-12p70 that are still increasing through 6 to 12 h. A profile of release favouring IFN-γ over IL-4, and sustained IL-12p70, is expected to be beneficial for the treatment of cancer when the compounds are used as single agents. In some settings, a Th1 bias (high IFN-γ/IL-4 ratio) may provide an advantage when the compounds are used as adjuvants, particularly in vaccine settings where Th1-biased T cells or cytotoxic T lymphocytes are desired, such as cancer, microbial infection or allergy (Fujii, Shimizu et al. 2002; Wu, Lin et al. 2011).

Perhaps more surprising is the fact that no systemic cytokines are detected for CN158 (FIG. 8) yet the compound is able to act as an effective immune adjuvant when co-administered with a model tumour antigen, providing a similar T cell response (FIG. 9) and anti-tumour activity (FIG. 10) as compared to antigen co-administered with α-GalCer. The adjuvant properties of the glycolipid are therefore more important than high quantities of cytokine release triggered by NKT cells in this model of therapy. Indeed, some studies suggest that high levels of inflammatory cytokines at the time of priming can actually have a negative impact on the quality of T cell responses, and should be avoided in vaccine strategies (Badovinac, Porter et al. 2004). Thus, the invention provides the benefit that compounds can be "tuned" to reduce the production of cytokines in vivo, yet retain adjuvant activities, which may be of benefit in some vaccination strategies. Compounds CN141 and CN145 also fall into this category, as they are not as potent as α-GalCer in terms of overall levels of cytokine production (FIG. 3) but are equally beneficial in promoting immune responses that suppress growth of established tumours in a murine melanoma model (FIG. 4). Overall, these results demonstrate that skewing of the cytokine profile, or a significant reduction in cytokines, can be achieved, by chemical modification of the group $R^5$ of compounds of the invention, leading to beneficial outcomes.

Without wishing to be bound by theory, the applicants propose that a possible explanation for these observations may lie in different pharmacokinetics of the compounds of the invention compared to those of α-GalCer (Sullivan, Nagarajan et al. 2010). For example, compounds CN141, CN150 and CN151 are synthesized. CN150 contains an electron donating para-methoxyl substituent on the phenyl ring, potentially slowing the cleavage of the benzoate ester bond compared to CN141. In contrast, CN151 contains an electron withdrawing para-nitro substituent, potentially increasing the rate of cleavage. Indeed this would appear to be the case since CN151 gives more activation than CN141 and CN141 gives more activation than CN150 at an early time point (FIG. 5, day 1) whereas at a later time point (day 3) a similar activation can be observed for CN141 and CN150.

Certain compounds of the invention e.g., CN147 and CN158, with water solubilities of ca 0.5 mg/mL and 38 mg/mL, respectively, provide the advantage of increased solubility (compared to α-GalCer) and are indicated for direct use, without the need for prior formulation. The low water solubility of α-GalCer necessitates its formulation (Giaccone, Punt et al. 2002) adding expense and time to any drug development programme and final product cost.

The biological activity of certain compounds of the invention (e.g. CN141 and CN145) is not limited to murine systems as these compounds are able to induce the expansion of human NKT cells from peripheral blood mononuclear cells (PBMC, FIG. 6).

Other Aspects

The compounds of the invention may be administered to a patient by a variety of routes, including orally, parenterally, by inhalation spray, topically, rectally, nasally, buccally, intravenously, intra-muscularly, intra-dermally, subcutaneously or via an implanted reservoir, preferably intravenously. The amount of compound to be administered will vary widely according to the nature of the patient and the nature and extent of the disorder to be treated. Typically the dosage for an adult human will be in the range 50-4800 $\mu g/m^2$. The specific dosage required for any particular patient will depend upon a variety of factors, including the patient's age, body weight, general health, sex, etc.

For oral administration the compounds of the invention can be formulated into solid or liquid preparations, for example tablets, capsules, powders, solutions, suspensions and dispersions. Such preparations are well known in the art as are other oral dosage regimes not listed here. In the tablet form the compounds may be tableted with conventional tablet bases such as lactose, sucrose and corn starch, together with a binder, a disintegration agent and a lubricant. The binder may be, for example, corn starch or gelatin, the disintegrating agent may be potato starch or alginic acid, and the lubricant may be magnesium stearate. For oral administration in the form of capsules, diluents such as lactose and dried corn-starch may be employed. Other components such as colourings, sweeteners or flavourings may be added.

When aqueous suspensions are required for oral use, the active ingredient may be combined with carriers such as water and ethanol, and emulsifying agents, suspending agents and/or surfactants may be used. Colourings, sweeteners or flavourings may also be added.

The compounds may also be administered by injection in a physiologically acceptable diluent such as water or saline. The diluent may comprise one or more other ingredients such as ethanol, propylene glycol, an oil or a pharmaceutically acceptable surfactant. In one preferred embodiment, the compounds are administered by intravenous injection, where the diluent comprises an aqueous solution of sucrose, L-histidine and a pharmaceutically acceptable surfactant, e.g. Tween 20.

The compounds may also be administered topically. Carriers for topical administration of the compounds include mineral oil, liquid petrolatum, white petrolatum, propylene glycol, polyoxyethylene, polyoxypropylene compound, emulsifying wax and water. The compounds may be present as ingredients in lotions or creams, for topical administration to skin or mucous membranes. Such creams may contain the active compounds suspended or dissolved in one or more pharmaceutically acceptable carriers. Suitable carriers include mineral oil, sorbitan monostearate, polysorbate 60, cetyl ester wax, cetearyl alcohol, 2-octyldodecanol, benzyl alcohol and water.

The compounds may further be administered by means of sustained release systems. For example, they may be incorporated into a slowly dissolving tablet or capsule.

Synthesis of the Compounds of the Invention

The overall synthetic strategy includes the isomerization of α-GalCer or its congeners (which are compounds of formula (II) as shown above in Scheme 2) under acidic conditions to give compounds with a free amino group where the fatty acid has migrated to an O-atom on the sphingosine chain (compounds of formula (I''), which are compounds of the invention) followed by subsequent functionalisation of the free amine to give compounds of formula (I') of the invention (e.g. as shown in Schemes 4, 5 and 7). Certain targets may not be accessible by this approach. An alternative strategy, shown in Scheme 6, involves the synthesis of N-protected intermediates 6 followed by acylation of the sphingosine chain hydroxyl group(s) with $R^{12}$ to give compounds 7. After various functional group transformations, the N-protecting group is cleaved to give compounds of formula (I''), which are converted to compounds of formula (I') in the usual manner.

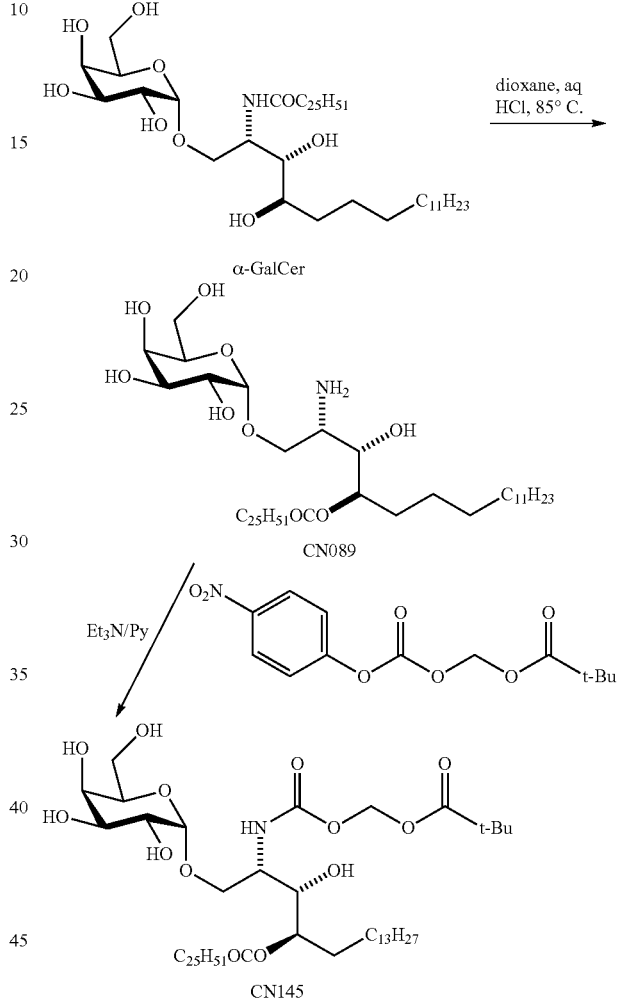

Compounds (I'') of the invention are prepared according to the following general procedures:

General Method (1) for the Synthesis of Compounds of Formula (I'')
(wherein $R^4$ is Me, $CH_2OH$, $CH_2OR^{10}$, $CH_2OR^{11}$, $CO_2H$; $R^6$ is OH and $R^7$ is $OR^{12}$, or $R^6$ is H and $R^7$ is $OR^{12}$, or $R^6=OR^{12}$ and $R^7=H$.)

Scheme 5

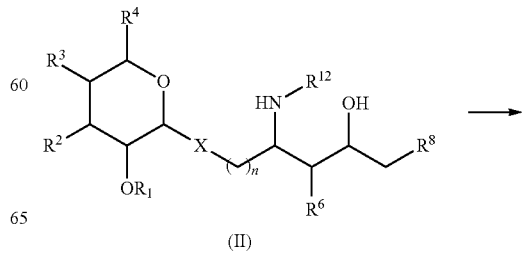

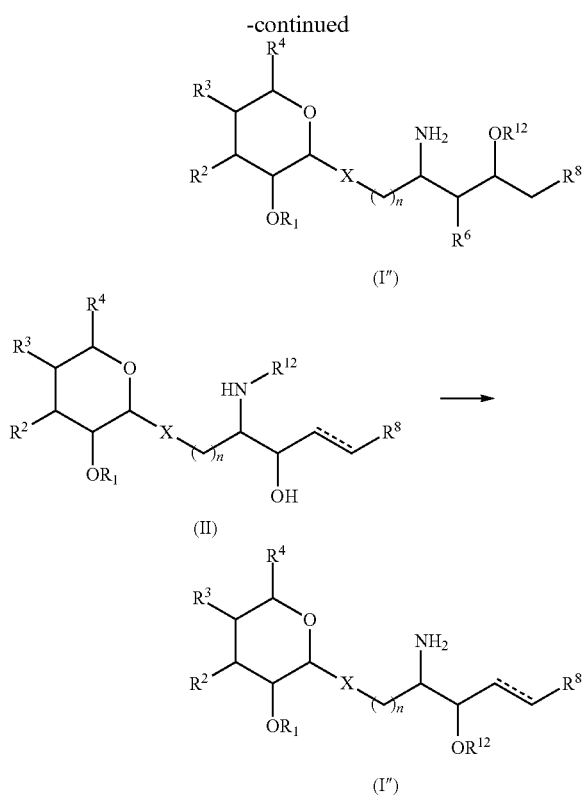

(I″)

(II)

(I‴)

Starting materials of formula (II) (wherein $R^4$ is Me, $CH_2OH$, $CH_2OR^{10}$, $CH_2OR^{11}$ or $CO_2H$; and $R^6$ is OH and $R^7$ is OH, or $R^6$ is H and $R^7$ is OH, or $R^6$ is OH and $R^7$ is H) are synthesized according to literature methods referenced herein, and in some cases, by combining elements of two or more literature methods. (For a recent review of α-GalCer analogues synthesized, see Banchet-Cadeddu et al (Banchet-Cadeddu, Henon et al. 2011)). For example, a key step in all syntheses of α-GalCer is the coupling of a suitably protected donor with a suitably functionalized acceptor in a glycosylation reaction. A wide variety of donors has been used in the synthesis of α-GalCer analogues, which allows variation of groups $R^1$-$R^4$ and the stereochemistry of these groups. Methods for the synthesis of donors where $R^1$ is glycosyl, (Veerapen, Brigl et al. 2009) $R^2$ or $R^3$ is O-glycosyl, (Kawano, Cui et al. 1997) $R^2$ or $R^3$ is either H or F, (Raju, Castillo et al. 2009) $R^4$ is Me, (Tashiro, Nakagawa et al. 2008) $CH_2OR^{10}$, (Uchimura, Shimizu et al. 1997) $CH_2OR^{11}$, (Tashiro, Nakagawa et al. 2008) or $CO_2H$, (Deng, Mattner et al. 2011) have been reported. An equally large variety of acceptors have also been employed. For example, all 8 stereoisomers of a protected phytospingosine acceptor have been synthesized in an approach that also allows modification of the group $R^8$ (Park, Lee et al. 2008; Baek, Seo et al. 2011). Furthermore, 3-deoxy (Baek, Seo et al. 2011) and 4-deoxy phytosphingosine (Morita, Motoki et al. 1995; Howell, So et al. 2004; Du, Kulkarni et al. 2007) derivatives have also been described. Combination of these acceptors with various donors leads to protected α-GalCer derivatives which are transformed, by literature methods referenced above, to the unprotected α-GalCer analogues, which comprise the starting materials (II) (where X is O) in the present General Method 1. For starting materials (II) in which X is $CH_2$ and $R^7$ is OH, syntheses have been described (Chen, Schmieg et al. 2004; Lu, Song et al. 2006; Wipf and Pierce 2006; Pu and Franck 2008). Variation of the group $R^4$ is available by adapting the protecting group chemistry used on intermediates XI and XII in the reported procedures.

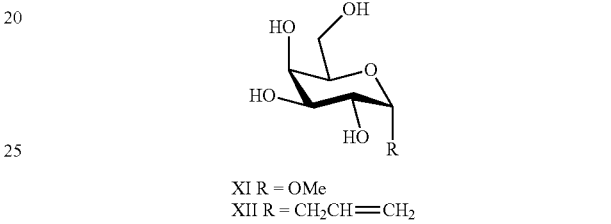

XI R = OMe
XII R = $CH_2CH=CH_2$

For starting materials (II) where X is $CH_2$ and $R^7$ is H, these are synthesized according to reported methods (Chen, Schmieg et al. 2004) using sphingosine as the starting material in place of phytosphingosine. For starting materials (II) in which X is S, syntheses have been described (Dere and Zhu 2008; O'Reilly and Murphy 2011).

The starting material (II) (~5 mM) is stirred in a suitable solvent (eg 10:1 1,4-dioxane-water) with acid (eg 1 M HCl, TFA) at an appropriate temperature (60-100° C.) until the reaction is judged to be ~75% complete (TLC). The solvents are removed and the crude residue is purified by column chromatography on silica gel.

Alternative General Method (2) for Synthesis of Compounds of Formula (I‴).

(wherein X is O; $R^1$ is H; $R^2$ and $R^3$ are OH; $R^4$ is Me, $CH_2OH$, $CH_2OCOR^{11}$, $CH_2SH$, $CH_2SR^{11}$, $CH_2SOR^{11}$, $CH_2SO_2R^{11}$, $CH_2NHCOR^{11}$, $CH_2NHCO_2R^{11}$, $CH_2NHCONH_2$, $CH_2NHCONHR^{11}$, $CH_2NHCONHR^{11}$, $CH_2NHCON(R^{11})_2$, $CH_2NHSO_2R^{11}$, $CH_2PO_3H_2$, $CH_2OSO_3H$ or $CH_2OPO_3H$; $R^6$ is $OR^{12}$ and $R^7$ is OH, or $R^6$ is OH and $R^7$ is $OR^{12}$, or $R^6$ and $R^7$ are $OR^{12}$, or $R^6$ is H and $R^7$ is $OR^{12}$, or $R^6$ is $OR^{12}$ and $R^7$ is H.)

Scheme 6

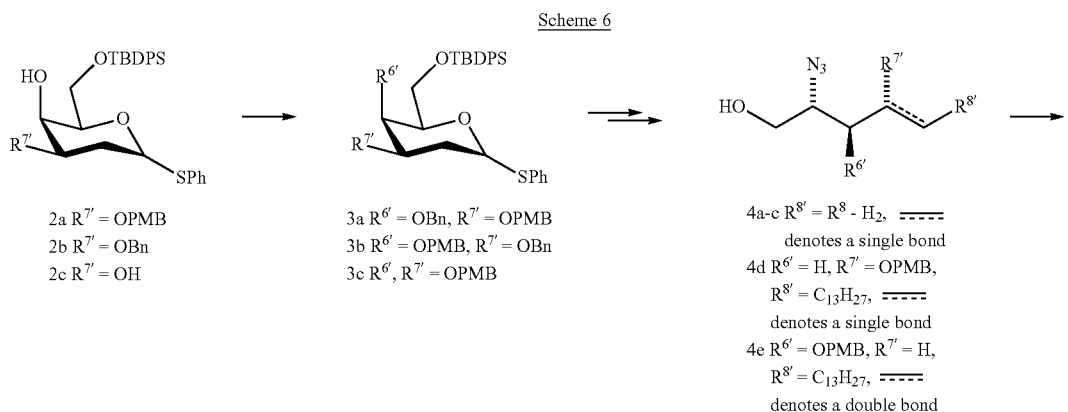

2a $R^{7'}$ = OPMB
2b $R^{7'}$ = OBn
2c $R^{7'}$ = OH

3a $R^{6'}$ = OBn, $R^{7'}$ = OPMB
3b $R^{6'}$ = OPMB, $R^{7'}$ = OBn
3c $R^{6'}, R^{7'}$ = OPMB 4a-c $R^{8'}$ = $R^8$ - $H_2$, ----- denotes a single bond
4d $R^{6'}$ = H, $R^{7'}$ = OPMB, $R^{8'}$ = $C_{13}H_{27}$, ----- denotes a single bond
4e $R^{6'}$ = OPMB, $R^{7'}$ = H, $R^{8'}$ = $C_{13}H_{27}$, ----- denotes a double bond -continued
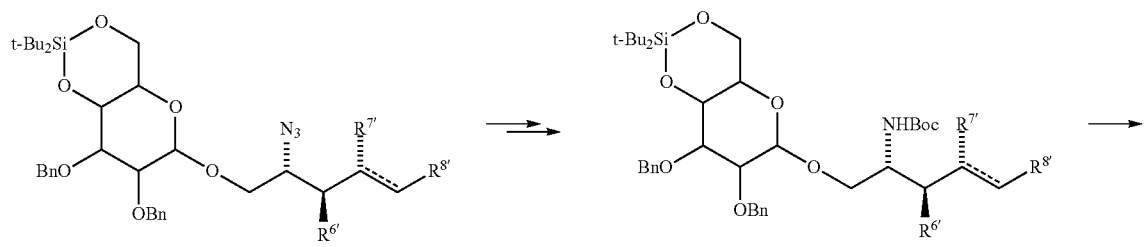
5a-e
6a R6' = OBn, R7' = OPMB
6b R6' = OPMB, R7' = OBn
6c R6', R7' = OPMB
6d R6' = H, R7' = OPMB
6e R6' = OPMB, R7' = H
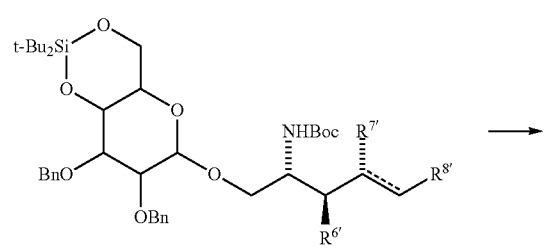
7a R6' = OBn, R7' = OR12
7b R6' = OR12, R7' = OBn
7c R6', R7' = OR12
7d R6' = H, R7' = OR12
7e R6' = OR12, R7' = H
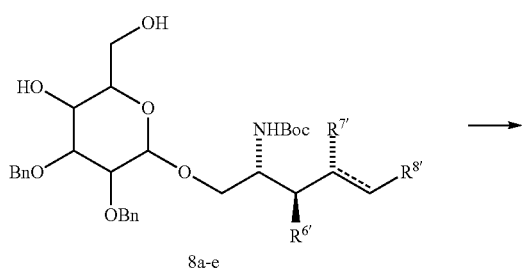
8a-e
1. H2, Pd(OH)2/C
2. TFA
1. esterification/sulfation/phosphorylation
2. H2, Pd(OH)2/C
3. TFA
(I'')
(R4 = CH2OH)
(I'')
(R4 = CH2OSO3H,
CH2OPO3H)

-continued

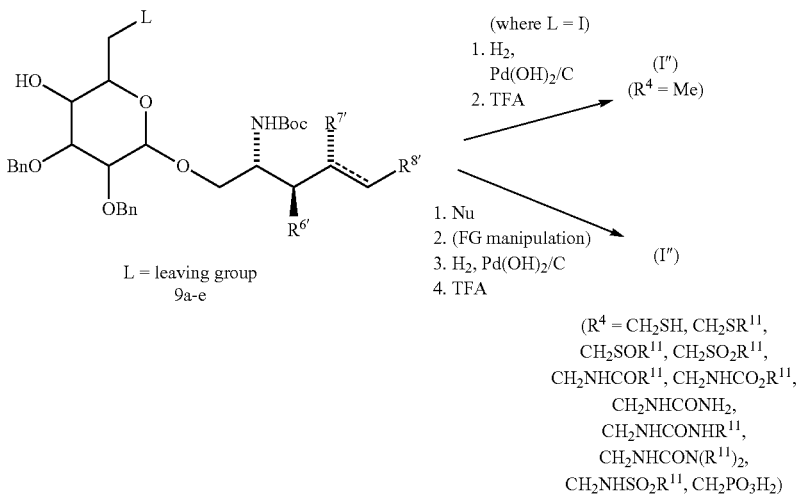

L = leaving group
9a-e (where L = I)
1. H$_2$, Pd(OH)$_2$/C
2. TFA
→ (I″) (R$^4$ = Me)

1. Nu
2. (FG manipulation)
3. H$_2$, Pd(OH)$_2$/C
4. TFA
→ (I″)

(R$^4$ = CH$_2$SH, CH$_2$SR$^{11}$, CH$_2$SOR$^{11}$, CH$_2$SO$_2$R$^{11}$, CH$_2$NHCOR$^{11}$, CH$_2$NHCO$_2$R$^{11}$, CH$_2$NHCONH$_2$, CH$_2$NHCONHR$^{11}$, CH$_2$NHCON(R$^{11}$)$_2$, CH$_2$NHSO$_2$R$^{11}$, CH$_2$PO$_3$H$_2$)

The free hydroxyl groups of compound 2a-c (Sakurai and Kahne 2010) (Scheme 6) are either benzylated or p-methoxybenzylated using NaH as base in THF or DMF. The products 3a-c are converted to acceptors 4a-c following reported procedures for the corresponding dibenzyl compounds (Plettenburg, Bodmer-Narkevitch et al. 2002; Lee, Farrand et al. 2006). PMB ether 4d is obtained from D-ribophytosphingosine as reported for the corresponding Bn ether (Trappeniers, Goormans et al. 2008; Baek, Seo et al. 2011). PMB ether 4e is obtained from sphingosine by a) conversion of the amino group to an azide with trifluoromethanesulfonyl azide; b) TBDPS-protection of the primary hydroxyl group; c) PMB-protection of the secondary hydroxyl group; d) desilylation. Glycosylation is effected using an appropriately protected glycosyl trichloroacetimidate donor (1.5 equiv) and TMSOTf (0.1 equiv) as activator in dry THF/ether. Appropriate protecting groups include benzyl and di-tert-butylsilylene. The azido group of 5a-e is reduced under Staudinger conditions (PMe$_3$, THF then aq NaOH) followed by amine-protection with Boc$_2$O in CH$_2$Cl$_2$. The PMB groups of 6a-e are cleaved with either CAN or DDQ in CH$_2$Cl$_2$-water and the free hydroxyl groups esterified with the appropriate carboxylic acid (R$^{12}$OH) in the presence of DCC, DMAP to give esters 7a-e. Cleavage of the di-tert-butylsilyl group with TBAF gives intermediates 8a-e which may be treated in various ways to provide compounds of formula (I″) with a variety of different R$^4$ groups. For example, hydrogenolysis followed by N-Boc deprotection gives compounds of formula (I″) where R$^4$ is CH$_2$OH. Alternatively, the primary hydroxyl group of 8 may be esterified, sulfated or phosphorylated, and subsequently deprotected in a similar fashion, to give compounds of formula (I″) where R$^4$ is CH$_2$OCOR$^{11}$, CH$_2$OSO$_3$H or CH$_2$OPO$_3$H$_2$. Conversion of the primary hydroxyl group of 8 to a leaving group (eg, iodide, tosylate) followed by nucleophilic displacement gives access into thioethers and related derivatives, amides, carbamates, ureas, N-sulfonates and phosphonates which, after removal of protecting groups, leads to further compounds of formula (I″).

Amines (I″) are further transformed into other compounds of the invention (shown as compounds of formula (I′) in General Method (3) according to the following general procedures:

General Method (3) for Synthesis of Compounds of Formula (I)

Scheme 7

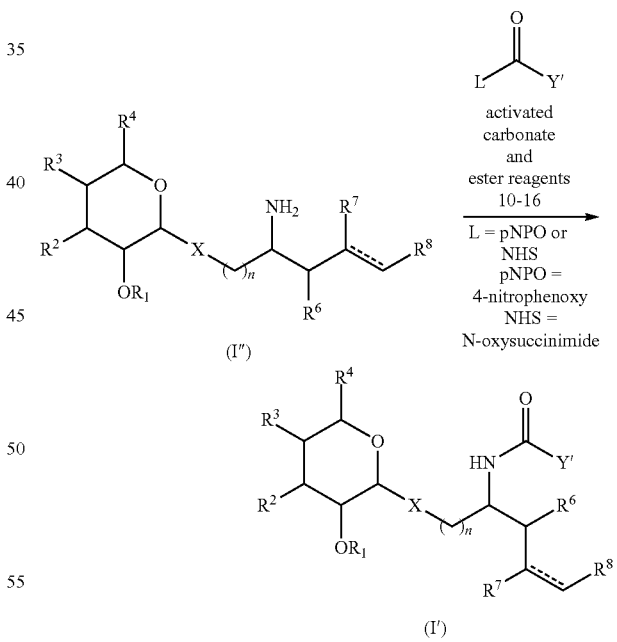

For the preparation of compounds of formula (I) where R$^5$ is a radical of formula (i) (Scheme 7), a mixture of amine (I″) (0.05-0.1 M), activated carbonate or ester 10-16 (where Y′ may be Y as defined herein for formula (I) or a protected form of Y) (1.05-2 equiv) and NEt$_3$ (0-2 equiv) are stirred in a suitable solvent (e.g. pyridine, pyridine-CHCl$_3$, CHCl$_3$-MeOH) at ambient temperature until the reaction is essentially complete (TLC). After concentration of the mixture, the residue is purified by column chromatography on silica gel. Any protecting groups in group Y are subsequently removed, by standard methods: Pd-catalyzed hydrogenolysis for phosphate benzyl esters and N-Cbz groups, TFA/CH$_2$Cl$_2$ for phosphate tert-butyl esters and N-Boc groups, piperidine for N-Fmoc groups and Zn/NH$_4$OCHO in MeOH/THF or MeOH/CH$_2$Cl$_2$ for trichloroethyl-protected sulfates (Ingram and Taylor 2006; Taylor and Desoky 2011). The deprotected products are purified by chromatography on silica gel or C18 silica gel.

Preparation of Reagents 10-16

Scheme 8

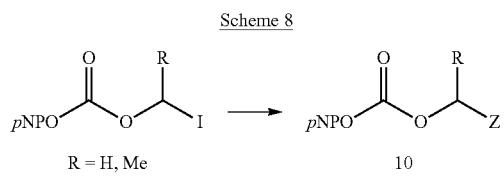

R = H, Me

Reagents 10 (Scheme 8) are prepared by reaction of iodomethyl 4-nitrophenyl carbonate (Gangwar, Pauletti et al. 1997) or α-chloroethyl 4-nitrophenyl carbonate (Alexander, Cargill et al. 1988) with the silver salt of either a carboxylic acid, a thioacid, or dibenzyl phosphate, in a suitable solvent (eg, dry MeCN or dry toluene), at a temperature between 20 and 80° C. The inclusion of 4 Å molecular sieves may be beneficial. After removal of silver salts by filtration, the product is purified by chromatography on silica gel. Where Z is an oxodioxolenyl group, reagents 10 are made according to literature procedures (Alexander, Bindra et al. 1996; Sun, Cheng et al. 2002).

Reagents 11 and 12 (Scheme 9) are synthesized in accordance with or by adapting literature procedures (Greenwald, Pendri et al. 1999). Generally, an appropriately substituted benzylic alcohol is reacted with p-nitrophenyl chloroformate in the presence of a suitable base (eg, pyridine, i-Pr$_2$NEt) in CH$_2$Cl$_2$. Alternatively, the benzylic alcohol is reacted with disuccinimidylcarbonate in the presence of pyridine. The benzylic alcohols may be commercially available or obtained by transformation of commercially available 2- or 4-hydroxybenzaldehydes or 2- or 4-hydroxybenzyl alcohols.

For example, for benzylic alcohols where Z is a N,N-dialkyl thiocarbamate (i.e. —SCON(A$^1$)$_2$), variously substituted 2- or 4-hydroxybenzaldehydes are converted to thiophenol derivatives according to literature procedures (Lin 2000) involving a) reaction of the phenol group with a N,N-dialkyl thiocarbamoyl chloride; b) reduction of the aldehyde with LiBH$_4$ in THF; c) heating in an ethereal solvent (e.g. Ph$_2$O, or bis(2-(2-methoxyethoxyl)ethyl) ether at 250° C. to effect Newman-Kwart rearrangement of the thiocarbamate functionality (see Scheme 10 below). Where Z is —SCONHA$^1$ or —SCOA$^1$, the rearranged thiocarbamates obtained above may be hydrolyzed with KOH to give the free thiophenol, which is either reacted with an isocyanate to provide N-monoalkyl thiocarbamates, (Gryko, Clausen et al. 1999) or acylated with an acid chloride and NEt$_3$ or with an acid in the presence of coupling reagents such as DCC, EDC to provide thioesters (see Scheme 10). These products are then converted to reagents 11 by activation of the benzylic hydroxyl group, as described above.

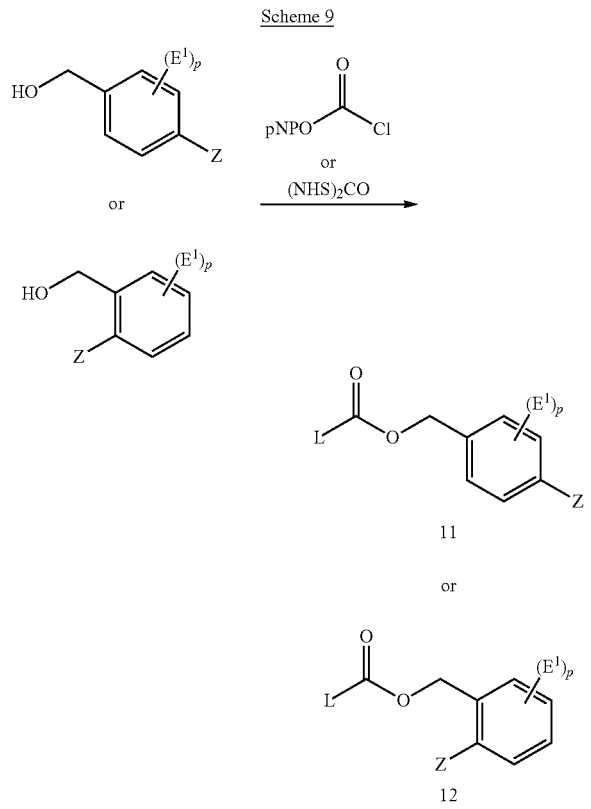

L = pNPO or NHS
pNP = 4-nitrophenyl
NHS = N-oxysuccinimide

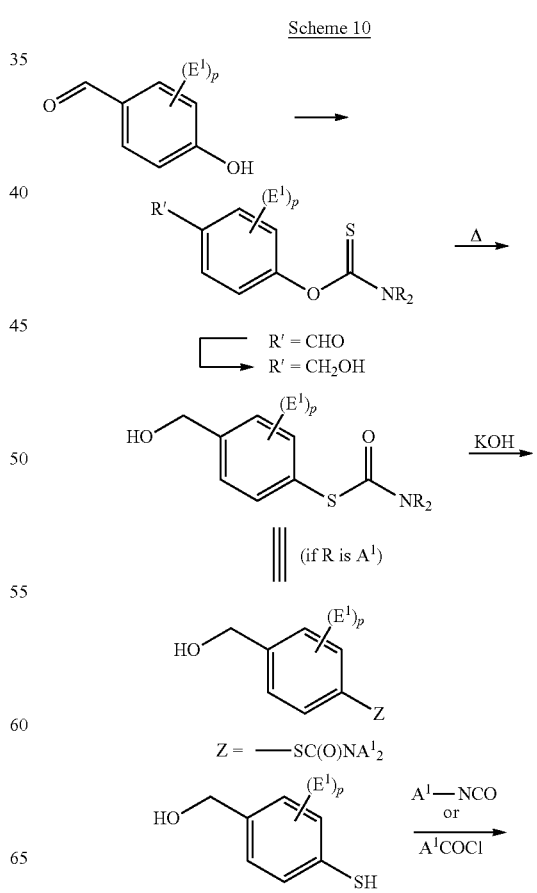

-continued

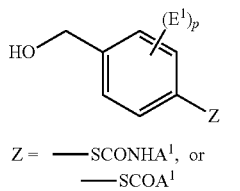

Z = —SCONHA$^1$, or
—SCOA$^1$

Where Z in reagents 11 and 12 is a phosphate, protected phosphotriesters of hydroxybenzyl alcohol are reported (Li, Luo et al. 1998).

Where Z in reagents 11 and 12 is —OCONA$^1_2$, these derivatives are obtained by reaction of hydroxybenzaldehyde derivatives with carbamoyl chloride reagents. Alternatively, these may be obtained by reaction of 1°-OH-protected hydroxybenzyl alcohol derivatives with a phosgene equivalent, such as 4-nitrophenyl chloroformate, followed by reaction with a secondary amine.

Where Z in reagents 11 and 12 is —OSO$_u$A$^1$, these derivatives are obtained by reaction of hydroxybenzaldehyde derivatives with a sulfinyl chloride, sulfonyl chloride or sulfonic anhydride.

Where Z in reagents 11 and 12 is —OSO$_3$H, these derivatives are obtained by sulfation of the phenolic O-atom of hydroxybenzyl alcohol or hydroxybenzaldehyde derivatives with a protected sulfating reagent (eg, Cl$_3$CCH$_2$OSO$_2$Cl or 2,2,2-trichloroethoxysulfuryl-N-methylimidazolium triflate) (Ingram and Taylor 2006; Taylor and Desoky 2011).

Reagents 13 and 14 are synthesized in accordance with or by adapting literature procedures, (Carpino, Triolo et al. 1989; Amsberry and Borchardt 1991; Amsberry, Gerstenberger et al. 1991; Nicolaou, Yuan et al. 1996; Greenwald, Choe et al. 2000) or by the following methods.

Scheme 11

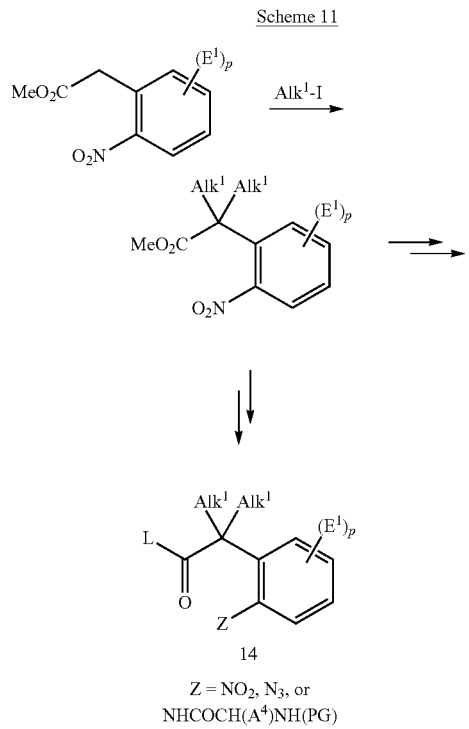

Z = NO$_2$, N$_3$, or
NHCOCH(A$^4$)NH(PG)

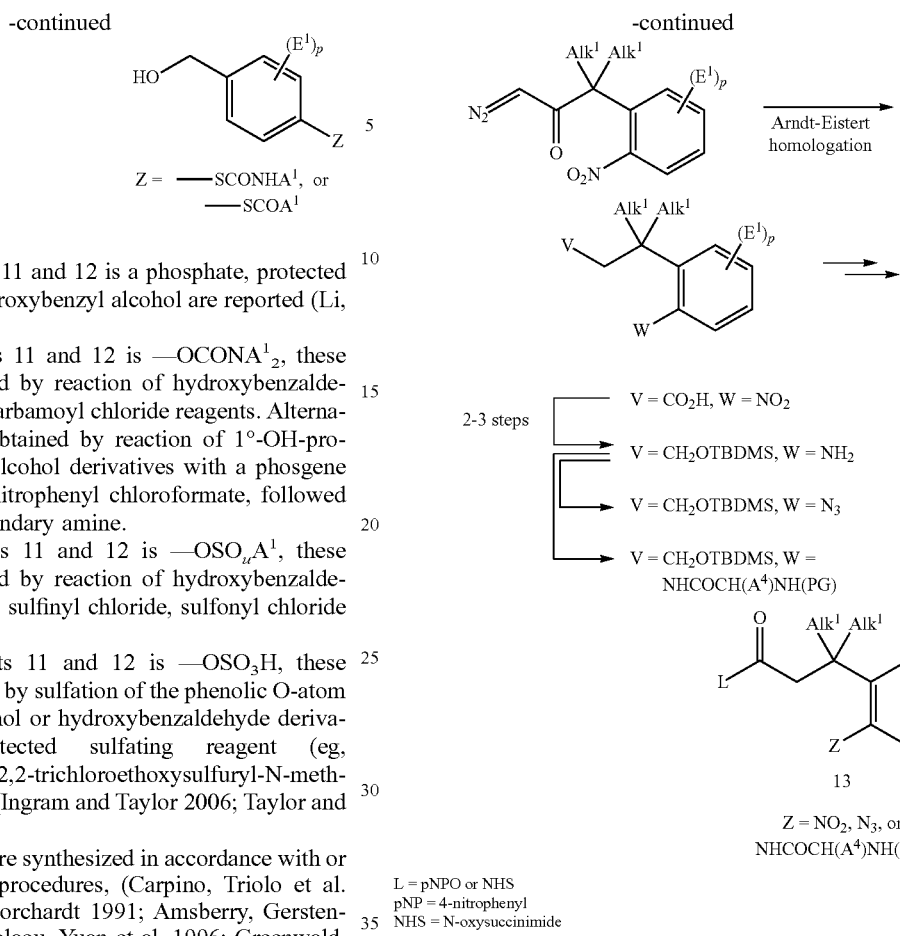

L = pNPO or NHS
pNP = 4-nitrophenyl
NHS = N-oxysuccinimide

Where Z is NO$_2$, N$_3$, or NHCOCH(A$^4$)NH$_2$, variously substituted 6-nitrophenylacetic acid esters (obtained from commercial sources, or by known procedures, or by Arndt-Eistert homologation of the corresponding 6-nitrobenzoic acid esters (Atwell, Sykes et al. 1994)) are gem-dialkylated with an alkyl iodide and a suitable base (eg, NaH, KO$^t$Bu, n-BuLi), optionally in the presence of 18-crown-6. The dialkylated product is, via the acid chloride, subjected to Arndt-Eistert homologation (CH$_2$N$_2$; then heat or Ag(II)). The nitro group may be transformed to an azide or a protected amino acid-amide via the amine (after temporary reduction of the carboxyl group to the alcohol oxidation level to prevent premature lactamization.) Suitable protecting groups (PG in Scheme 11) for amino acids are benzyloxycarbonyl (Cbz), fluorenylmethoxycarbonyl (Fmoc) t-butoxycarbonyl (Boc). These products are converted to activated esters 13 (L=pNPO or NHS) by standard means. Alternatively, after gem-dialkylation, a similar sequence of functional group transformations may be used to access activated esters 14.

Where Z in reagents 13 and 14 is —SCONA$^1_2$, —SCONHA$^1$, —SCOA$^1$, phosphate, —OCONA$^1_2$, OSO$_u$A$^1$ or OSO$_3$H, these compounds are derived from phenol derivatives XIII (Greenwald, Choe et al. 2000; Hillery and Cohen 1983) as described above for the preparation of reagents 11 and 12.

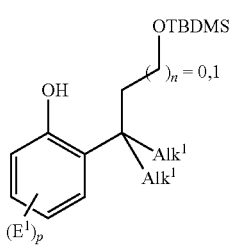

XIII

Activated esters 15 are prepared from the corresponding acids (Hillery and Cohen 1983; Carpino, Triolo et al. 1989; Amsberry and Borchardt 1991) by standard means.

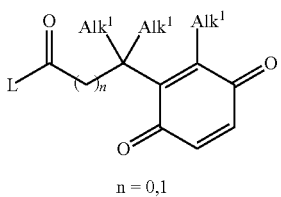

n = 0,1

L=pNPO or NHS
pNP=4-nitrophenyl
NHS=N-oxysuccinimide

Activated esters 16 are obtained by derivatization of phenol XIV, following literature procedures (Liao and Wang 1999) and/or in conjunction with chemistry described above.

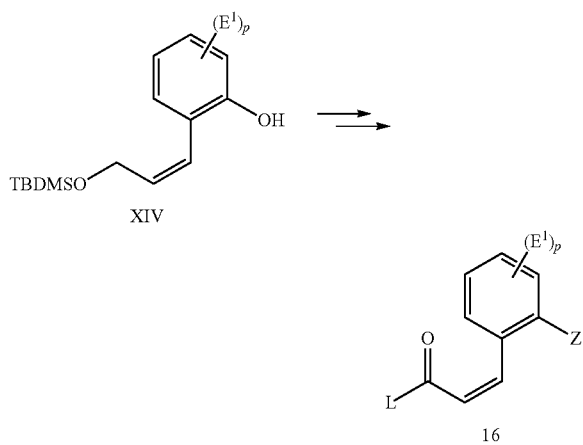

XIV

16

ABBREVIATIONS

Figure 1:
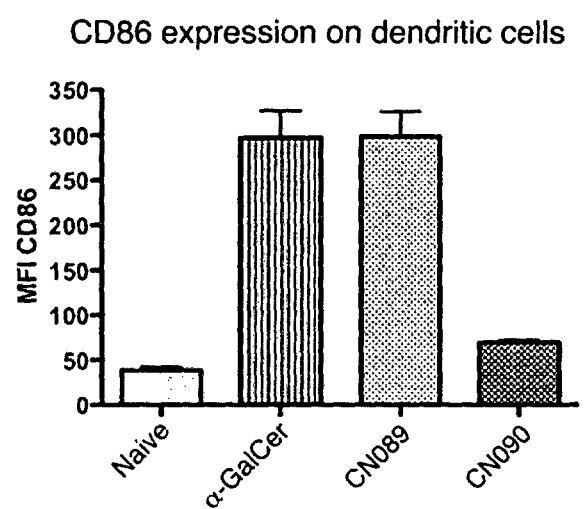
FIG. 1 shows CD86 expression on dendritic cells. The data show that injection of compounds of the invention induces activation of NKT cells and subsequent maturation of dendritic cells. Groups of C57BL/6 mice (n=3) are injected intravenously with 200 ng of the indicated compounds and then the spleens are removed 20 h later for the analysis of CD86 expression on CD11c+ dendritic cells by antibody labelling and flow cytometry. Mean fluorescence index±SEM are presented.
Figure 2:
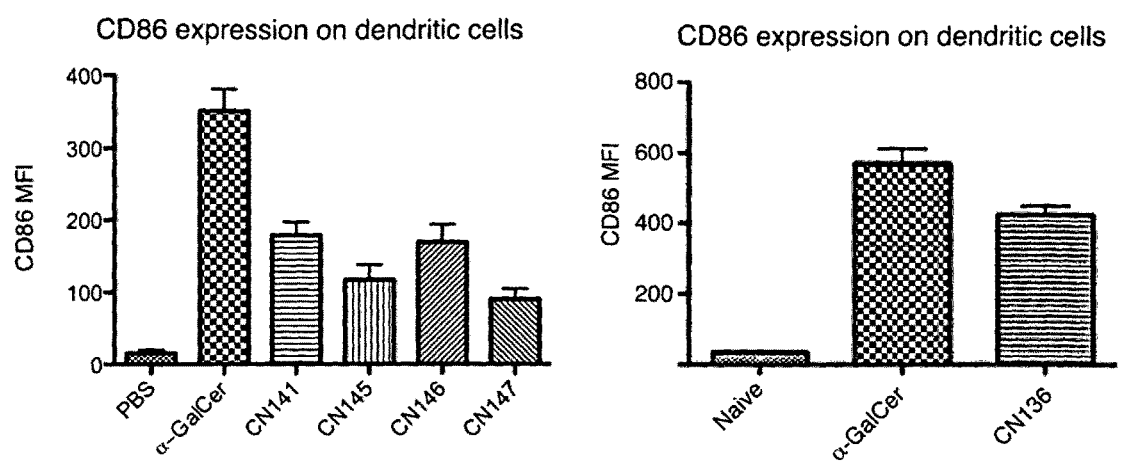
FIG. 2 shows CD86 expression on dendritic cells. The data show that injection of compounds of the invention induces activation of NKT cells and subsequent maturation of dendritic cells. Groups of C57BL/6 mice (n=3) are injected intravenously with 200 ng of the indicated compounds and then the spleens are removed 20 h later for the analysis of CD86 expression on CD11c+ dendritic cells by antibody labelling and flow cytometry. Mean fluorescence index±SEM are presented.
Figure 3:
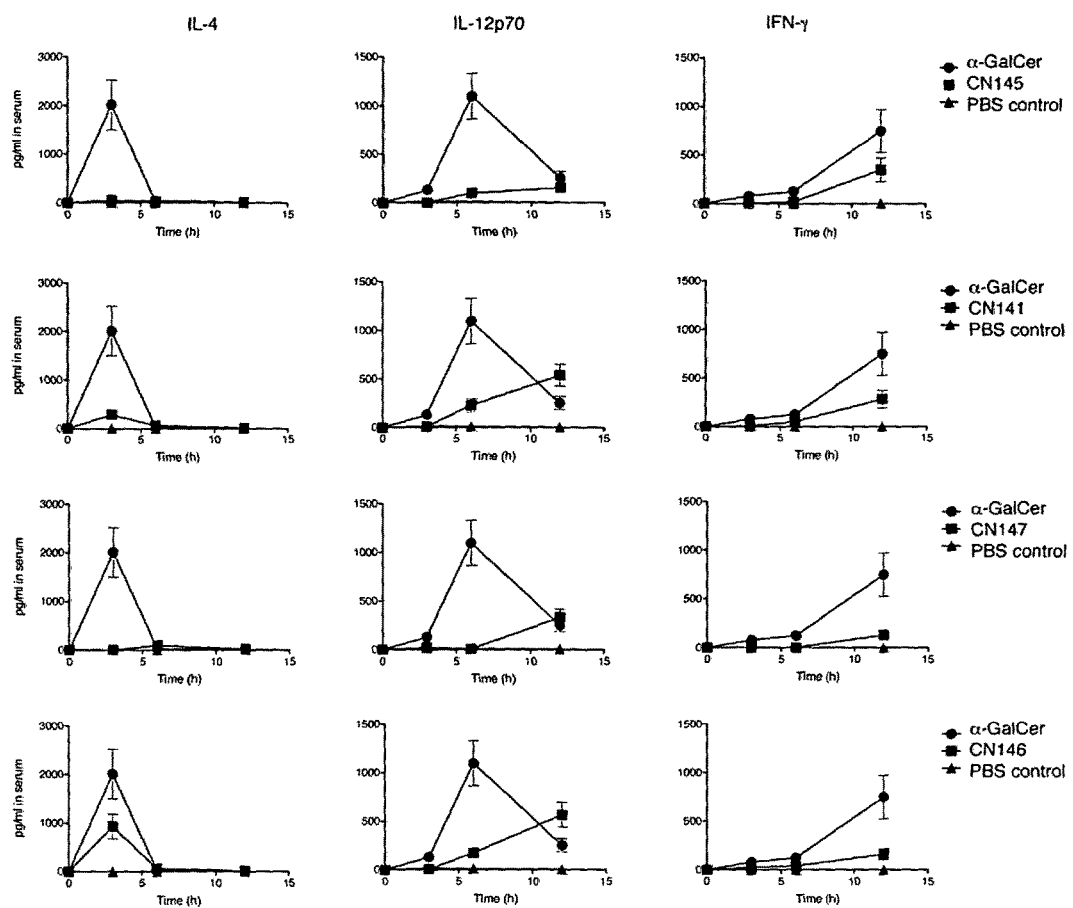
FIG. 3 shows kinetics of cytokine release into serum following the injection of compounds of the invention. Groups of C57BL/6 mice (n=3 per group) are injected intravenously with 200 ng of the indicated compounds, and then the serum is collected at the indicated times for analysis of cytokine levels by cytokine bead array technology.
Figure 4:
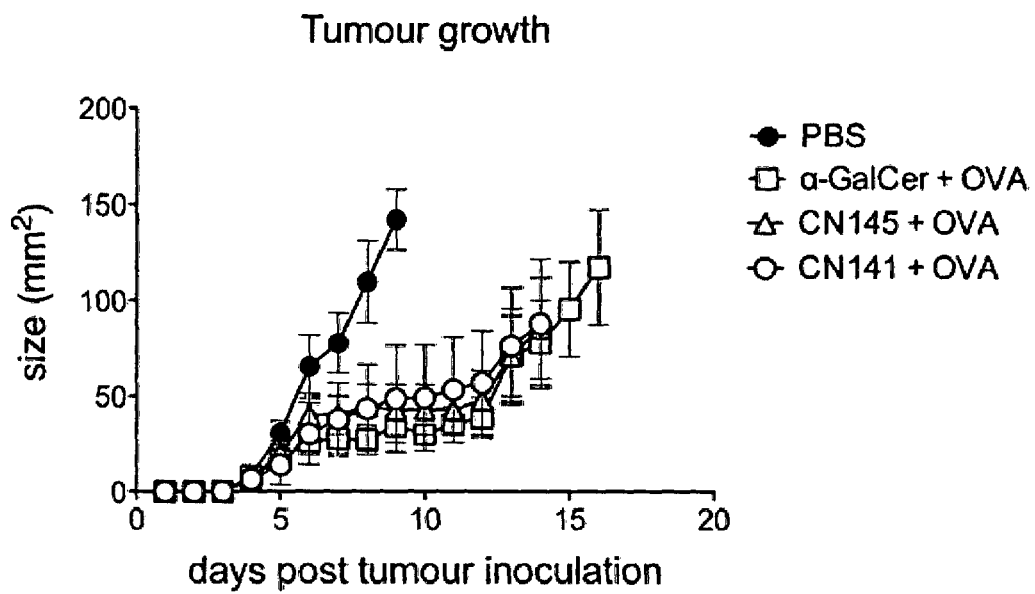
FIG. 4 shows the effect of compounds of the invention on tumour growth when administered together with a tumour-associated antigen. Progression of subcutaneous B16.OVA tumours is monitored in animals that are treated seven days after tumour challenge with intravenous OVA protein together with the indicated compounds, or treated with PBS. The mean tumour sizes per group (n=5)±SEM are shown. These data show that co-administration of compounds of the invention with tumour vaccine provides therapeutic anti-tumour activity.
Figure 5:
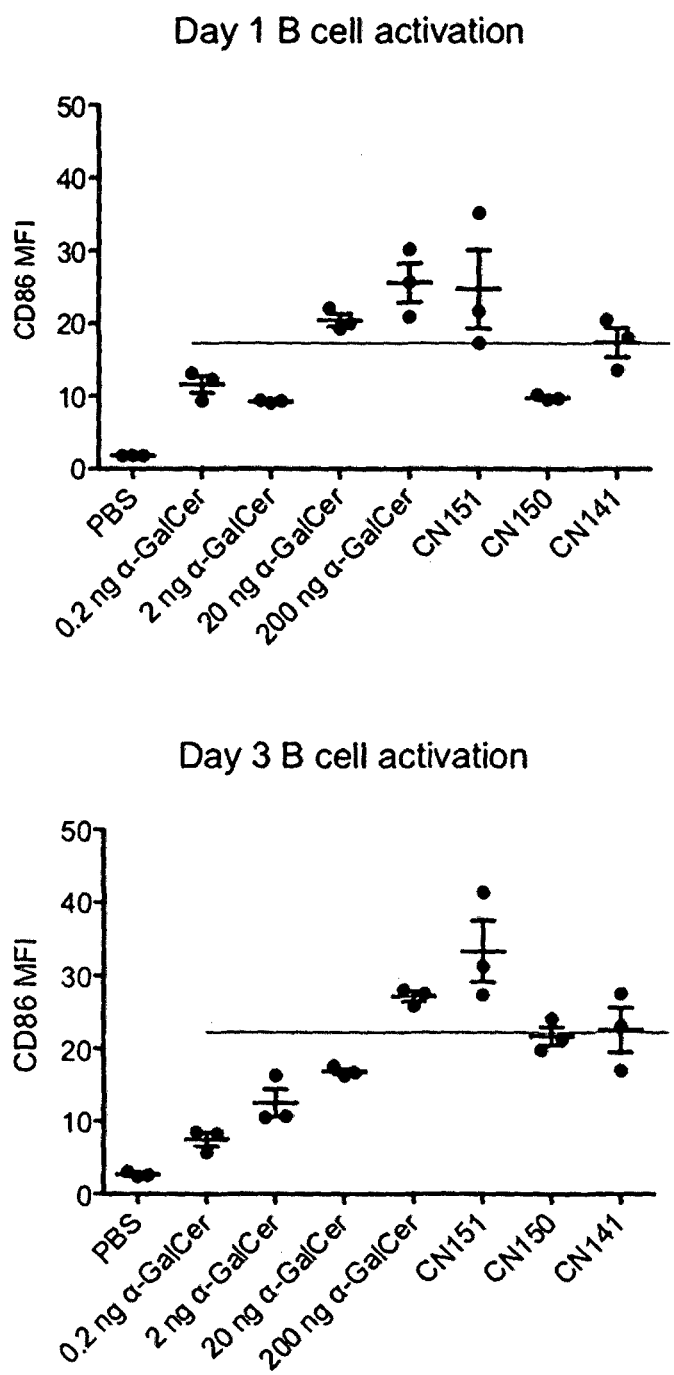
FIG. 5 shows the effect of administered compounds on maturation of splenic B cells as a measure of NKT cell activity. Groups of C57BL/6 mice (n=3) are injected intravenously with the indicated doses of α-GalCer (αGC), or 200 ng of the indicated compounds, and spleens are removed 20 h after injection for analysis by flow cytometry. B cells are identified on the basis of binding of fluorescent antibodies specific for the pan-B cell marker, CD45R. The mean fluorescence index (MFI) of antibody binding to the cell-surface maturation marker CD86 on B cells is shown.
Figure 6:
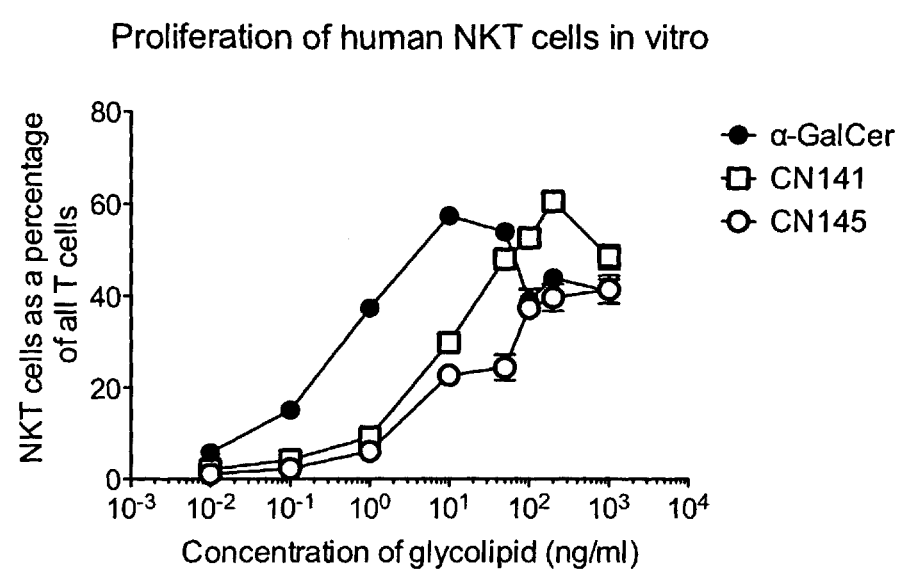
FIG. 6 shows the effect of compounds of the invention on proliferation of human NKT cells. PBMC from one donor are cultured for 7 days with different doses of the indicated compounds in the presence of IL-2, and then the percentages of NKT cells in the final cultures determined by flow cytometry with fluorescent α-GalCer-loaded CD1d tetramers and anti-CD3. Data are expressed as percentage of NKT cells (α-GalCer/CD1d tetramer and anti-CD3-binding cells) of total T cells (all anti-CD3-binding cells).
Figure 7:
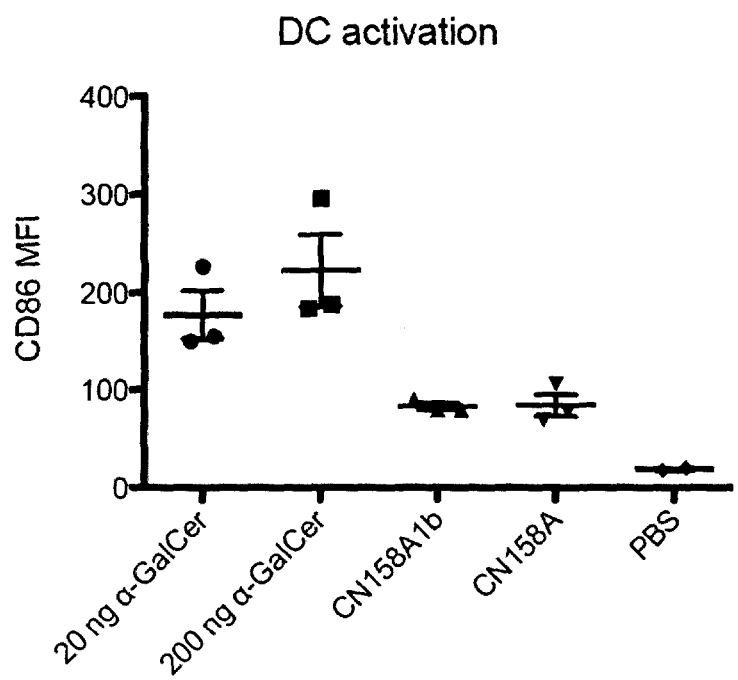
FIG. 7 shows CD86 expression on dendritic cells. The data show that injection of compounds of the invention induces activation of NKT cells and subsequent maturation of dendritic cells. Groups of C57BL/6 mice (n=3) are injected intravenously with 200 ng of α-GalCer or an equivalent molar amount of the indicated compounds and then the spleens are removed 20 h later for the analysis of CD86 expression on CD11c+ dendritic cells by antibody labelling and flow cytometry. Mean fluorescence index±SEM are presented. (Compound CN158A1b=CN158 formulated in accordance with Example 15. Compound CN158A=CN158 in water.)
Figure 8:
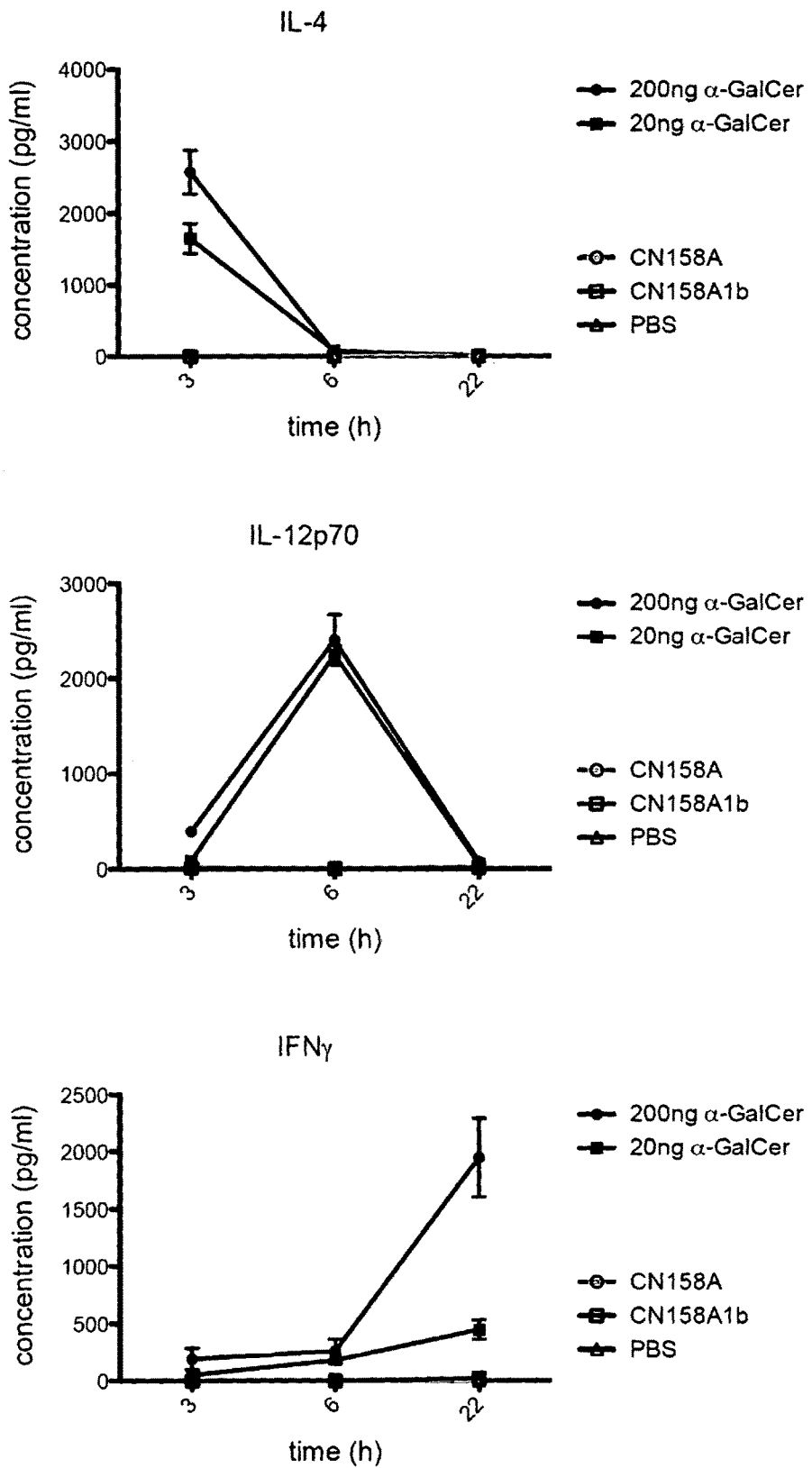
FIG. 8 shows kinetics of cytokine release into serum following the injection of α-GalCer. No detectable cytokines are observed for CN158, a compound of the invention. Groups of C57BL/6 mice (n=3 per group) are injected intravenously with 200 ng of α-GalCer or an equivalent molar amount of the indicated compounds, and then the serum is collected at the indicated times for analysis of cytokine levels by cytokine bead array technology. (Compound CN158A1b=CN158 formulated in accordance with Example 15; Compound CN158A=CN158 in water.)
Figure 9:
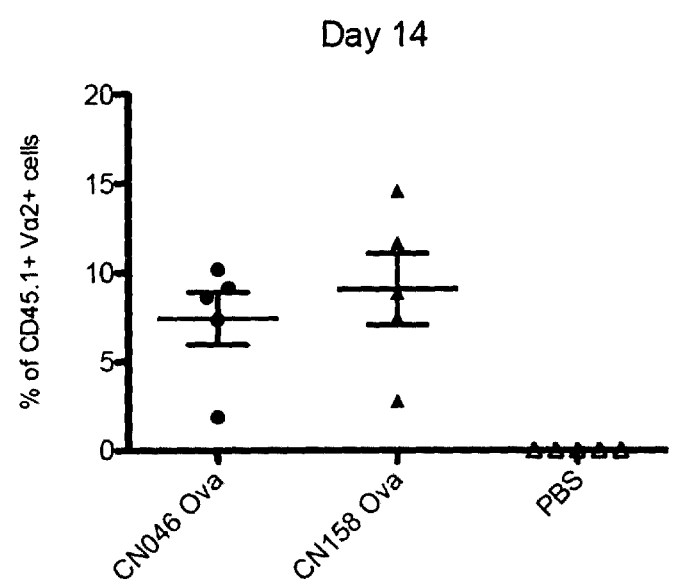
FIG. 9 shows enumeration of T cells with specificity for the peptide antigen SIINFEKL following intravenous administration of compounds of the invention as adjuvants into mice. The compounds are injected to give the equivalent molar dose as compared to α-GalCer. To increase sensitivity of the assay, all mice are initially donated a cohort of 10,000 SIINFEKL-specific T cells from a transgenic mouse encoding a T cell receptor for this antigen (OT-1 mice), which is undertaken by intravenous injection of the cells one day before the vaccines are administered. To discriminate the donated T cells from those of the host, the donated cells exhibit congenic expression of the CD45.1 variant of the CD45 molecule. It is therefore possible to enumerate SIINFEKL-specific T cells in blood by flow cytometry using antibodies for CD45.1 together with antibodies for the transgenic T cell receptor (Vα2). The data show that injection of α-GalCer together with a protein antigen OVA induces a population of SIINFEKL-specific T cells and that injection of compound of the invention CN158 together with OVA induces a similar T cell expansion. Control animals are injected with the diluent phosphate-buffered saline (PBS). Each dot represents a different animal; mean per treatment group±SEM are presented. *p<0.001,  p<0.01, * p<0.05.
Figure 10:
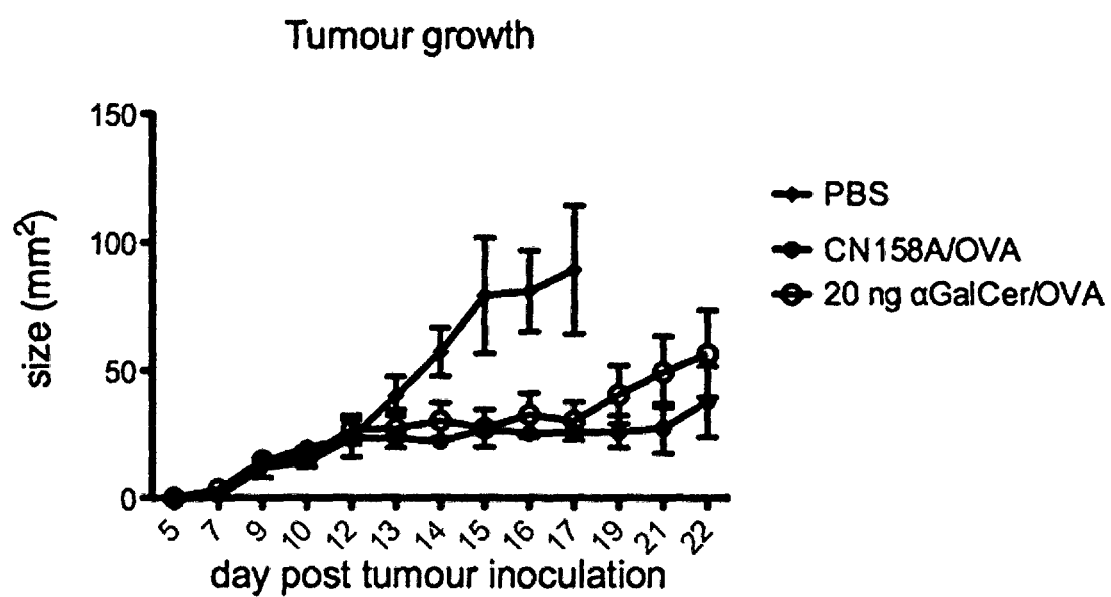
FIG. 10 shows the effect of compounds of the invention on tumour growth when administered together with a tumour-associated antigen. Progression of subcutaneous B16.OVA tumours is monitored in animals that are treated seven days after tumour challenge with intravenous OVA protein together with the indicated compounds, or treated with PBS. The mean tumour sizes per group (n=5)±SEM are shown. These data show that co-administration of compounds of the invention (CN158) or the molar equivalent of α-GalCer with tumour-associated antigen provides therapeutic anti-tumour activity. (Compound CN158A=CN158 in water.)

NMR Nuclear magnetic resonance spectrometry
HRMS High resolution mass spectrometry
ESI Electrospray ionisation
Cbz Benzyloxycarbonyl
RT Room temperature
THF Tetrahydrofuran
PBS Phosphate-buffered saline
HPLC High performance liquid chromatography
FCS Fetal calf serum
MS Mass spectrometry
TFA Trifluoroacetic acid
TLC Thin layer chromatography
DMF Dimethylformamide
DCC N,N'-dicyclohexylcarbodiimide
NHS N-oxysuccinimide

EXAMPLES

The examples described herein are for purposes of illustrating embodiments of the invention. Other embodiments, methods, and types of analyses are within the capabilities of persons of ordinary skill in the art and need not be described in detail herein. Other embodiments within the scope of the art are considered to be part of this invention.

Anhydrous solvents are obtained commercially. Air sensitive reactions are carried out under Ar. Thin layer chromatography (TLC) is performed on aluminium sheets coated with 60 $F_{254}$ silica. Flash column chromatography is performed on Merck or SiliCycle silica gel (40-63 μm) or SiliCycle reversed phase (C18) silica gel (40-63 μm). NMR spectra are recorded on a Bruker 500 MHz spectrometer. $^1$H NMR spectra are referenced to tetramethylsilane at 0 ppm (internal standard) or to residual solvent peak ($CHCl_3$ 7.26 ppm, $CHD_2OD$ 3.31 ppm). $^{13}$C NMR spectra are referenced to tetramethylsilane at 0 ppm (internal standard) or to the deuterated solvent peak ($CDCl_3$ 77.0 ppm, $CD_3OD$ 49.0 ppm). $CDCl_3$—$CD_3OD$ solvent mixtures are always referenced to the methanol peak. High resolution electrospray ionization mass spectra are recorded on a Q-Tof Premier mass spectrometer.

Example 1

Synthesis of (2S,3S,4R)-2-Amino-1-O-α-D-galactopyranosyl-4-O-hexacosanoyl octadecane-1,3,4-triol (CN089)

Example 1.1

Synthesis of (2S,3S,4R)-2-Azido-3,4-O-dibenzyl-1-O-α-D-galactopyranosyl octadec-6-ene-1,3,4-triol (18)

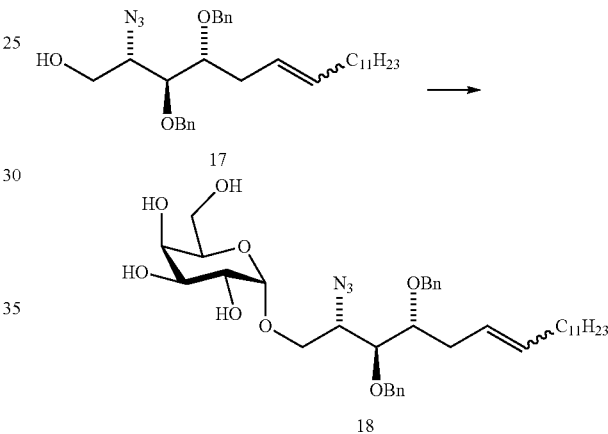

To an ice-cooled solution of per(trimethylsilyl)galactose (Bhat and Gervay-Hague 2001) (1.44 g, 2.66 mmol) in dry $CH_2Cl_2$ (13 mL) is added TMSI (0.34 mL, 2.5 mmol) dropwise. The mixture is stirred at 0° C. for 40 min, then at rt for 10 min, before being transferred to a flask containing $Bu_4NI$ (2.9 mg, 7.9 mmol), i-$Pr_2NEt$ (0.90 mL, 5.2 mmol), 4 Å molecular sieves (200 mg) and acceptor 17 (442 mg, 0.847 mmol) in $CH_2Cl_2$ (12 mL). The reaction is stirred under Ar at rt for 24 h before quenching with methanol (0.3 mL, 3 h) to destroy any remaining galactosyl iodide. After diluting with petroleum ether (100 mL) and filtration through celite, the filtrate is washed with 10% aq $NaS_2O_3$, brine, dried ($MgSO_4$), and concentrated to afford a yellow oil (1.7 g). The silyl groups are removed by stirring at rt with DOWEX 50 WX8-200 resin (200 mg) in 5:1 MeOH—$CH_2Cl_2$ (36 mL) for 60 min, before filtering and concentrating under reduced pressure to give a yellow solid (926 mg). Flash chromatography on silica gel, (5% to 15% i-PrOH/$CH_2Cl_2$), gives unreacted acceptor 17 (54 mg, 90% pure, 11%) followed by 18 as an E/Z mixture (381 mg, 66%). Data for the Z-isomer: $^1$H NMR (500 MHz, $CDCl_3$) δ 0.88 (t, J=7.0 Hz, 3H), 1.24-1.35 (m, 18H), 2.00-2.04 (m, 2H), 2.42-2.47 (m, 3H), 2.56 (br, 1H), 3.25 (br, 1H), 3.39 (br, 1H), 3.61-3.72 (m, 6H), 3.78-3.83 (m, 2H), 3.86-3.89 (m, 1H), 4.02 (d, J=2.7 Hz, 1H), 4.06 (dd, J=2.5, 10.6 Hz, 1H), 4.51 (d, J=11.6 Hz, 1H), 4.61-4.66 (m, 3H), 4.89 (d, J=3.7

Hz, 1H), 5.43-5.54 (m, 2H), 7.26-7.35 (m, 10H); $^{13}$C NMR (126 MHz, CDCl$_3$) δ 14.1, 22.7, 27.6, 28.0, 29.3, 29.4, 29.54, 29.56, 29.63, 29.7, 31.9, 62.3, 62.9, 69.1, 69.3, 69.9, 70.3, 70.8, 72.0, 73.9, 78.7, 79.9, 99.5 ($^{1}J_{CH}$=170 Hz), 124.3, 127.7, 127.9, 128.0, 128.40, 128.44, 132.8, 137.7, 138.1; HRMS-ESI m/z calculated for C$_{38}$H$_{57}$N$_3$O$_8$Na [M+Na]$^+$ 706.4043. found 706.4034.

Example 1.2

Synthesis of (2S,3S,4R)-3,4-O-Dibenzyl-1-O-α-D-galactopyranosyl-2-hexacosanoylamino octadec-6-ene-1,3,4-triol (1)

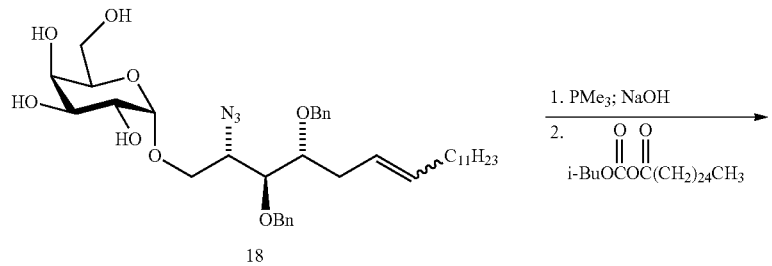

A solution of azide 18 (267 mg, 0.39 mmol) in 10:1 THF-water (11 mL) is stirred with PMe$_3$ (1 M solution in THF, 1.95 mL, 1.95 mmol) at 0° C. for 45 min then at rt for 2 h, before adding 1 M NaOH solution (3.9 mL). After stirring the biphasic mixture at rt for 2 h, the reaction is quenched with EtOAc (4 mL) and left at rt overnight. The reaction mixture is partitioned between water and CH$_2$Cl$_2$ and the product is thoroughly extracted into the organic phase, dried (MgSO$_4$), and concentrated under reduced pressure to give the crude amine product (310 mg). In a separate flask, isobutyl chloroformate (68 µl, 0.52 mmol) is added to a mixture of hexacosanoic acid (205 mg, 0.517 mmol) and NEt$_3$ (0.10 mL, 0.72 mmol) in dry CH$_2$Cl$_2$ (5 mL), and stirred for 35 min at rt before cooling in ice and transferring to an ice-cooled solution of the above amine in CH$_2$Cl$_2$ (4 mL). The reaction is stirred for 25 min and quenched with saturated aq NaHCO$_3$ (20 mL, 5 min) before extracting the product with CH$_2$Cl$_2$. At this point, Et$_2$NH (0.5 mL) is added to the organic extracts to destroy excess activated ester. The solution is dried (MgSO$_4$) and concentrated under reduced pressure to give the crude material (506 mg). Flash chromatography on silica gel (6% to 8% i-PrOH/CH$_2$Cl$_2$) gives amide 1 (323 mg, 80% yield). Data for the Z-isomer: $^1$H NMR (500 MHz, CDCl$_3$) δ 0.86-0.89 (m, 6H), 1.22-1.36 (m, 62H), 1.42-1.48 (m, 2H), 1.82-1.95 (m, 2H), 2.01-2.06 (m, 2H), 2.41-2.46 (m, 1H), 2.48-2.54 (m, 1H), 2.70 (br, 1H), 2.81 (br, 1H), 3.17 (br, 2H), 3.58-3.74 (m, 7H), 3.81 (dd, J=5.2, 11.3 Hz, 1H), 3.94 (dd, J=3.4, 10.9 Hz, 1H), 3.98 (d, J=2.8 Hz, 1H), 4.42-4.52 (m, 3H), 4.64-4.67 (m, 2H), 4.81 (d, J=3.7 Hz, 1H), 5.44-5.55 (m, 2H), 5.74 (d, J=9.3 Hz, 1H), 7.27-7.37 (m, 10H); $^{13}$C NMR (126 MHz, CDCl$_3$) δ 14.1, 22.7, 25.7, 27.6, 28.0, 29.3, 29.4, 29.6, 29.7, 31.9, 36.8, 50.0, 62.9, 69.4, 69.7, 70.0, 70.2, 71.0, 71.6, 73.1, 78.4, 80.6, 100.2, 124.3, 127.9, 128.0, 128.1, 128.2, 128.5, 128.7, 132.9, 137.97, 138.00, 173.5; HRMS-ESI m/z calculated for C$_{64}$H$_{109}$NO$_9$Na [M+Na]$^+$ 1058.8000. found 1058.8009.

Example 1.3

Synthesis of (2S,3S,4R)-2-Amino-1-O-α-D-galactopyranosyl-4-O-hexacosanoyl octadecane-1,3,4-triol (CN089) Via Hydrogenolysis of Compound 1

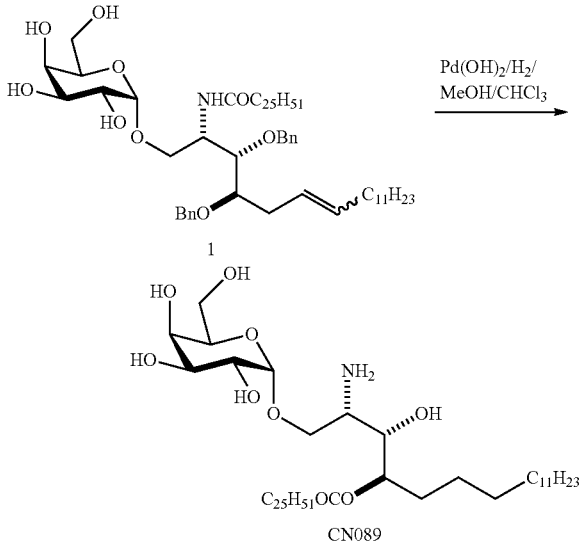

A mixture of compound 1 (324 mg, 0.303 mmol) and 20% Pd(OH)$_2$/C (300 mg) in 3:7 CHCl$_3$/MeOH (30 mL) is stirred under a hydrogen balloon at 35° C. for 21 h. The mixture is filtered through celite, washing with 3:1 CHCl$_3$/MeOH (2×100 mL), and the filtrate is concentrated. The crude residue is purified by silica gel chromatography (1:4 i-PrOH/CHCl$_3$ then 1:4 EtOH/CHCl$_3$) to afford the title compound CN089 (45 mg, 17%) as a white solid. $^1$H NMR (500 MHz, CDCl$_3$/CD$_3$OD 1:1) δ 0.87-0.90 (m, 6H), 1.29-1.36 (m, 68H), 1.56-1.67 (m, 3H), 1.81 (m, 1H), 2.34-2.37 (m, 2H), 3.23 (m, 1H), 3.52 (dd, J=9.1, 10.5 Hz, 1H), 3.70-3.85 (m, 7H), 3.97 (br d, J=3.5 Hz, 1H), 4.87 (d, J=3.8 Hz, 1H), 4.92 (dt, J=2.9, 9.0 Hz, 1H); $^{13}$C NMR (126 MHz, CDCl$_3$/CD$_3$OD 1:1) δ 14.4, 23.3, 25.6, 25.8, 29.8, 30.0, 30.3, 31.8, 32.6, 35.0, 53.7, 62.4, 65.0, 69.6, 70.4, 70.7, 71.5, 71.8, 73.8, 100.4, 174.8; HRMS-ESI calculated for C$_{50}$H$_{100}$NO$_9$ [M+H]$^+$ 858.7398. found 858.7396.

Example 1.4

Synthesis of (2S,3S,4R)-2-Amino-1-O-α-D-galactopyranosyl-4-O-hexacosanoyl octadecane-1,3,4-triol (CN089) Via Isomerization of α-GalCer

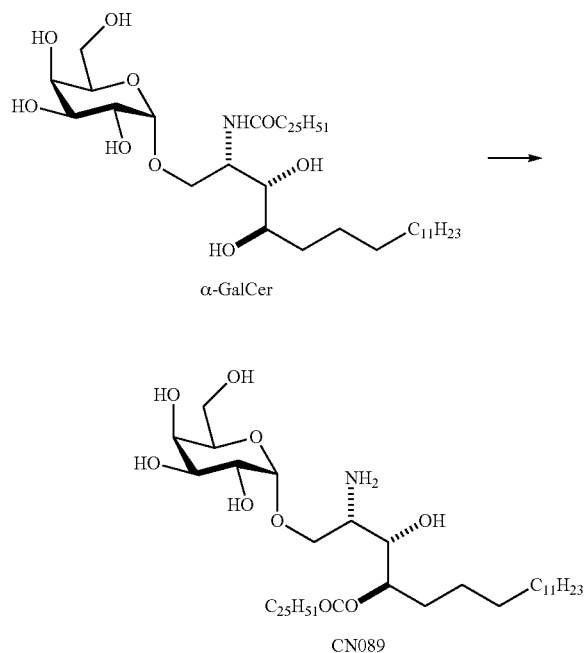

A solution of α-GalCer (80 mg, 0.093 mmol) in 1,4-dioxane-water (10:1, 16 mL) is warmed to 80° C. before the addition of 1 M HCl (2.96 mL). The solution is heated at 90° C. for 45 min then lyophilized to give a white solid. The crude residue is purified on silica gel (MeOH/CHCl$_3$=0:10 to 2:3) to afford the title compound CN089 as a white solid (50.5 mg, 63%).

Example 2

Synthesis of (2S,3S,4R)-1-O-α-D-Galactopyranosyl-4-O-hexacosanoyl-2-phosphoryloxymethoxycarbonylamino octadecane-1,3,4-triol (CN131)

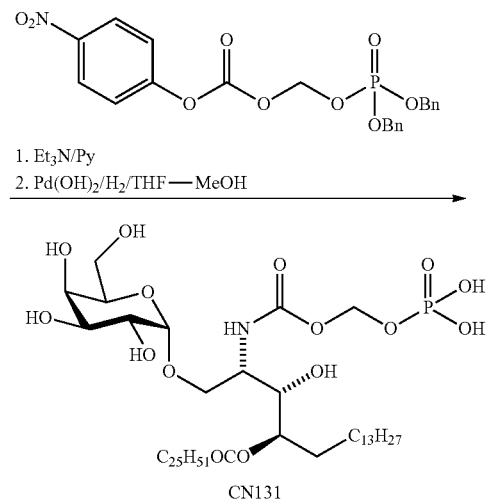

Example 2.1

(Bis(benzyloxy)phosphoryloxy)methyl 4-nitrophenyl carbonate

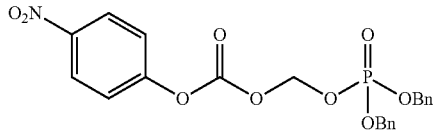 [SMILES: O=C(OCOP(=O)(OCc1ccccc1)OCc1ccccc1)Oc1ccc([N+](=O)[O-])cc1]

Silver(I) oxide (0.770 g, 3.32 mmol) is added to a solution of chloromethyl 4-nitrophenyl carbonate (Alexander, Cargill et al. 1988) (0.70 g, 3.02 mmol) and dibenzyl phosphate (0.925 g, 3.32 mmol) in anhydrous MeCN (30 mL) under Ar. The reaction is stirred at reflux for 18 h. The cooled mixture is diluted with EtOAc (30 mL), filtered through Celite and the solvent removed. The crude residue is purified by column chromatography on silica gel (EtOAc/pet. ether=1:4 to 1:1) to afford the title compound (0.12 g, 9%) as a colourless oil. $^1$H NMR (500 MHz, CDCl$_3$) δ 5.12 (m, 4H), 5.71 (d, J=14 Hz, 2H), 7.27 (m, 4H), 7.34 (m, 6H), 8.24 (d, J=9 Hz, 2H). $^{13}$C NMR (125 MHz) δ 69.3, 69.9, 70.0, 86.1, 86.2, 121.7, 125.3, 128.0, 128.7, 128.8, 135.18, 135.24, 145.7, 151.2, 154.9. $^{31}$P NMR (202 MHz) δ −2.5. HRMS-ESI [M+Na]$^+$ calcd for C$_{22}$H$_{20}$NNaO$_9$P: 496.0773. Found 496.0765.

Example 2.2

(2S,3S,4R)-1-O-α-D-Galactopyranosyl-4-O-hexacosanoyl-2-phosphoryloxymethoxycarbonylamino octadecane-1,3,4-triol (CN131)

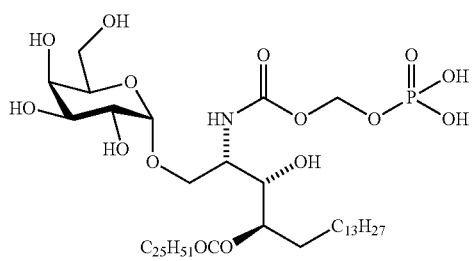

CN131

A solution of (bis(benzyloxy)phosphoryloxy)methyl 4-nitrophenyl carbonate (0.055 g, 0.117 mmol) in CH$_2$Cl$_2$ (10 mL) is added to the amine CN089 (0.050 g, 0.058 mmol) in pyridine (10 mL). Triethylamine (10 mL) is added and the reaction is stirred for 1 h. The mixture is quenched with MeOH (30 mL) then diluted with CHCl$_3$ (20 mL) and the solvents removed. The crude residue is purified on silica gel (MeOH/CHCl$_3$=0:1 to 2:3) to afford a sample of the benzylated phosphate. Pd(OH)$_2$ (20% on C, 30 mg) is added to a stirred solution of the intermediate (0.032 g, 0.027 mmol) in THF/MeOH (1:1, 10 mL). The solution is stirred under an atmosphere of hydrogen for 1 h. The mixture is filtered through Celite and the solvent removed. The crude residue is purified on silica gel (MeOH/CHCl$_3$/H$_2$O=40:70:0 to 40:70:6) to afford the title compound CN131 (0.023 g, 39%) as a white solid. $^1$H NMR (500 MHz, CDCl$_3$/CD$_3$OD/D$_2$O 70:40:6) δ 0.89 (m, 6H), 1.20-129 (m, 68H), 1.58-1.67 (m, 4H), 2.37 (m, 2H), 3.63 (m, 1H), 3.76-3.86 (m, 7H), 3.93 (m, 1H), 3.97 (m, 1H), 4.85 (d, J=2.5 Hz, 1H), 4.95 (m, 1H), 5.29 (m, 1H), 5.67 (m, 1H). $^{13}$C NMR (125 MHz) δ 15.2, 24.0, 26.5, 26.7, 30.1, 30.5, 30.65, 30.68, 30.8, 30.96, 31.03, 33.2, 35.9, 53.7, 62.6, 68.2, 70.2, 71.0, 72.2, 73.0, 75.9, 84.7, 100.7, 157.5, 176.0. $^{31}$P NMR (202 MHz) δ −0.7. HRMS-ESI [M−H]$^-$ calcd for C$_{52}$H$_{101}$NO$_{15}$P: 1010.6909. Found 1010.6915.

Example 3

(2S,3S,4R)-2-Acetoxymethoxycarbonylamino-1-O-α-D-galactopyranosyl-4-O-hexacosanoyl octadecane-1,3,4-triol (CN136)

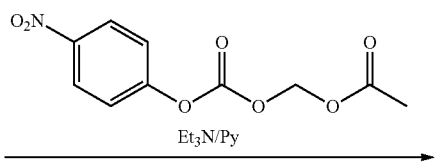

CN089 —Et$_3$N/Py→

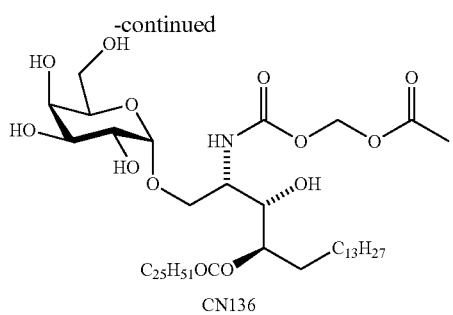

CN136

(4-Nitrophenoxy)carbonyloxymethyl acetate (Lin, Bitha et al. 1997) (0.050 g, 0.200 mmol) is added to the amine CN089 (0.025 g, 0.029 mmol) in pyridine (3 mL). Triethylamine (1 mL) is added and the reaction is stirred for 1 h. The mixture is quenched with MeOH (30 mL) then diluted with CHCl$_3$ (20 mL) and the solvents removed. The crude residue is purified on silica gel (MeOH/CHCl$_3$=0:1 to 3:7). The sample is further purified on RP-C18 (MeOH/CHCl$_3$=1:0 to 6:4) to afford the titled compound CN136 (0.019 g, 70%) as a white solid. $^1$H NMR (500 MHz, CDCl$_3$/CD$_3$OD 3:1) δ 0.84 (m, 6H), 1.18-1.27 (m, 68H), 1.57-1.65 (m, 4H), 2.07 (s, 3H), 2.31 (m, 2H), 3.66-3.74 (m, 8H), 3.82 (m, 1H), 3.89 (m, 1H), 4.82 (d, J=2.5 Hz, 1H), 4.89 (m, 1H), 5.68 (m, 2H). $^{13}$C NMR (125 MHz) δ 13.9, 20.5, 22.6, 25.0, 25.3, 28.7, 29.1, 29.2, 29.25, 29.27, 29.33, 29.4, 29.50, 29.54, 29.58, 29.61, 31.8, 34.5, 52.0, 61.8, 67.6, 69.0, 69.7, 70.2, 70.5, 71.5, 74.5, 80.0, 99.7, 154.8, 170.4, 174.5. HRMS-ESI [M+Na]$^+$ calcd for C$_{54}$H$_{103}$NNaO$_{13}$: 996.7322. Found 996.7295.

Example 4

(2S,3S,4R)-1-O-α-D-Galactopyranosyl-4-O-hexacosanoyl-2-(pivaloyloxymethoxycarbonylamino) octadecane-1,3,4-triol (CN145)

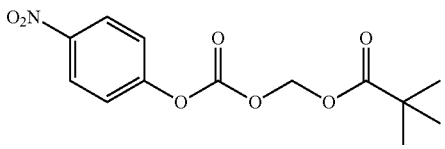

CN089 —Et$_3$N/Py→

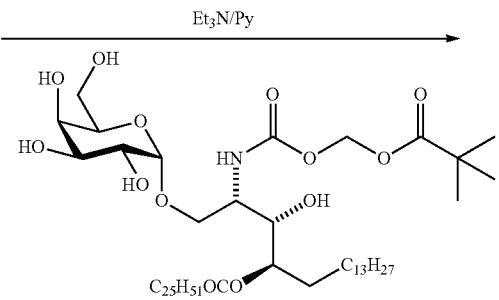

CN145

To a mixture of amine CN089 (28.4 mg, 0.033 mmol) in dry pyridine (0.33 mL) is added a solution of (4-nitrophenoxy)carbonyloxymethyl pivalate (Lin, Bitha et al. 1997) (11 mg, 0.037 mmol) in CHCl$_3$ (0.20 mL) followed by NEt$_3$ (8 μL, 0.057 mmol). After 1.5 h at rt the volatiles are concentrated under reduced pressure. The crude residue is purified by silica gel chromatography (1% to 7% MeOH/CHCl$_3$) to give a product-containing fraction which is further purified by automated flash chromatography on silica gel (1% to 8% MeOH/CHCl$_3$) to afford the title compound CN145 (14.4 mg, 43%) as a white solid. $^1$H NMR (500 MHz, 1:1 CDCl$_3$/CD$_3$OD) δ 0.87-0.90 (m, 6H), 1.22 (s, 9H), 1.24-1.43 (m, 68H), 1.59-1.75 (m, 4H), 2.31-2.41 (m, 2H), 3.71-3.86 (m, 9H), 3.95 (br, 1H), 4.86 (d, J=3.4 Hz, 1H) 4.92-5.00 (m, 1H), 5.70-5.80 (m, 2H); $^{13}$C NMR (126 MHz, 3:1 CDCl$_3$/CD$_3$OD) δ 14.1, 22.9, 25.3, 25.7, 26.9, 28.8, 29.4, 29.5, 29.6, 29.68, 29.73, 29.8, 29.87, 29.90, 32.1, 34.8, 39.0, 52.3, 62.1, 68.1, 69.3, 70.1, 70.5, 70.8, 71.7, 75.0, 80.6, 100.1, 155.0, 174.8, 178.2; HRMS (ESI): m/z calcd for C$_{57}$H$_{109}$NO$_{13}$Na [M+Na]$^+$ 1038.7797. found 1038.7793.

Example 5

Synthesis of (2S,3S,4R)-2-((2-(Benzyloxycarbonylamino)acetoxy)methoxycarbonylamino)-1-O-α-D-galactopyranosyl-4-hexacosanoyl octadecane-1,3,4-triol (CN142)

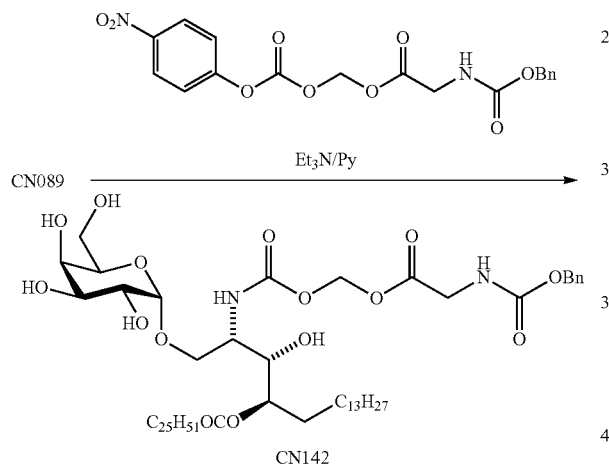

Example 5.1

(4-Nitrophenoxy)carbonyloxymethyl 2-(benzyloxycarbonylamino)acetate

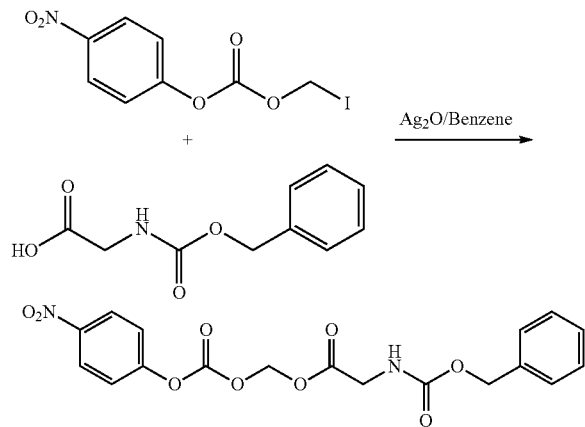

Ag$_2$O (0.71 g, 3.1 mmol) is added to a stirred solution of iodomethyl 4-nitrophenyl carbonate (Gangwar, Pauletti et al. 1997) (0.50 g, 1.55 mmol) and Cbz-protected glycine (0.65 g, 3.1 mmol) in benzene and the reaction mixture is stirred at reflux. After 3 h the solution is filtered and the solvent removed. The residue is dissolved in EtOAc (30 ml) and washed with water (30 ml), brine (30 ml), dried (MgSO$_4$) and the solvent removed. The crude residue is purified on silica gel (EtOAc/petroleum ether=3:7 to 1:1) to afford the title compound (0.24 g, 38%) as a pale yellow oil. $^1$H NMR (500 MHz, CDCl$_3$) δ 4.07 (d, J=6 Hz, 2H), 5.13 (s, 2H), 5.31 (m, 1H), 5.91 (s, 2H), 7.33-7.44 (m, 7H), 7.34 (d, J=9 Hz, 2H), 8.26 (d, J=9 Hz, 2H). $^{13}$C NMR (125 MHz) δ 42.6, 67.4, 82.7, 121.7, 125.3, 128.1, 128.3, 128.6, 135.9, 145.7, 151.3, 154.9, 168.7. HRMS-ESI [M+Na]$^+$ calcd for C$_{18}$H$_{16}$N$_2$NaO$_9$: 427.0748. Found 427.0728.

Example 5.2

(2S,3S,4R)-2-((2-(Benzyloxycarbonylamino)acetoxy)methoxycarbonylamino)-1-O-α-D-galactopyranosyl-4-hexacosanoyl octadecane-1,3,4-triol (CN142)

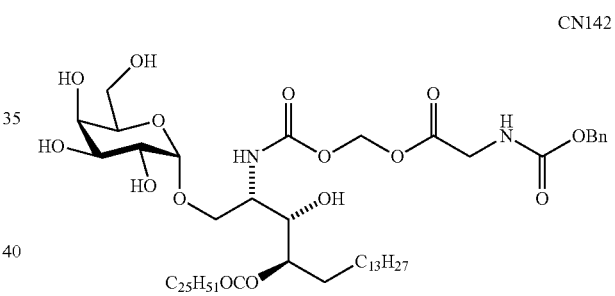

(4-Nitrophenoxy)carbonyloxymethyl 2-(benzyloxycarbonylamino)acetate (0.060 g, 0.146 mmol) is added to the amine CN089 (0.025 g, 0.029 mmol) in pyridine (3 mL). Triethylamine (1 mL) is added and the reaction is stirred for 1 h. The mixture is quenched with MeOH (30 mL) then diluted with CHCl$_3$ (20 mL) and the solvents removed. The crude residue is purified on silica gel (MeOH/CHCl$_3$=0:1 to 1:4). The sample is further purified on RP-C18 (MeOH/CHCl$_3$=1:0 to 7:3) to afford the title compound CN142 (0.022 g, 67%) as a white solid. $^1$H NMR (500 MHz, CDCl$_3$/CD$_3$OD 3:1) δ 0.80 (t, J=7.0 Hz, 6H), 1.73-1.25 (m, 68H), 1.52-1.61 (m, 4H), 2.26 (m, 2H), 3.63-3.71 (m, 8H), 3.79 (m, 1H), 3.86 (d, J=2.5 Hz, 1H), 3.91 (d, J=4.5 Hz, 1H), 4.76 (d, J=3.5 Hz, 1H), 4.84 (m, 1H), 5.04 (s, 2H), 5.64-5.76 (m, 2H), 7.25 (m, 5H). $^{13}$C NMR (125 MHz) δ 13.9, 22.6, 25.0, 25.3, 28.7, 29.1, 29.2, 29.25, 29.27, 29.37, 29.44, 29.5, 29.51, 29.54, 29.58, 29.62, 31.8, 34.5, 42.3, 52.2, 61.7, 67.0, 67.5, 69.0, 69.7, 70.2, 70.6, 71.6, 74.5, 80.2, 100.0, 128.1, 128.4, 128.7, 136.5, 155.0, 157.5, 170.0, 174.8. HRMS-ESI [M+Na]$^+$ calcd for C$_{62}$H$_{110}$N$_2$NaO$_{15}$: 1145.7798. Found 1145.7739.

Example 6

(2S,3S,4R)-2-(Benzoyloxymethoxycarbonylamino)-1-O-α-D-galactopyranosyl-4-hexacosanoyl octadecane-1,3,4-triol (CN141)

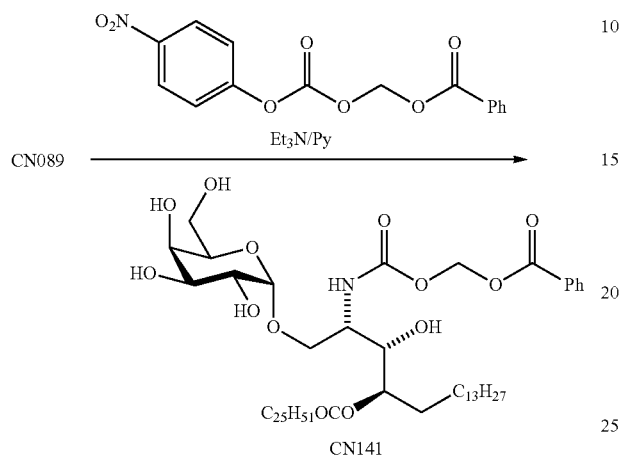

(4-Nitrophenoxy)carbonyloxymethyl benzoate (Lin, Bitha et al. 1997) (0.050 g, 0.158 mmol) is added to the amine CN089 (0.025 g, 0.029 mmol) in pyridine (3 mL). Triethylamine (1 mL) is added and the reaction is stirred for 1 h. The mixture is quenched with MeOH (30 mL) then diluted with CHCl₃ (20 mL) and the solvents removed. The crude residue is purified on silica gel (MeOH/CHCl₃=0:1 to 1:4). The sample is further purified on RP-C18 (MeOH/CHCl₃=1:0 to 7:3) to afford the title compound CN141 (0.006 g, 20%) as a white solid. $^1$H NMR (500 MHz, CDCl₃/CD₃OD 3:1) δ 0.80 (m, 6H), 1.17 (m, 68H), 1.49-1.65 (m, 4H), 2.25 (m, 2H), 3.64-3.76 (m, 10H), 4.77 (d, J=2.5 Hz, 1H), 4.84 (m, 1H), 5.90 (m, 2H), 7.36 (m, 2H), 7.53 (m, 1H), 7.98 (m, 2H). $^{13}$C NMR (125 MHz) δ 13.9, 22.6, 25.0, 25.3, 28.7, 29.1, 29.2, 29.25, 29.27, 29.33, 29.4, 29.48, 29.58, 31.8, 49.2, 49.5, 52.1, 61.8, 67.7, 69.0, 69.8, 70.1, 70.5, 71.4, 74.7, 80.6, 99.8, 128.4, 129.0, 129.9, 133.7, 154.8, 165.8, 174.5. HRMS-ESI [M+Na]$^+$ calcd for C₅₉H₁₀₅NNaO₁₃: 1058.7478. Found 1058.7440.

Example 7

Synthesis of (2S,3S,4R)-1-O-α-D-Galactopyranosyl-4-hexacosanoyl-2-((4-oxopentanoyloxy)methoxycarbonylamino) octadecane-1,3,4-triol (CN146)

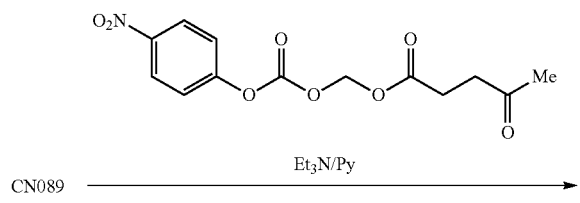

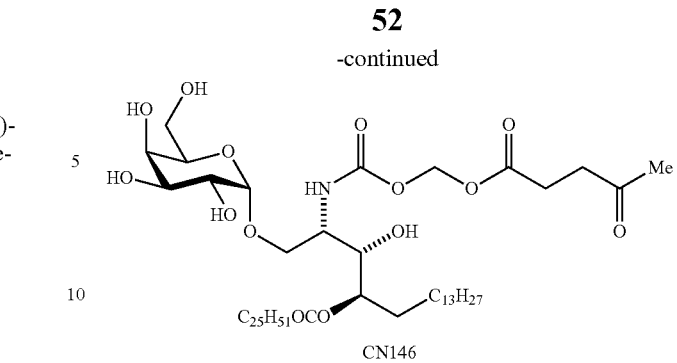

Example 7.1

(4-Nitrophenoxy)carbonyloxymethyl 4-oxopentanoate

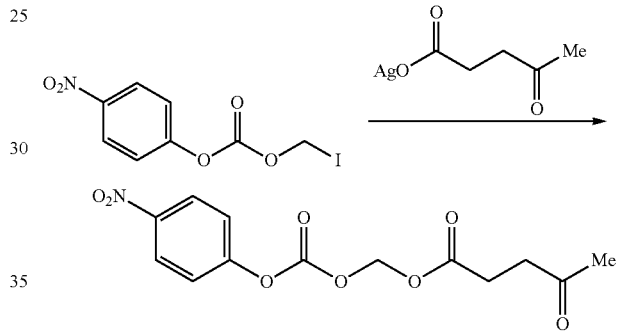

The silver salt of levulinic acid is prepared by adding a solution of AgNO₃ (700 mg, 4.1 mmol) in water (10 mL) to the sodium salt of levulinic acid (4.3 mmol in ~10 mL water, prepared by basification of levulinic acid with 1 M aq NaOH to pH 7-8). After 30 min, the resultant precipitate is isolated by filtration and washed with cold water followed by Et₂O. The product is dried under vacuum to afford the silver salt as a white solid (636 mg, 69%). A mixture of iodomethyl 4-nitrophenyl carbonate (Gangwar, Pauletti et al. 1997) (105 mg, 0.325 mmol, dried by azeotropic distillation with toluene), 4 Å molecular sieves (~250 mg) and silver levulinate (89 mg, 0.40 mmol) in dry toluene (1.5 mL) is protected from light and stirred at 40° C. After 4 h, the mixture is diluted with Et₂O, filtered through celite, and concentrated under reduced pressure. The crude residue is purified by silica gel chromatography (30% to 40% EtOAc/petroleum ether) to afford the title compound (85 mg, 84%) as a colourless oil. $^1$H NMR (500 MHz, CDCl₃) δ 2.20 (s, 3H), 2.67-2.70 (m, 2H), 2.80-2.83 (m, 2H), 5.88 (s, 2H), 7.38-7.48 (m, 2H), 8.24-8.34 (m, 2H); $^{13}$C NMR (126 MHz, CDCl₃) δ 27.7, 29.7, 37.6, 82.5, 121.8, 125.4, 145.7, 151.5, 155.1, 171.2, 206.0; HRMS (ESI): m/z calcd for C₁₃H₁₃NO₈Na [M+Na]$^+$ 334.0539. found 334.0544.

Example 7.2

(2S,3S,4R)-1-O-α-D-Galactopyranosyl-4-hexacosanoyl-2-((4-oxopentanoyloxy)methoxycarbonylamino) octadecane-1,3,4-triol (CN146)

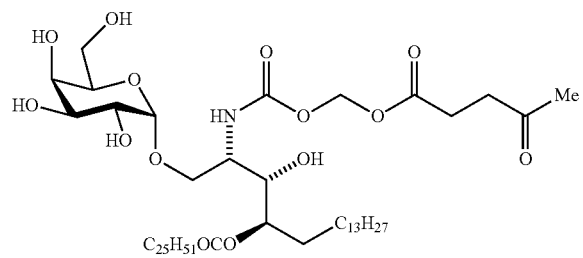

CN146

To a solution of amine CN089 (22 mg, 0.026 mmol) in $d_5$-pyridine (0.30 mL) is added a solution of (4-nitrophenoxy)carbonyloxymethyl 4-oxopentanoate (8.0 mg, 0.026 mmol) in $CDCl_3$ (0.15 mL). The progress of the reaction is followed in an NMR tube. After 3 h at rt, $NEt_3$ (2.5 mg, 0.025 mmol) is added and the reaction is allowed to continue for a further 2.25 h, after which time >95% of the amine CN089 has been consumed. The volatiles are concentrated under reduced pressure and the crude residue is purified by silica gel chromatography (1.5:40:60 to 1.5:45:55 MeOH/dioxane/$CHCl_3$) to afford the title compound CN146 (14.1 mg, 53%) as a white solid. $^1$H NMR (500 MHz, 1:1 $CDCl_3$/$CD_3OD$) δ 0.88-0.90 (m, 6H), 1.24-1.34 (m, 68H), 1.60-1.72 (m, 4H), 2.21 (s, 3H), 2.31-2.42 (m, 2H), 2.62-2.64 (m, 2H), 2.80-2.83 (m, 2H), 3.71-3.83 (m, 8H), 3.88 (br d, J=10.1 Hz, 1H), 3.95 (br d, J=2.2 Hz, 1H), 4.86 (d, J=3.2 Hz, 1H) 4.94-4.98 (m, 1H), 5.68-5.76 (m, 2H); $^{13}$C NMR (126 MHz, 1:1 $CDCl_3$/$CD_3OD$) δ 14.3, 23.2, 25.6, 25.9, 28.3, 29.3, 29.7, 29.79, 28.84, 29.86, 29.92, 30.0, 30.1, 30.15, 30.18, 30.21, 32.43, 32.44, 35.1, 38.1, 53.0, 62.3, 68.1, 69.7, 70.4, 70.8, 71.4, 72.1, 75.2, 80.7, 100.5, 155.6, 172.7, 175.0, 208.5; HRMS (ESI): m/z calcd for $C_{57}H_{107}NO_{14}Na$ [M+Na]$^+$ 1052.7589. found 1052.7578.

Example 8

(2S,3S,4R)-1-O-α-D-Galactopyranosyl-4-hexacosanoyl-2-((4-(2-methoxy(poly(2-ethoxy))imino)pentanoyloxy)methoxycarbonylamino) octadecane-1,3,4-triol (CN147)

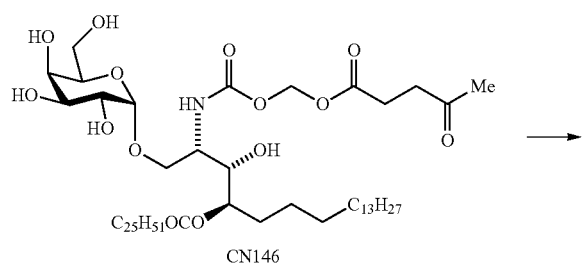

CN146

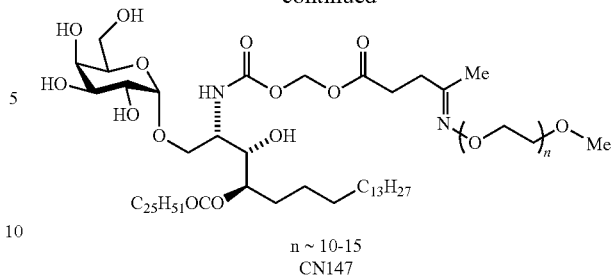

n ~ 10-15
CN147

A mixture of ketone CN146 (10 mg, 0.0097 mmol), 2-methoxy(poly(2-ethoxy))amine (average Mw~500) (Iha, van Horn et al. 2010) (5.4 mg, 0.009 mmol) and acetic acid (0.5 mg, 0.008 mmol) in 1:1 $CDCl_3$/$CD_3OD$ (0.15 mL) is allowed to react at rt. The progress of the reaction is followed in an NMR tube. After 15 h, a further portion of the alkoxyamine (3 mg, 0.005 mmol) is added and the reaction is left for 3 days before diluting with $CHCl_3$/toluene and concentrating the volatiles under reduced pressure. The crude residue is purified by silica gel chromatography (5% to 10% MeOH/$CHCl_3$) to afford the title compound CN147 (12.3 mg, 78%) as an oil. $^1$H NMR (500 MHz, 1:1 $CDCl_3$/$CD_3OD$) δ 0.88-0.90 (m, 6H), 1.24-1.34 (m, 68H), 1.60-1.73 (m, 4H), 1.87 and 1.90 (2×s, 3H), 2.32-2.42 (m, 2H), 2.50-2.53 and 2.62-2.64 (2×m, 4H), 3.39 (s, 3H), 3.56-3.58 (m, 2H), 3.62-3.82 (m, ~66H), 3.87 (br d, J=10.2 Hz, 1H), 3.95 (d, J=2.6 Hz, 1H), 4.14-4.16 (m, 2H), 4.86 (d, J=3.4 Hz, 1H), 4.94-4.98 (m, 1H), 5.70-5.78 (m, 2H); $^{13}$C NMR (126 MHz, 1:1 $CDCl_3$/$CD_3OD$) δ 14.27, 14.29, 14.9, 20.2, 23.2, 25.2, 25.6, 25.9, 29.3, 29.7, 29.85, 29.93, 30.1, 30.2, 30.3, 30.7, 31.0, 32.4, 35.1, 53.0, 59.1, 62.3, 68.1, 69.7, 70.11, 70.14, 70.4, 70.8, 71.0, 71.3, 71.4, 72.1, 72.4, 73.1, 73.2, 75.2, 80.7, 80.8, 100.5, 155.6, 156.4, 157.9, 158.9, 172.6, 172.7, 175.0; HRMS (ESI): m/z calcd for $C_{82}H_{158}N_2O_{26}Na$ (n=12) [M+Na]$^+$ 1610.1001. found 1610.1012.

Example 9

(2S,3S,4R)-1-O-α-D-Galactopyranosyl-4-hexacosanoyl-2-((4-methoxybenzoyloxy)methoxycarbonylamino) octadecane-1,3,4-triol (CN150)

CN089 ⟶

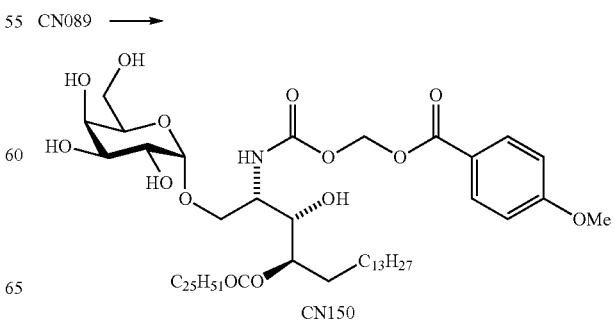

CN150

Example 9.1

(4-Nitrophenoxy)carbonyloxymethyl 4-methoxybenzoate

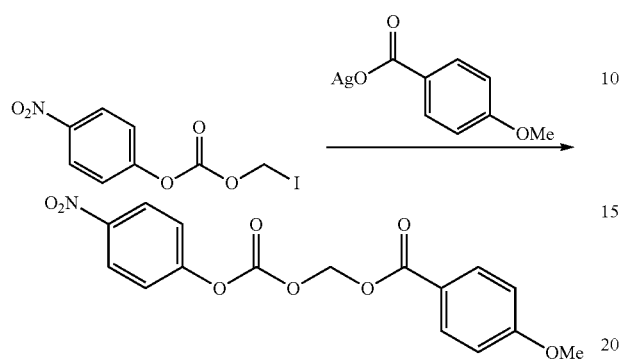

Silver 4-methoxybenzoate (prepared in the same manner as silver levulinate (Example 7.1), 0.32 g, 1.24 mmol) is dried by azeotropic distillation with toluene (20 mL) in a rotary evaporator. The residue is suspended in dry toluene (40 mL) and iodomethyl 4-nitrophenyl carbonate (Gangwar, Pauletti et al. 1997) (200 mg, 0.619 mmol) is added. The mixture is stirred at reflux for 1 h, cooled, and filtered. After concentration of the filtrate, the crude residue is purified by silica gel chromatography (5% to 30% EtOAc/petroleum ether) to afford the title compound (190 mg, 88%) as a white solid. $^1$H NMR (500 MHz, CDCl$_3$) δ 3.88 (s, 3H), 6.11 (s, 2H), 6.95 (m, 2H), 7.41 (m, 2H), 8.05 (m, 2H), 8.27 (m, 2H). $^{13}$C NMR (126 MHz, CDCl$_3$) δ 55.5, 82.8, 113.9, 120.6, 121.7, 125.3, 132.3, 145.6, 151.5, 155.1, 164.2, 164.4. HRMS (ESI): m/z calcd for C$_{16}$H$_{13}$NO$_8$Na [M+Na]$^+$ 370.0539. found 370.0545.

Example 9.2

(2S,3S,4R)-1-O-α-D-Galactopyranosyl-4-hexacosanoyl-2-(4-methoxybenzoyloxyl)methoxycarbonylamino octadecane-1,3,4-triol (CN150)

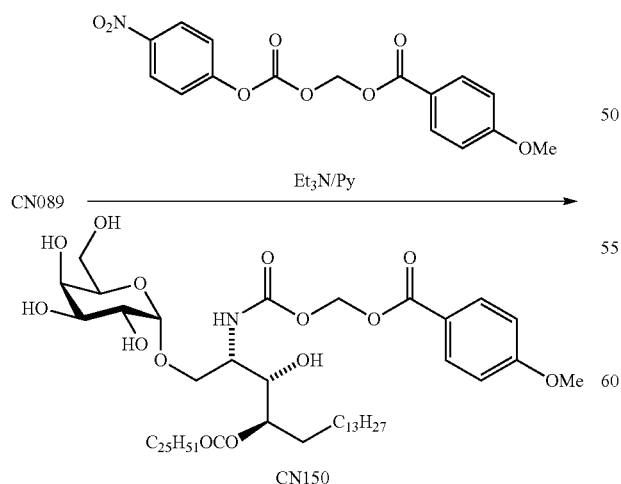

(4-Nitrophenoxy)carbonyloxymethyl 4-methoxybenzoate (0.050 g, 0.14 mmol) is added to the amine CN089 (0.030 g, 0.037 mmol) dissolved in 1:1 CH$_2$Cl$_2$/pyridine (4 mL). Triethylamine (2 mL) is added and the reaction is stirred for 1 h at rt. The mixture is diluted with CH$_2$Cl$_2$ (10 mL) and concentrated. The crude residue is purified on silica gel (MeOH/CHCl$_3$=0:1 to 15:85) to afford the title compound CN150 (0.020 g, 61%) as a white solid. $^1$H NMR (500 MHz, CDCl$_3$/CD$_3$OD 3:1) δ 0.89 (m, 6H), 1.23-1.32 (m, 68H), 1.58-1.71 (m, 4H), 2.29-2.39 (m, 2H), 3.70-3.81 (m, 8H), 3.84-3.88 (m, 4H), 3.93 (m, 1H), 4.86 (d, J=3.6 Hz, 1H), 4.93 (m, 1H), 5.94 (d, J=5.8 Hz, 1H), 5.96 (d, J=5.8 Hz, 1H), 6.93-6.96 (m, 2H), 8.01-8.04 (m, 2H). $^{13}$C NMR (125 MHz, CDCl$_3$/CD$_3$OD 3:1) δ 14.2, 22.9, 25.3, 25.6, 29.1, 29.5, 29.62, 29.64, 29.7, 29.8, 29.86, 29.92, 29.95, 29.99, 32.2, 34.9, 52.5, 55.7, 62.2, 68.1, 69.4, 70.1, 70.5, 70.9, 71.8, 75.1, 80.8, 100.2, 114.1, 121.6, 132.4, 155.3, 164.4, 165.9, 174.8. HRMS (ESI): m/z calcd for C$_{60}$H$_{107}$NO$_{14}$Na [M+Na]$^+$ 1088.7589. found 1088.7587.

Example 10

(2S,3S,4R)-1-O-α-D-Galactopyranosyl-4-hexacosanoyl-2-((4-nitrobenzoyloxy)methoxycarbonylamino) octadecane-1,3,4-triol (CN151)

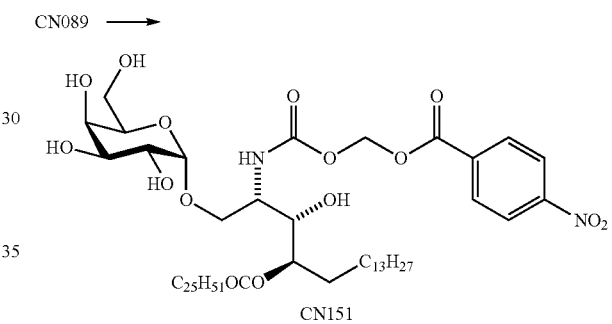

Example 10.1

(4-Nitrophenoxy)carbonyloxymethyl 4-nitrobenzoate

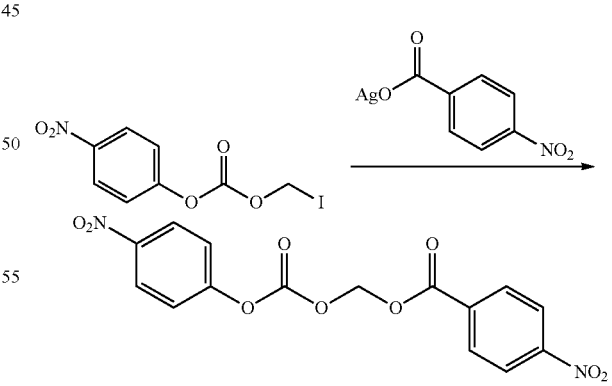

The title compound is prepared in the same manner as (4-nitrophenoxy)carbonyloxymethyl 4-nitrobenzoate (Example 9.1), as a white solid (81 mg, 36%). $^1$H NMR (500 MHz, CDCl$_3$) δ 6.17 (s, 2H), 7.43 (m, 2H), 8.28-8.31 (m, 2H), 8.33 (m, 2H). $^{13}$C NMR (126 MHz, CDCl$_3$) δ 83.2, 121.6, 123.8, 125.4, 131.3, 133.7, 145.8, 151.2, 151.4, 154.9, 163.1. HRMS (ESI): m/z calcd for C$_{15}$H$_{10}$N$_2$O$_9$Na [M+Na]$^+$ 385.0284. found 385.0281.

Example 10.2

(2S,3S,4R)-1-O-α-D-Galactopyranosyl-4-hexacosanoyl-2-((4-nitrobenzoyloxy)methoxycarbonylamino) octadecane-1,3,4-triol (CN151)

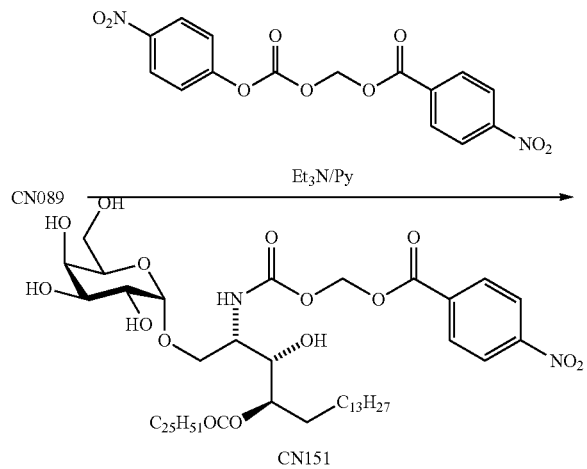

(4-Nitrophenoxy)carbonyloxymethyl 4-methoxybenzoate (0.060 g, 0.17 mmol) is added to the amine CN089 (0.040 g, 0.047 mmol) dissolved in 2:1 CH$_2$Cl$_2$/pyridine (6 mL). Triethylamine (1 mL) is added and the reaction is stirred for 30 min at rt. The mixture is diluted with CHCl$_3$ (10 mL) and concentrated. The crude residue is purified on silica gel (MeOH/CHCl$_3$=0:1 to 15:85) to afford the title compound CN151 (0.020 g, 61%) as a white solid. $^1$H NMR (500 MHz, CDCl$_3$/CD$_3$OD 3:1) δ 0.88 (m, 6H), 1.23-1.32 (m, 68H), 1.58-1.71 (m, 4H), 2.29-2.39 (m, 2H), 3.70-3.81 (m, 8H), 3.87 (dd, J=2.4, 10.2 Hz, 1H), 3.94 (m, 1H), 4.86 (d, J=3.6 Hz, 1H), 4.93 (m, 1H), 5.99 (d, J=5.9 Hz, 1H), 6.04 (d, J=5.9 Hz, 1H), 8.26-8.29 (m, 2H), 8.30-8.33 (m, 2H). $^{13}$C NMR (125 MHz, CDCl$_3$/CD$_3$OD 3:1) δ 14.2, 22.9, 25.3, 25.7, 28.9, 29.4, 29.56, 29.58, 29.60, 29.7, 29.77, 29.83, 29.88, 29.92, 29.95, 32.2, 34.8, 52.6, 62.1, 68.0, 69.3, 70.0, 70.5, 71.0, 71.8, 75.0, 81.5, 100.1, 123.9, 131.4, 134.9, 151.2, 154.9, 164.1, 174.8. HRMS (ESI): m/z calcd for C$_{59}$H$_{104}$N$_2$O$_{15}$Na [M+Na]$^+$ 1103.7334. found 1103.7340.

Example 11

Synthesis of (2S,3S,4R)-2-Acetoxymethoxycarbonylamino-1-O-α-D-galactopyranosyl-4-O-(6-phenylhexanoyl) octadecane-1,3,4-triol (CN135)

Example 11.1

Synthesis of (2S,3S,4R)-3,4-Di-O-benzyl-1-O-(2,3-di-O-benzyl-4,6-O-benzylidene-α-D-galactopyranosyl)-2-(6-phenylhexanoylamino) octadec-6-ene-1,3,4-triol (20)

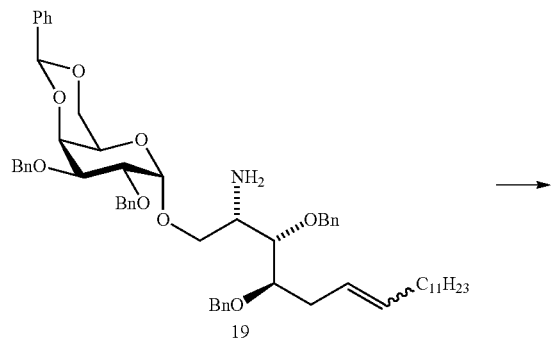

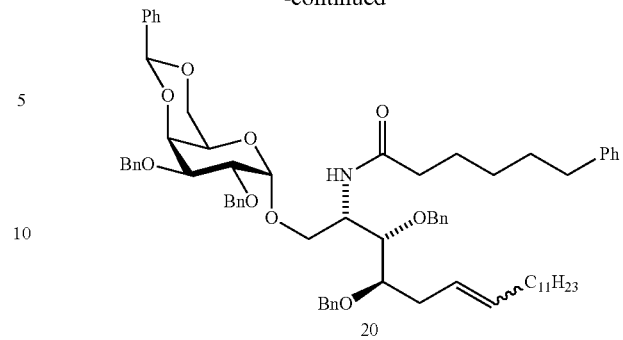

Phenylhexanoic acid (0.031 g, 0.162 mmol) is added to a stirred solution of EDC-HCl (0.041 g, 0.216 mmol) and HOBt-H$_2$O (0.033 g, 0.216 mmol) in CH$_2$Cl$_2$/DMF (5:2, 10 mL). After 30 min a solution of (2S,3S,4R)-2-amino-3,4-di-O-benzyl-1-O-(2,3-di-O-benzyl-4,6-O-benzylidene-α-D-galactopyranosyl) octadec-6-ene-1,3,4-triol (19) (Plettenburg, Bodmer-Narkevitch et al. 2002) (0.10 g, 0.108 mmol) in CH$_2$Cl$_2$ (10 ml) then DIPEA (0.075 mL, 0.432 mmol) is added. After 18 h the reaction mixture is diluted with CH$_2$Cl$_2$ (50 mL), washed with water (50 mL), dried (MgSO$_4$), filtered and the solvent removed. The crude residue is purified on silica gel (EtOAc/petroleum ether=0:1 to 2:3) to give compound 20 (0.101 g, 85%) as a pale yellow oil. $^1$H NMR (500 MHz, CDCl$_3$) δ 0.90 (t, J=7.0 Hz, 3H), 1.23-1.34 (m, 20H), 1.52 (t, J=7.5 Hz, 2H), 1.58 (t, J=7.5 Hz, 2H), 1.86 (m, 2H), 2.02 (m, 2H), 2.34 (t, J=8.5 Hz, 1H), 2.47 (m, 2H), 2.59 (m, 2H), 3.58 (m, 2H), 3.76 (m, 2H), 3.93 (m, 3H), 4.08 (m, 2H), 4.18 (br s, 1H), 4.39 (m, 1H), 4.50 (m, 2H), 4.58-4.65 m, 3H), 4.69-4.83 (m, 2H), 4.85 (d, J=11.5 Hz, 1H), 4.96 (d, J=2.5 Hz, 1H), 5.46 (s, 1H), 5.49 (m, 2H), 5.73 (d, J=8.5 Hz, 1H), 7.14-7.36 (m, 28H), 7.51 (m, 2H); $^{13}$C NMR (125 MHz) δ 14.1, 22.7, 24.6, 25.5, 27.6, 28.7, 28.9, 29.3, 29.37, 29.44, 29.55, 29.60, 29.64, 29.67, 29.68, 29.71, 29.73, 31.1, 31.2, 31.9, 32.8, 33.4, 33.5, 35.7, 35.8, 36.6, 50.3, 63.0, 68.2, 69.4, 71.61, 71.63, 71.7, 73.3, 73.4, 73.8, 74.4, 75.7, 76.1, 79.0, 79.3, 80.0, 99.59, 99.64, 101.0, 125.1, 125.7, 126.3, 127.55, 127.57, 127.63, 127.68, 127.75, 127.78, 127.84, 127.85, 127.88, 128.1, 128.27, 128.29, 128.31, 128.32, 128.36, 128.39, 128.5, 128.8, 132.3, 137.9, 138.3, 138.4, 138.6, 138.7, 142.5, 172.8; HRMS (ESI): m/z calcd for C$_{71}$H$_{89}$NNaO$_9$ [M+Na]$^+$ 1122.6430. found 1122.6369.

Example 11.2

Synthesis of (2S,3S,4R)-1-O-α-D-Galactopyranosyl-2-(6-phenylhexanoylamino) octadecane-1,3,4-triol (21)

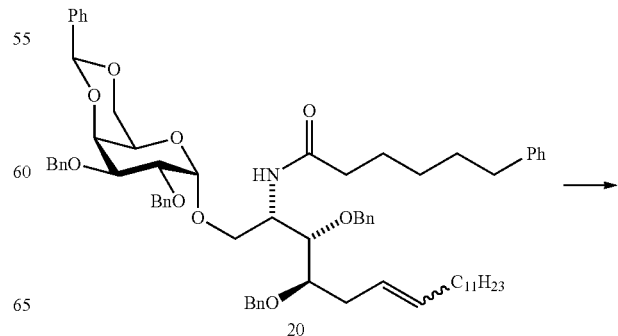

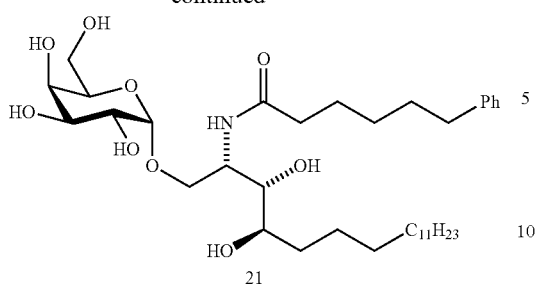

21

Pd(OH)$_2$ (20% on C, 100 mg) is added to a stirred solution of compound 20 (0.101 g, 0.092 mmol) in CH$_2$Cl$_2$/MeOH (1:4, 5 mL). The solution is stirred under an atmosphere of H$_2$ for 4 h. The mixture is filtered through Celite and the solvent removed. The crude residue is purified on silica gel (MeOH/CHCl$_3$=1:9 to 3:7) to afford compound 21 (0.046 g, 77%) as a colourless oil. $^1$H NMR (500 MHz, CDCl$_3$/CD$_3$OD 3:1) δ 0.80 (t, J=7.0 Hz, 3H), 1.17-132 (m, 26H), 1.53-1.59 (m, 6H), 2.12 (t, J=7.6 Hz, 2H), 2.53 (t, J=7.8 Hz, 2H), 3.43-3.48 (m, 2H), 3.58-3.72 (m, 6H), 3.78-3.81 (m, 1H), 3.85 (d, J=2.5 Hz, 1H), 4.12 (m, 1H), 4.81 (d, J=3.9 Hz, 1H), 7.08 (m, 3H), 7.18 (m, 2H); $^{13}$C NMR (125 MHz) δ 13.8, 22.6, 25.6, 25.8, 28.8, 29.2, 29.5, 29.59, 29.60, 29.63, 29.7, 31.1, 31.8, 32.6, 35.6, 36.2, 50.4, 61.8, 67.3, 68.9, 69.7, 70.2, 70.7, 71.9, 74.7, 99.7, 125.5, 128.1, 128.2, 142.4, 174.3. HRMS (ESI): m/z calcd for C$_{36}$H$_{63}$NNaO$_9$ [M+Na]$^+$ 676.4401. found 676.4273.

Example 11.3

Synthesis of (2S,3S,4R)-2-Acetoxymethoxycarbonylamino-1-O-α-D-galactopyranosyl-4-O-(6-phenylhexanoyl) octadecane-1,3,4-triol (CN135)

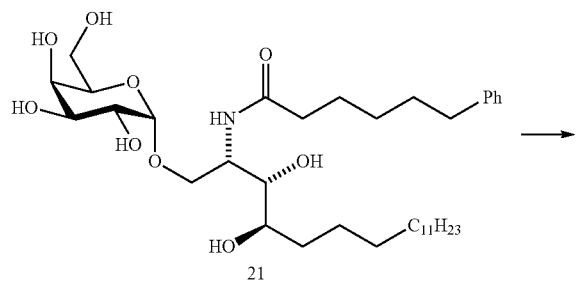

21

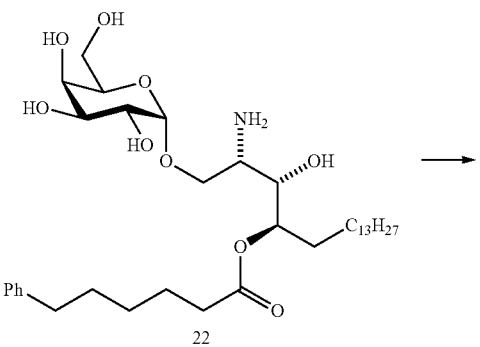

22

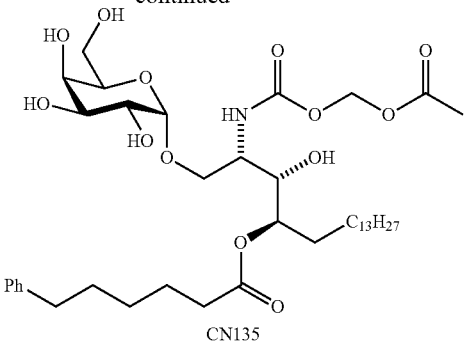

CN135

HCl (1 M, 0.74 mL) is added to a solution of compound 21 (0.045 g, 0.068 mmol) in dioxane/water (10:1, 4 mL), previously warmed to 80° C. (5 min), and heated at 90° C. (45 min). The solution is then lyophilized and the residue is purified on silica gel (MeOH/CHCl$_3$=1:4 to 1:1) to afford the amine-ester 22 (0.030 g, 67%) as a white solid. (4-Nitrophenoxy)carbonyloxy)methyl acetate (0.040 g, 0.160 mmol) is added to the amine-ester (0.030 g, 0.045 mmol) in pyridine (3 mL). NEt$_3$ (1 mL) is added and the reaction is stirred for 1 h. The mixture is quenched with MeOH (30 mL) then diluted with CHCl$_3$ (20 mL) and the solvents removed. The crude residue is purified on silica gel (MeOH/CHCl$_3$=0:1 to 1:4). The sample is further purified on RP-C18 (MeOH/CHCl$_3$=1:0 to 4:1) to afford the title compound CN135 (0.017 g, 48%) as a white solid. $^1$H NMR (500 MHz, CDCl$_3$/CD$_3$OD 3:1) δ 0.85 (t, J=7.0 Hz, 3H), 1.22-128 (m, 26H), 1.61-1.65 (m, 6H), 2.08 (s, 3H), 2.32 (t, J=7.6 Hz, 2H), 2.58 (t, J=7.8 Hz, 2H), 3.69-3.76 (m, 10H), 4.82 (d, J=2.5 Hz, 1H), 4.89 (m, 1H), 5.68 (m, 2H), 7.13 (m, 3H), 7.41 (m, 2H); $^{13}$C NMR (125 MHz) δ 14.2, 20.8, 22.9, 25.2, 25.6, 29.0, 29.1, 29.6, 29.7, 29.86, 29.91, 29.94, 30.0, 31.4, 32.2, 34.8, 36.0, 52.4, 62.1, 68.0, 69.3, 70.1, 70.5, 70.9, 71.8, 75.0, 80.4, 100.1, 125.9, 128.5, 128.6, 142.7, 155.2, 170.9, 174.7; HRMS (ESI): m/z calcd for C$_{40}$H$_{67}$NNaO$_{13}$ [M+Na]$^+$ 792.4510. found 792.4504.

Example 12

(2S,3S,4R)-1-O-α-D-Galactopyranosyl-4-hexacosanoyl-2-((ω-methoxy(poly(ethyleneoxy))acetoxy) methylenoxycarbonylamino) octadecane-1,3,4-triol (CN155)

Example 12.1

ω-Methoxy(poly(ethyleneoxy))acetic acid

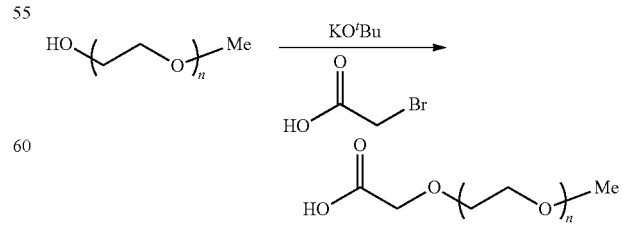

A mixture of polyethyleneglycol monomethyl ether (average Mw 5000) (2 g, 0.4 mmol) and t-BuOK (1M in t-BuOH, 1.6 mL, 1.6 mmol) is stirred in t-BuOH overnight at 50° C.

To the mixture is added a solution of bromoacetic acid (80 mg, 0.58 mmol) in t-BuOH (1.1 mL) and the reaction is stirred at 50° C. for 26 h. The volatiles are concentrated under reduced pressure and the residue is dissolved in water and acidified to pH 2 with 1 M HCl. The product is extracted with dichloromethane (×3) and dried over MgSO$_4$. The crude residue is purified by silica gel chromatography (0:10 to 1:9 MeOH/dichloromethane) to give the title compound as a white solid (601 mg, 30%). $^1$H NMR (500 MHz, CDCl$_3$) δ 3.38 (s, 3H), 3.49-3.79 (m, ~488H), 4.14 (s, 2H); $^{13}$C NMR (126 MHz, CDCl$_3$) 59.0, 68.9, 70.4-70.8 (m), 70.9, 71.1, 72.0, 171.6; HRMS (ESI): m/z calcd for C$_{231}$H$_{464}$O$_{117}$Na (n=114) [M+2H+Na]$^{3+}$ 1711.3419. found 1711.3702.

Example 12.2

(4-Nitrophenoxy)carbonyloxymethyl ω-methoxy(poly(ethyleneoxy))acetate

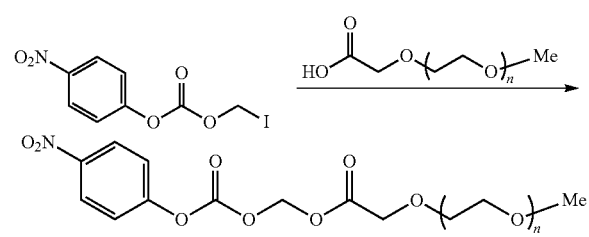

A mixture of ω-methoxy(poly(ethyleneoxy))acetic acid (561 mg, ~0.11 mmol), Ag$_2$O (14.3 mg, 0.0617 mmol) and 4 Å molecular sieves (~290 mg) is stirred in toluene overnight. To the mixture is added iodomethyl 4-nitrophenyl carbonate (Gangwar, Pauletti et al. 1997) (50 mg, 0.155 mmol) and the reaction is stirred under Ar at 40° C. After 100 min, the mixture is diluted with dichloromethane, filtered through celite, and concentrated under reduced pressure. The product is precipitated from a concentrated dichloromethane solution by addition of Et$_2$O (3 volumes), and filtered to give the title compound as an off-white solid (524 mg, 90%). $^1$H NMR (500 MHz, CDCl$_3$) δ 3.38 (s, 3H), 3.49-3.79 (m, ~546H), 4.28 (s, 2H), 5.94 (s, 2H), 7.41-7.44 (m, 2H), 8.28-8.31 (m, 2H); $^{13}$C NMR (126 MHz, CDCl$_3$) 59.0, 68.3, 70.4-70.8 (m), 70.9, 71.2, 72.0, 82.5, 121.7, 125.4, 145.8, 151.4, 155.0, 169.1; HRMS (ESI): m/z calcd for C$_{235}$H$_{461}$NO$_{120}$Na (n=112) [M+2H+Na]$^{3+}$ 1746.9966. found 1746.9926.

Example 12.3

(2S,3S,4R)-1-O-α-D-Galactopyranosyl-4-hexacosanoyl-2-((ω-methoxy(poly(ethyleneoxy))acetoxy) methylenoxycarbonylamino) octadecane-1,3,4-triol (CN155)

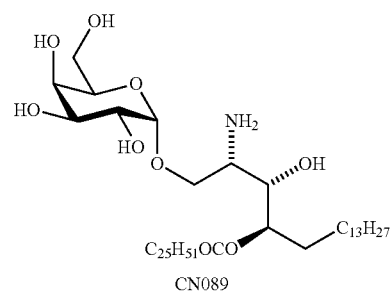
CN089

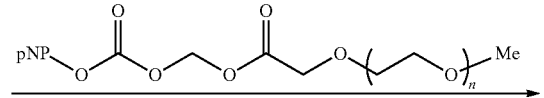

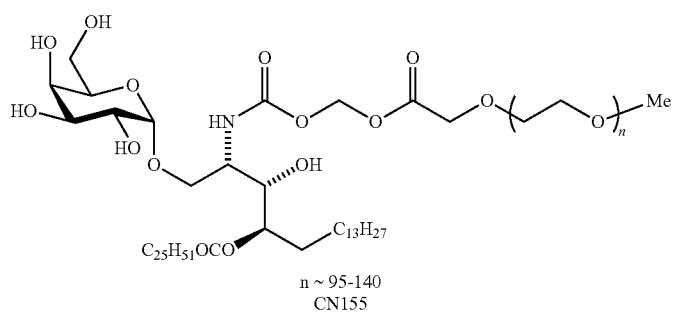
n ~ 95-140
CN155

A mixture of amine CN089 (13 mg, 0.015 mmol) and (4-nitrophenoxy)carbonyloxymethyl ω-methoxy(poly(ethyleneoxy))acetate (82 mg, ~0.015 mmol) in 1:1 dichloromethane-pyridine (0.7 mL) is stirred with 4 Å molecular sieves at rt, while NEt$_3$ is added in 3 portions over 1.5 h (3×2.5 μL, 0.054 mmol total). After a further 7 h, the mixture is filtered and concentrated. The crude residue is purified by silica gel chromatography (2:98 to 15:85 MeOH/dichloromethane) to afford the title compound CN155 (44 mg, 48%) as a white solid. $^1$H NMR (500 MHz, CDCl$_3$) δ 0.86-0.89 (m, 6H), 1.11-1.34 (m, 68H), 1.56-1.65 (m, 3H), 1.72-1.79 (m, 1H), 2.32 (t, J=7.5 Hz, 2H), 3.38 (s, 3H), 3.49-3.86 (m, ~560H), 3.95-3.98 (m, 1H), 4.04 (br s, 1H), 4.22 (s, 2H), 4.92-4.97 (m, 2H), 5.73 (d, J=5.8 Hz, 1H), 5.85 (d, J=5.8 Hz, 1H), 6.21 (d, J=9.0 Hz, 1H); $^{13}$C NMR (126 MHz, CDCl$_3$) δ 14.0, 22.6, 24.9, 29.1, 29.2, 29.4-29.6 (m), 30.3, 31.8, 34.5, 51.5, 58.9, 62.5, 68.2, 68.4, 68.5, 69.0, 70.0, 70.2-70.6 (m), 70.8, 71.8, 73.2, 73.9, 80.0, 100.0, 154.1, 169.7, 173.6; LRMS (ESI): m/z calcd for C$_{283}$H$_{565}$NO$_{128}$Na (n=114) [M+4H+Na]$^{5+}$ 1209.95. found 1209.93.

Example 13

(2S,3S,4R)-1-O-α-D-Galactopyranosyl-4-hexacosanoyl-2-((4-(ω-methoxy(poly(ethyleneoxy))imino)pentanoyloxy)methyleneoxycarbonylamino) octadecane-1,3,4-triol (CN158)

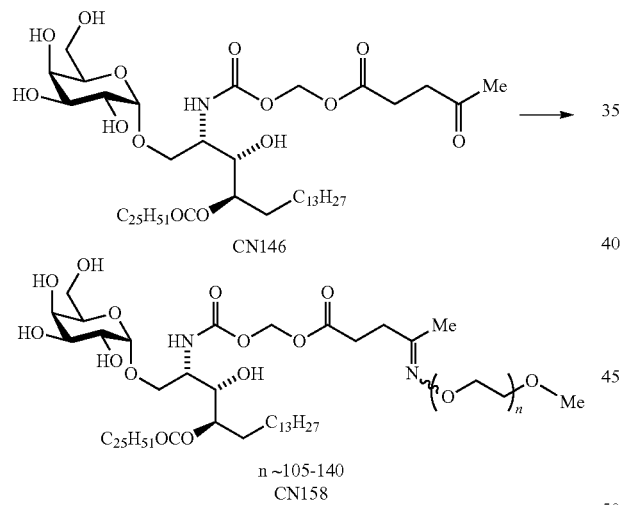

α-Methoxy-ω-aminooxy(poly(ethylene oxide)) (average Mw~5000) is synthesised in an analogous manner to the lower-Mw polymer described in: Iha, Van Horn et al, 2010. C18 silica gel chromatography is used to separate intermediates from unreacted starting materials. A mixture of the aforementioned alkoxyamine (75 mg, 0.015 mmol), ketone CN146 (13 mg, 0.013 mmol), and acetic acid (5 mg, 0.09 mmol) in 1:1 CDCl$_3$/CD$_3$OD (1.5 mL) is allowed to react at rt. The progress of the reaction is followed in an NMR tube. After 3 d, a further portion of the alkoxyamine (50 mg, 0.010 mmol) is added and the reaction is left for a further 18 h before concentrating the volatiles under reduced pressure. The crude residue is purified by reversed phase C18 silica gel chromatography (60% to 100% MeOH/water) to afford the title compound CN158 (33 mg, 43%) as a white solid. $^1$H NMR (500 MHz, CDCl$_3$) δ 0.86-0.89 (m, 6H), 1.12-1.40 (m, 68H), 1.55-1.66 (m, 3H), 1.73-1.81 (m, 1H), 1.84 and 1.89 (2×s, 3H), 2.25-2.41 (water, overlapping m), 2.49-2.53 (m, 1.3H), 2.60-2.64 (m, 2.7H), 2.96-3.01 (br m, 1H), 3.38 (s, 3H), 3.45-3.89 (m, ~490H), 3.95-4.00 (m, 1H), 4.03 (s, 1H), 4.12-4.17 (m, 2H), 4.89-5.00 (m, 2H), 5.69-5.72 (m, 1H), 5.76-5.80 (m, 1H), 6.13 and 6.23 (2×d, J=9 Hz, 1H); $^{13}$C NMR (126 MHz, CDCl$_3$) δ 14.0, 14.8, 20.1, 22.6, 24.7, 24.90, 24.93, 24.95, 29.1, 29.22, 29.24, 29.25, 29.4, 29.48, 29.51, 29.53, 29.55, 29.58-29.63 (m), 29.8, 30.1, 30.5, 30.6, 31.8, 34.5, 51.4, 58.9, 62.55, 62.64, 68.5, 68.7, 68.99, 69.02, 69.45, 69.53, 70.0, 70.1, 70.2, 70.3, 70.37, 70.41, 70.42-70.5 (m), 71.8, 72.5, 72.6, 73.3, 73.5, 73.76, 73.84, 79.5, 80.0, 100.04, 100.08, 154.2, 154.4, 155.1, 156.5, 171.7, 171.8, 173.6; HRMS (ESI): m/z calcd for C$_{298}$H$_{592}$N$_2$O$_{134}$Na$_2$ (n=120) [M+2H+2Na]$^{4+}$ 1597.4842. found 1597.4863.

Example 14

(2S,3S,4R)-1-O-α-D-Galactopyranosyl-4-hexacosanoyl-2-(3-(2-acetoxy-4,6-dimethylphenyl)-3,3-dimethylpropionoylamino) octadecane-1,3,4-triol (CN162)

Example 14.1

3-(2-Acetoxy-4,6-dimethylphenyl)-3,3-dimethylpropionic acid succinimidyl ester

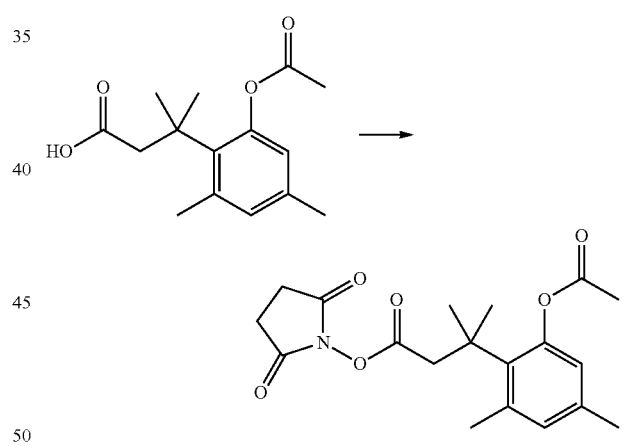

N-Hydroxysuccinimide (90 mg, 0.77 mmol) followed by DCC (160 mg, 0.77 mmol) are added to a stirred solution of 3-(2-acetoxy-4,6-dimethylphenyl)-3,3-dimethylpropionic acid (100 mg, 0.38 mmol) (Amsberry, Gerstenberger et al. 1991) in DCM (6 mL). After 5 h the mixture is filtered through celite and the concentrated residue (170 mg) purified by chromatography on silica gel. Elution with EtOAc/petroleum ether (0:10 to 9:1) affords the title compound (128 mg, 94%) as a white solid. $^1$H NMR (500 MHz, CDCl$_3$) δ 1.63 (s, 6H), 2.22 (s, 3H), 2.32 (s, 3H), 2.54 (s, 3H), 2.75 (bs, 4H), 3.13 (s, 2H), 6.62 (bs, 1H), 6.82 (bs, 1H); $^{13}$C NMR (126 MHz, CDCl$_3$) δ 20.3, 21.8, 25.2, 25.6, 30.9, 39.0, 123.2, 132.5, 132.6, 136.7, 137.8, 149.4, 166.6, 169.1, 169.9; HRMS (ESI): m/z calcd for C$_{19}$H$_{23}$NO$_6$Na [M+Na]$^+$ 384.1423. found 384.1417.

Example 14.2

(2S,3S,4R)-1-O-α-D-Galactopyranosyl-4-hexacosanoyl-2-(3-(2-acetoxy-4,6-dimethylphenyl)-3,3-dimethylpropionoylamino) octadecane-1,3,4-triol (CN162)

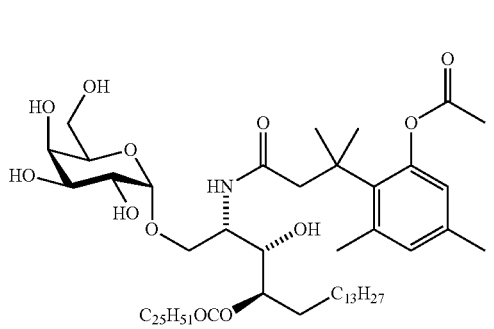

3-(2-Acetoxy-4,6-dimethylphenyl)-3,3-dimethylpropionic acid succinimidyl ester is dissolved in $CH_2Cl_2$ (2 mL) and added to a stirred solution of CN089 (18 mg, 0.021 mmol) in pyridine (2 mL) when triethylamine (2 mL) is added. After 18 h the solvents are removed in vacuo to give a crude residue that is purified by chromatography on silica gel eluting with $MeOH/CHCl_3$ (0:100 to 35:75) followed by further chromatography on C18 silica gel. Elution with $CHCl_3/MeOH$ (0:100 to 50:50) affords the title compound CN162 (16 mg, 0.014 mmol, 67%) as a white solid. $^1H$ NMR (500 MHz, $CDCl_3/CD_3OD$) δ 0.88 (t, J=6.7 Hz, 6H), 1.22-1.33 (m, 68H), 1.58-1.64 (m, 10H), 2.24 (s, 3H), 2.32-2.35 (m, 5H), 2.55 (s, 3H), 2.64 (s, 2H), 3.52 (t, J=6.0 Hz, 1H), 3.56-3.60 (m, 1H), 3.64-3.76 (m, 6H), 3.90-3.94 (m, 2H), 4.78 (d, J=4.0 Hz, 1H), 4.78-4.83 (m, 1H), 6.60 (bs, 1H), 6.84 (bs, 1H); $^{13}C$ NMR (126 MHz, $CDCl_3/CD_3OD$) δ 15.3, 21.3, 23.0, 24.0, 26.4, 26.6, 30.4, 30.5, 30.7, 30.9, 31.0, 32.8, 32.9, 33.3, 35.9, 40.9, 51.5, 63.2, 69.7, 70.5, 71.1, 71.7, 72.0, 73.4, 75.8, 101.5, 124.6, 134.0, 135.1, 137.9, 139.8, 151.1, 172.8, 173.2, 175.8; HRMS (ESI): m/z calcd for $C_{65}H_{117}NO_{12}Na$ $[M+Na]^+$ 1126.8473. found 1126.8461.

Example 15

Formulating Compounds of the Invention for Intravenous Injection

Compounds of the invention are formulated analogously to reported methods for α-GalCer. Briefly, solubilisation of α-GalCer is based on excipient proportions described by Giaccone et al (Giaccone, Punt et al. 2002). Thus, 100 µL of a 10 mg/mL solution of α-GalCer or a compound of the invention in 9:1 THF/MeOH is added to 1.78 mL of an aqueous solution of Tween 20 (15.9 mg), sucrose (177 mg) and L-histidine (23.8 mg). This homogenous mixture is freeze dried and the resulting foam is stored under Ar at −18° C. This material is reconstituted with 1.0 mL of PBS or water prior to serial dilutions in PBS to achieve final injectable solutions of α-GalCer or compounds of the invention.

Example 16

HPLC-ESI-MSMS Quantification of α-GalCer

Quantification of the amount of α-GalCer in various test samples of compounds of the invention is made by HPLC-ESI-MSMS analysis using a Waters 2795 HPLC and a Waters Q-TOF Premier™ Tandem Mass Spectrometer. The chromatography used a Phenomenex Kinetex C18 2.6 mm 3.0×50 mm column eluting with isocratic methanol containing 10 mM ammonium formate+0.5% formic acid at a flow rate of 0.2 mL/min. α-GalCer is monitored by selective reactant monitoring of 858.7 to 696.7 Da. The estimate of amount of α-GalCer is made by comparison of ion count integrals to a standard curve run on the same day or by comparison to test samples spiked with a known amount of α-GalCer.

The level of α-GalCer is determined on freshly reconstituted formulated samples unless otherwise stated. The estimated maximum level of α-GalCer for key compounds is given below.

| Compound | Max α-GalCer (ppm) | Max α-GalCer/injection |
|---|---|---|
| CN131 | 6,000 (analysis on non-formulated sample) | 1.2 ng |
| CN136 | 1,000 | 0.2 ng |
| CN141 | 270 | 0.054 ng |
| CN142 | 1,500 | 0.3 ng |
| CN145 | 40 | 0.008 ng |
| CN146 | 2,500 | 0.5 ng |
| CN147 | 615 | 0.123 ng |
| CN150 | 1,100 | 0.22 ng |
| CN151 | 610 | 0.12 ng |
| CN158 | 180 | 0.25 ng |
| CN158* | 170 | 0.24 ng |

*Unformulated sample (aqueous solution)

Example 17

Biological Studies

Mice.

C57BL/6 are from breeding pairs originally obtained from Jackson Laboratories, Bar Harbor, Me., and used according to institutional guidelines with approval from the Victoria University of Wellington Animal Ethics Committee.

Administration of Compounds of the Invention.

Each compound of the invention is supplied as formulated product (see example 12), and diluted in phosphate-buffered saline (PBS) for injection (200 ng/mouse) by intravenous injection into the lateral tail vein. In humans the expected therapeutic dose lies in the 50-4800 (µg/m$^2$) range (Giaccone, Punt et al. 2002). Note, 200 ng in a mouse is a human equivalent dose of 30 µg/m$^2$.

All antibody labeling is performed on ice in FACS buffer (PBS supplemented with 1% FCS, 0.05% sodium azide, and 2 mM EDTA). Non-specific FcR-mediated antibody staining is blocked by incubation for 10 min with anti-CD16/32 Ab (24G2, prepared in-house from hybridoma supernatant). Flow cytometry is performed on a BD Biosciences FACSCalibur or BD LSRII SORP flow cytometer with data analysis using FlowJo software (Tree Star, Inc., OR, USA).

Phenotyping DC from Spleen.

Antibody staining and flow cytometry are used to examine the expression of maturation markers on dendritic cells in the spleen following injection of compounds of the invention. Splenocyte preparations are prepared by gentle teasing of splenic tissue through gauze in Iscove's Modified Dulbecco's Medium with 2 mM glutamine, 1% penicillin-streptomycin, 5×10-5 M 2-mercapto-ethanol and 5% fetal bovine serum (all Invitrogen, Auckland, New Zealand), followed by lysis of red blood cells with RBC lysis buffer (Puregene, Gentra Systems, Minneapolis, Minn., USA). Antibody staining is performed in PBS 2% fetal bovine serum and 0.01% sodium azide. The anti-FcgRII monoclonal antibody 2.4G2 is used at 10 mg/ml to inhibit non-specific staining. Monoclonal antibodies (all BD Biosciences Pharmingen, San Jose, Calif., USA) are used to examine expression of the maturation markers CD40, CD80 and CD86 on CD11c+ dendritic cells.

Analysis of Cytokine Release into Serum.

Blood is collected from the lateral tail vein at different time intervals after glycolipid administration. Serum is collected after blood has clotted, and levels of cytokines IL-12p70, IL-4 and IFN-g are assessed by cytokine bead array technology (Bioplex, Biorad), according to the manufacturer's instructions.

Analysis of Peptide-Specific T Cell Proliferation In Vivo.

Pooled lymph node cell suspensions are prepared from animals of a cross between OT-I mice, which express a transgenic T cell receptor (TCR) specific for the ovalbumin epitope SIINFEKL in the context of H-2K$^b$ molecules, and B6.SJL-Ptprc$^a$ Pepc$^b$/BoyJ mice, which are congenic with C57BL/6 mice for the CD45.1$^+$ marker. The samples are enriched for CD8$^+$ cells using antibody coated magnetic beads (Miltenyi), and then transferred into C57BL/6 mice ($1\times10^4$ per mouse). Groups of recipient animals (n=5) are immunized with compounds of the invention one day later. Doses are chosen to provide equivalent molar values of SIINFEKL peptide. Control animals receive phosphate-buffered saline. After seven days, blood samples are collected from the lateral tail vein and stained directly ex vivo with antibodies for TCR Vα2, CD45.1 and CD8 to detect the SIINFEKL-specific CD8$^+$ T cells by flow cytometry.

Analysis of Anti-Tumour Activity.

Groups of C57BL/6 mice (n=5) receive a subcutaneous injection into the flank of $1\times10^5$ B16.OVA melanoma cells, which express a cDNA encoding the chicken ovalbumin (OVA) sequence. The different groups are treated 7 days later, when tumours are fully engrafted, by intravenous injection of one of the following; 200 μg OVA protein together with 200 ng α-GalCer, 200 μg OVA protein together with 200 ng of a compound of the invention, or PBS. Mice are monitored for tumour growth every 3-4 days, and tumour size for each group is calculated as the mean of the products of bisecting diameters (±SEM). Measurements are terminated for each group when the first animal develops a tumour exceeding 200 mm$^2$.

Analysis of Reactivity of Human NKT Cells to Compounds of the Invention.

Peripheral blood is drawn into heparinized tubes, diluted 1:1 in PBS, and layered over a sodium diatrizoate and polysaccharide solution (Lymphoprep; Axis-Shield, Oslo, Norway) before centrifugation at 800×g for 25 minutes at room temperature to collect the peripheral blood mononuclear cell (PBMC) fraction, which contains NKT cells. To assess proliferation of NKT cells, PBMC ($2\times10^5$ per well) are cultured at 37° C. in Iscove's Modified Dulbecco's Medium with 5% human AB serum and the indicated concentrations of α-GalCer, or the compounds of the invention, with recombinant human IL-2 50 U/mL (Chiron Corporation, Emeryville, Calif.) added after 24 hours. After 7 days of culture, the cells are analysed by flow cytometry, using fluorescent soluble CD1d tetramers that have been loaded with α-GalCer to identify the NKT cells. Data are presented as percentage of NKT cells (CD1d/α-GalCer tetramer-binding cells) of total T cells (identified by binding of antibody specific for CD3) in the final cultures.

Where, in the foregoing description, reference has been made to integers having known equivalents thereof, those equivalents are herein incorporated as if individually set forth.

Although the invention has been described in connection with specific preferred embodiments, it should be understood that the invention as claimed should not be unduly limited to such specific embodiments.

It is appreciated that further modifications may be made to the invention as described herein without departing from the spirit and scope of the invention.

INDUSTRIAL APPLICABILITY

The invention relates to sphingoglycolipid analogues, precursors and prodrugs of these compounds, which are useful in treating or preventing diseases or such as those relating to infection, atopic disorders, autoimmune diseases or cancer.

REFERENCES

Alexander, J., D. S. Bindra, et al. (1996). "Investigation of (Oxodioxolenyl)methyl carbamates as nonchiral bioreversible prodrug moieties for chiral amines." *J Med Chem* 39(2): 480-486.

Alexander, J., R. Cargill, et al. (1988). "(Acyloxy)alkyl carbamates as novel bioreversible prodrugs for amines: increased permeation through biological membranes." *J Med Chem* 31(2): 318-322.

Amsberry, K. L. and R. T. Borchardt (1991). "Amine prodrugs which utilize hydroxy amide lactonization. I. A potential redox-sensitive amide prodrug." *Pharm Res* 8(3): 323-330.

Amsberry, K. L., A. E. Gerstenberger, et al. (1991). "Amine prodrugs which utilize hydroxy amide lactonization. II. A potential esterase-sensitive amide prodrug." *Pharm Res* 8(4): 455-461.

Atwell, G. J., B. M. Sykes, et al. (1994). "Relationships between structure and kinetics of cyclization of 2-aminoaryl amides: potential prodrugs of cyclization-activated aromatic mustards." *J Med Chem* 37(3): 371-380.

Baadsgaard, H. and W. D. Treadwell (1955). "Zur Kenntnis der komplexen Wolframcyanide K4[W(CN)8], 2H2O and K3[W(CN)8], H2O." *Helvetica Chimica Acta* 38(7): 1669-1679.

Badovinac, V. P., Porter, B. B., et al. (2004). "CD8+ T cell contraction is controlled by early inflammation." *Nature Immunology* 5(8): 809-817.

Baek, D. J., J.-H. Seo, et al. (2011). "The 3-Deoxy Analogue of α-GalCer: Disclosing the Role of the 4-Hydroxyl Group for CD1d-Mediated NKT Cell Activation." *ACS Medicinal Chemistry Letters* 2(7): 544-548.

Banchet-Cadeddu, A., E. Henon, et al. (2011). "The stimulating adventure of KRN 7000." *Org Biomol Chem* 9(9): 3080-3104.

Bendelac, A., P. B. Savage, et al. (2007). "The biology of NKT cells." *Annu Rev Immunol* 25: 297-336.

Bhat, A. S. and J. Gervay-Hague (2001). "Efficient syntheses of beta-cyanosugars using glycosyl iodides derived from per-O-silylated mono- and disaccharides." *Org Lett* 3(13): 2081-2084.

Brossart, P., K. S. Heinrich, et al. (1999). "Identification of HLA-A2-restricted T-cell epitopes derived from the MUC1 tumor antigen for broadly applicable vaccine therapies." *Blood* 93(12): 4309-4317.

Butler, R. N., C. B. O'Regan, et al. (1978). "Reactions of fatty acids with amines. Part 2. Sequential thermal reactions of stearic (octadecanoic) acid with some 1,2- and 1,3-aminoalcohols and bis-amines." *Journal of the Chemical Society, Perkin Transactions* 1(4): 373-377.

Carpino, L. A., S. A. Triolo, et al. (1989). "Reductive lactonization of strategically methylated quinone propionic acid esters and amides." *The Journal of Organic Chemistry* 54(14): 3303-3310.

Chen, G., J. Schmieg, et al. (2004). "Efficient synthesis of alpha-C-galactosyl ceramide immunostimulants: use of ethylene-promoted olefin cross-metathesis." *Org Lett* 6(22): 4077-4080.

Cheng, J. M. H., S. H. Chee, et al. (2011). "An improved synthesis of dansylated α-galactosylceramide and its use as a fluorescent probe for the monitoring of glycolipid uptake by cells." *Carbohydrate Research* 346(7): 914-926.

Davidson, E. J., R. L. Faulkner, et al. (2004). "Effect of TA-CIN (HPV 16 L2E6E7) booster immunisation in vulval intraepithelial neoplasia patients previously vaccinated with TA-HPV (vaccinia virus encoding HPV 16/18 E6E7)." *Vaccine* 22(21-22): 2722-2729.

Deng, S., J. Mattner, et al. (2011). "Impact of sugar stereochemistry on natural killer T cell stimulation by bacterial glycolipids." *Org Biomol Chem* 9(22): 7659-7662.

Dere, R. T. and X. Zhu (2008). "The first synthesis of a thioglycoside analogue of the immunostimulant KRN7000." *Org Lett* 10(20): 4641-4644.

Drefahl, G. and H.-H. Hörhold (1961). "Aminoalkohole, XV. Stereoselektive Darstellung and konfigurative Zuordnung der diastereomeren DL-3-Amino-1.2-diphenyl-propanole-(1) (zum Mechanismus der Ringschlußreaktion von Aminoalkoholen mit Benzimidsäureester)." *Chemische Berichte* 94(6): 1641-1656.

Du, W., S. S. Kulkarni, et al. (2007). "Efficient, one-pot syntheses of biologically active alpha-linked glycolipids." *Chem Commun (Camb)*(23): 2336-2338.

Ebensen, T., C. Link, et al. (2007). "A pegylated derivative of alpha-galactosylceramide exhibits improved biological properties." *J Immunol* 179(4): 2065-2073.

Fujii, S., K. Shimizu, et al. (2002). "Prolonged IFN-gamma-producing NKT response induced with alpha-galactosylceramide-loaded DCs." *Nat Immunol* 3(9): 867-874.

Fujii, S., K. Shimizu, et al. (2003). "Activation of natural killer T cells by alpha-galactosylceramide rapidly induces the full maturation of dendritic cells in vivo and thereby acts as an adjuvant for combined CD4 and CD8 T cell immunity to a coadministered protein." *J Exp Med* 198(2): 267-279.

Gangwar, S., G. M. Pauletti, et al. (1997). "Synthesis of a Novel Esterase-Sensitive Cyclic Prodrug of a Hexapeptide Using an (Acyloxy)alkoxy Promoiety." *The Journal of Organic Chemistry* 62(5): 1356-1362.

Giaccone, G., C. J. Punt, et al. (2002). "A phase I study of the natural killer T-cell ligand alpha-galactosylceramide (KRN7000) in patients with solid tumors." *Clin Cancer Res* 8(12): 3702-3709.

Greenwald, R. B., Y. H. Choe, et al. (2000). "Drug delivery systems based on trimethyl lock lactonization: poly(ethylene glycol) prodrugs of amino-containing compounds." *J Med Chem* 43(3): 475-487.

Greenwald, R. B., A. Pendri, et al. (1999). "Drug delivery systems employing 1,4- or 1,6-elimination: poly(ethylene glycol) prodrugs of amine-containing compounds." *J Med Chem* 42(18): 3657-3667.

Gryko, D. T., C. Clausen, et al. (1999). "Thiol-Derivatized Porphyrins for Attachment to Electroactive Surfaces." The *Journal of Organic Chemistry* 64(23): 8635-8647.

Hermans, I. F., J. D. Silk, et al. (2003). "NKT cells enhance CD4+ and CD8+ T cell responses to soluble antigen in vivo through direct interaction with dendritic cells." *J Immunol* 171(10): 5140-5147.

Hillery, P. S. and L. A. Cohen (1983). "Stereopopulation control. 9. Rate and equilibrium enhancement in the lactonization of (o-hydroxyphenyl)acetic acids." The *Journal of Organic Chemistry* 48(20): 3465-3471.

Hong, S., M. T. Wilson, et al. (2001). "The natural killer T-cell ligand alpha-galactosylceramide prevents autoimmune diabetes in non-obese diabetic mice." *Nat Med* 7(9): 1052-1056.

Howell, A. R., R. C. So, et al. (2004). "Approaches to the preparation of sphinganines." *Tetrahedron* 60(50): 11327-11347.

Iha, R. K., B. A. van Horn, et al. (2010). "Complex, degradable polyester materials via ketoxime ether-based functionalization: Amphiphilic, multifunctional graft copolymers and their resulting solution-state aggregates." *Journal of Polymer Science Part A: Polymer Chemistry* 48(16): 3553-3563.

Ingram, L. J. and S. D. Taylor (2006). "Introduction of 2,2,2-trichloroethyl-protected sulfates into monosaccharides with a sulfuryl imidazolium salt and application to the synthesis of sulfated carbohydrates." *Angew Chem Int Ed Engl* 45(21): 3503-3506.

Johansen, S. K., H. T. Kornø, et al. (1999). "Synthesis of Carbasugars from Aldonolactones: Ritter-Type Epoxide Opening in the Synthesis of Polyhydroxylated Aminocyclopentanes." *Synthesis* 1999(01): 171,177.

Karbach, J., S. Gnjatic, et al. (2010). "Tumor-reactive CD8+ T-cell responses after vaccination with NY-ESO-1 peptide, CpG 7909 and Montanide ISA-51: association with survival." *Int J Cancer* 126(4): 909-918.

Kawano, T., J. Cui, et al. (1997). "CD1d-restricted and TCR-mediated activation of valpha14 NKT cells by glycosylceramides." *Science* 278(5343): 1626-1629.

Kinjo, Y., P. Illarionov, et al. (2011). "Invariant natural killer T cells recognize glycolipids from pathogenic Gram-positive bacteria." *Nature Immunology*: 1-10.

Lee, A., K. J. Farrand, et al. (2006). "Novel synthesis of alpha-galactosyl-ceramides and confirmation of their powerful NKT cell agonist activity." *Carbohydr Res* 341(17): 2785-2798.

Levy, A., J. Pitcovski, et al. (2007). "A melanoma multi-epitope polypeptide induces specific CD8+ T-cell response." *Cell Immunol* 250(1-2): 24-30.

Li, J., X. Luo, et al. (1998). "Synthesis and biological evaluation of a water soluble phosphate prodrug of 3-aminopyridine-2-carboxaldehyde thiosemicarbazone (3-AP)." *Bioorg Med Chem Lett* 8(22): 3159-3164.

Li, Y., E. Girardi, et al. (2010). "The Vα14 invariant natural killer T cell TCR forces microbial glycolipids and CD1d into a conserved binding mode." *Journal of Experimental Medicine* 207(11): 2383-2393.

Li, Z., Y. Oka, et al. (2008). "Identification of a WT1 protein-derived peptide, WT1, as a HLA-A 0206-restricted, WT1-specific CTL epitope." *Microbiol Immunol* 52(11): 551-558.

Liao, Y. and B. Wang (1999). "Substituted coumarins as esterase-sensitive prodrug moieties with improved release rates." *Bioorg Med Chem Lett* 9(13): 1795-1800.

Lin, S. M., Brian; Porter, Kenneth T.; Rossman, Craig A.; Zennie, Thomas; Wemple, James. (2000). "A Continuous Procedure for Preparation of para Functionalized Aromatic Thiols Using Newman-Kwart Chemistry." *Organic Preparations and Procedures International* 32(6): 13.

Lin, Y.-I., P. Bitha, et al. (1997). "Mono and bis double ester prodrugs of novel aminomethyl-THF 1β-methylcarbapenems." *Bioorganic & Medicinal Chemistry Letters* 7(14): 1811-1816.

Lu, X.-L., Z.-H. Liang, et al. (2006). "Induction of the Epstein-Barr Virus Latent Membrane Protein 2 Antigen-specific Cytotoxic T Lymphocytes Using Human Leukocyte Antigen Tetramer-based Artificial Antigen-presenting Cells." *Acta Biochimica et Biophysica Sinica* 38(3): 157-163.

Lu, X., L. Song, et al. (2006). "Synthesis and evaluation of an alpha-C-galactosylceramide analogue that induces Th1-biased responses in human natural killer T cells." *Chembiochem* 7(11): 1750-1756.

Luo, S.-Y., S. S. Kulkarni, et al. (2006). "A Concise Synthesis of Tetrahydroxy-LCB, α-Galactosyl Ceramide, and 1,4-Dideoxy-1,4-imino-l-ribitol via d-Allosamines as Key Building Blocks." *The Journal of Organic Chemistry* 71(3): 1226-1229.

Matto, P., E. Modica, et al. (2007). "A general and stereoselective route to alpha- or beta-galactosphingolipids via a common four-carbon building block." *J Org Chem* 72(20): 7757-7760.

Morita, M., K. Motoki, et al. (1995). "Structure-activity relationship of alpha-galactosylceramides against B16-bearing mice." *J Med Chem* 38(12): 2176-2187.

Motoki, K., M. Morita, et al. (1995). "Immunostimulatory and antitumor activities of monoglycosylceramides having various sugar moieties." *Biol Pharm Bull* 18(11): 1487-1491.

Murata, K., T. Toba, et al. (2005). "Total synthesis of an immunosuppressive glycolipid, (2S,3S,4R)-1-O-(alpha-d-galactosyl)-2-tetracosanoylamino-1,3,4-nonanetriol." *J Org Chem* 70(6): 2398-2401.

Nicolaou, M. G., C.-S. Yuan, et al. (1996). "Phosphate Prodrugs for Amines Utilizing a Fast Intramolecular Hydroxy Amide Lactonization." *The Journal of Organic Chemistry* 61(24): 8636-8641.

O'Reilly, C. and P. V. Murphy (2011). "Synthesis of alpha-S-glycosphingolipids based on uronic acids." *Org Lett* 13(19): 5168-5171.

Parekh, V. V., M. T. Wilson, et al. (2005). "Glycolipid antigen induces long-term natural killer T cell anergy in mice." *J Clin Invest* 115(9): 2572-2583.

Park, J. J., J. H. Lee, et al. (2008). "Synthesis of all stereoisomers of KRN7000, the CD1d-binding NKT cell ligand." *Bioorg Med Chem Lett* 18(14): 3906-3909.

Plettenburg, O., V. Bodmer-Narkevitch, et al. (2002). "Synthesis of alpha-galactosyl ceramide, a potent immunostimulatory agent." *J Org Chem* 67(13): 4559-4564.

Pu, J. and R. W. Franck (2008). "C-Galactosylceramide Diastereomers via Sharpless Asymmetric Epoxidation Chemistry." *Tetrahedron* 64(37): 8618-8629.

Raju, R., B. F. Castillo, et al. (2009). "Synthesis and evaluation of 3″- and 4″-deoxy and -fluoro analogs of the immunostimulatory glycolipid, KRN7000." *Bioorg Med Chem Lett* 19(15): 4122-4125.

Sakurai, K. and D. Kahne (2010). "Design and Synthesis of Functionalized Trisaccharides as p53-Peptide Mimics." *Tetrahedron Lett* 51(29): 3724-3727.

Schneider, G., L. Hackler, et al. (1985). "Ritter-reaction on steroids: Ring expansion of steroid oxethans into dihydrooxazines." *Tetrahedron* 41(16): 3377-3386.

Secrist, J. A. and M. W. Logue (1972). "Amine hydrochlorides by reduction in the presence of chloroform." *The Journal of Organic Chemistry* 37(2): 335-336.

Silk, J. D., I. F. Hermans, et al. (2004). "Utilizing the adjuvant properties of CD1d-dependent NK T cells in T cell-mediated immunotherapy." *J Clin Invest* 114(12): 1800-1811.

Sullivan, B. A., N. A. Nagarajan, et al. (2010). "Mechanisms for glycolipid antigen-driven cytokine polarization by Valpha14i NKT cells." *J Immunol* 184(1): 141-153.

Sun, C.-Q., P. T. W. Cheng, et al. (2002). "A general synthesis of dioxolenone prodrug moieties." *Tetrahedron Lett* 43(7): 1161-1164.

Tashiro, T., N. Hongo, et al. (2008). "RCAI-17, 22, 24-26, 29, 31, 34-36, 38-40, and 88, the analogs of KRN7000 with a sulfonamide linkage: their synthesis and bioactivity for mouse natural killer T cells to produce Th2-biased cytokines." *Bioorg Med Chem* 16(19): 8896-8906.

Tashiro, T., R. Nakagawa, et al. (2008). "RCAI-61, the 6′-O-methylated analog of KRN7000: its synthesis and potent bioactivity for mouse lymphocytes to produce interferon-γ in vivo." *Tetrahedron Lett* 49(48): 6827-6830.

Taylor, S. D. and A. Desoky (2011). "Rapid and efficient chemoselective and multiple sulfations of phenols using sulfuryl imidazolium salts." *Tetrahedron Lett* 52(26): 3353-3357.

Trappeniers, M., S. Goormans, et al. (2008). "Synthesis and in vitro evaluation of alpha-GalCer epimers." *ChemMedChem* 3(7): 1061-1070.

Tupin, E., A. Nicoletti, et al. (2004). "CD1d-dependent activation of NKT cells aggravates atherosclerosis." *J Exp Med* 199(3): 417-422.

Turner, W. W., R. N. Booher, et al. (1977). "Synthesis of two metabolites of (+)-propoxyphene." *Journal of Medicinal Chemistry* 20(8): 1065-1068.

Uchimura, A., T. Shimizu, et al. (1997). "Immunostimulatory activities of monoglycosylated α-d-pyranosylceramides." *Bioorganic & Medicinal Chemistry* 5(12): 2245-2249.

Veerapen, N., M. Brigl, et al. (2009). "Synthesis and biological activity of alpha-galactosyl ceramide KRN7000 and galactosyl (alpha1→2) galactosyl ceramide." *Bioorg Med Chem Lett* 19(15): 4288-4291.

Wingender, G., P. Rogers, et al. (2011). "Invariant NKT cells are required for airway inflammation induced by environmental antigens." *J Exp Med* 208(6): 1151-1162.

Wipf, P. and J. G. Pierce (2006). "Expedient synthesis of the alpha-C-glycoside analogue of the immunostimulant galactosylceramide (KRN7000)." *Org Lett* 8(15): 3375-3378.

Wu, T.-N., K.-H. Lin, et al. (2011). "Avidity of CD1d-ligand-receptor ternary complex contributes to T-helper 1 (Th1) polarization and anticancer efficacy." *Proc Natl Acad Sci USA* 108(42): 17275-17280.

Zeng, D., Y. Liu, et al. (2003). "Activation of natural killer T cells in NZB/W mice induces Th1-type immune responses exacerbating lupus." *J Clin Invest* 112(8): 1211-1222.

Zhang, Z., W. Zhao, et al. (2011). "The total synthesis of immunostimulant alpha-galactosylceramides from naturally configured alpha-galactoside raffinose." *Org Lett* 13(17): 4530-4533.

The invention claimed is:
1. A compound of formula (I):

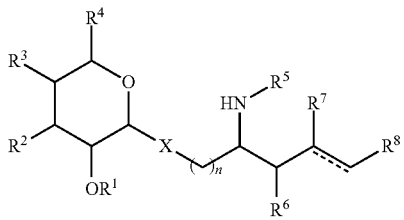
(I)

wherein:
R' is H or glycosyl, provided that if R' is glycosyl then $R^2$ and $R^3$ are both OH and $R^4$ is $CH_2OH$;
$R^2$ is selected from the group consisting of H, OH, F and $OR^{10}$, provided that if $R^2$ is H, F or $OR^{10}$, then $R^1$ is H, $R^3$ is OH and $R^4$ is $CH_2OH$;
$R^3$ is selected from the group consisting of H, OH, F and $OR^{10}$; provided that if $R^3$ is H, F or $OR^{10}$, then $R^1$ is H, $R^2$ is OH and $R^4$ is $CH_2OH$;
$R^4$ is $CH_3$, $CH_2OH$, $CH_2OCOR^{11}$, $CH_2OR^{10}$, $CH_2OR^{11}$, $CH_2OSO_3H$, $CH_2SH$, $CH_2SR^{11}$, $CH_2SOR^{11}$, $CH_2SO_2R^{11}$, $CH_2PO_3H_2$, $CH_2OP(O)(OH)_2$, $CH_2OP(O)(OH)(OH^{11})$, $CH_2OP(O)(OR^{11})_2$, $CO_2H$, $CH_2NHCOR^{11}$, $CH_2NHCO_2R^{11}$, $CH_2NHCONH_2$, $CH_2NHCONHR^{11}$, $CH_2NHCON(R^{11})_2$, $CH_2N(R^{11})_2$, $CH_2NHSO_2R^{11}$; provided that if $R^4$ is other than $CH_2OH$, then $R^1$ is H and $R^2$ and $R^3$ are OH;
$R^5$ is H;
or $R^5$ is a radical of formula (i):

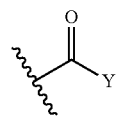
(i)

wherein Y is a radical of formula:

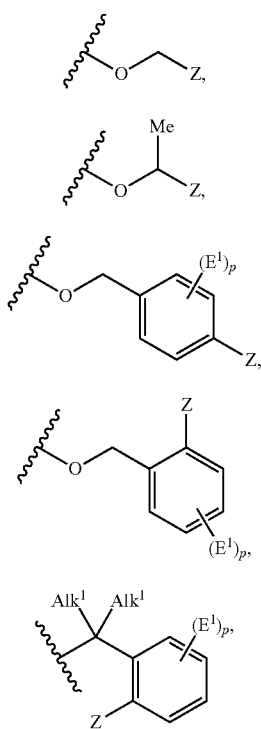

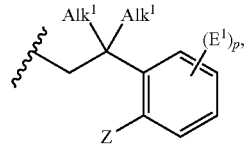
(f)

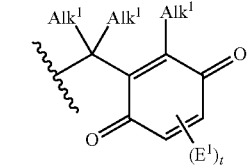
(g)

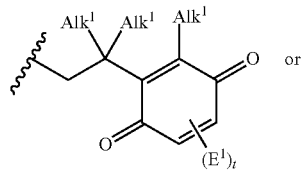
(h)

or

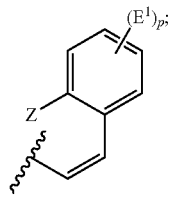
(j)

each $E^1$, the same or different, is independently selected from the group consisting of H, alkyl, alkoxy, halogen, nitroaryl; or, together with the ring to which it is attached, forms a fused bicyclic aryl group;
p is an integer from 1 to 4;
t is an integer from 1 to 2;
$Alk^1$ is $C_1$-$C_4$ straight chain alkyl;
wherein when Y is a radical of formula (a) or (b) then Z is:

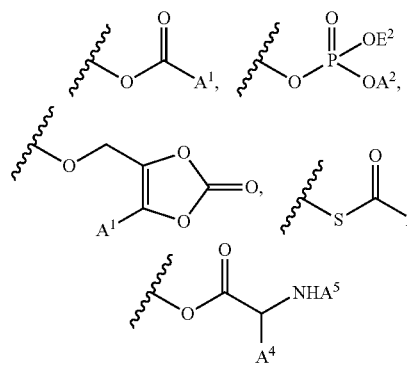

or wherein when Y is a radical of formula (c), (d), (e), (f) or (j) then Z is:

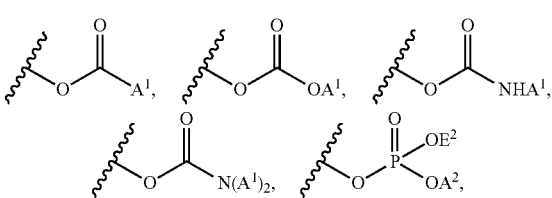

-continued

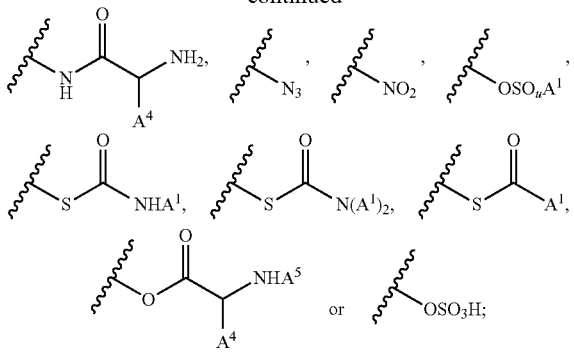

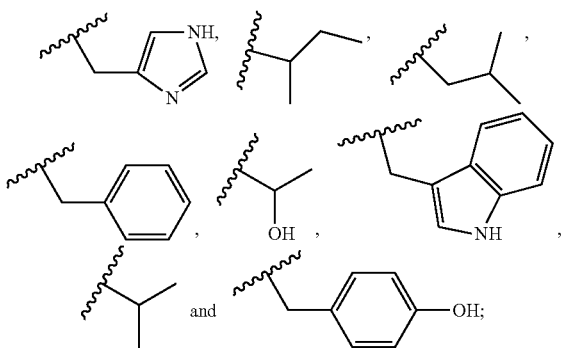

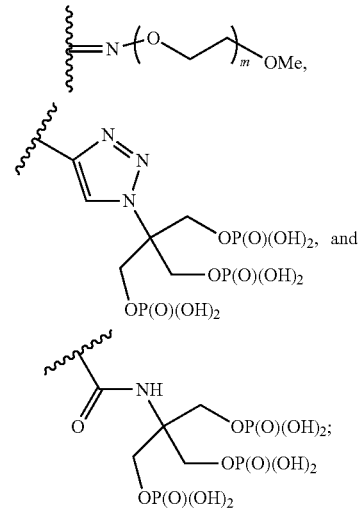

u is 1 or 2;

each $A^1$, the same or different, is independently selected from the group consisting of:

alkyl which may be optionally substituted with one or more substituents selected from the group consisting of $(OCH_2CH_2)_mOMe$, $NHC(O)OR^{14}$, alkoxyimino, oxo, halogen, alkoxy, $NHCOCH_2(OCH_2CH_2)_mOMe$, alkenyl which may be optionally substituted with one or more substituents selected from the group consisting of $(OCH_2CH_2)_mOMe$, alkoxyimino, oxo, halogen and alkoxy;

aryl which may be optionally substituted with one or more substituents selected from the group consisting of $(OCH_2CH_2)_mOMe$, alkyl, alkoxy, dialkylamino, nitro, halogen; or aralkyl which may be optionally substituted with one or more substituents selected from the group consisting of $(OCH_2CH_2)_mOMe$, alkoxyimino, oxo, halogen, alkyl, alkoxy, dialkylamino and nitro;

m is an integer from 10 to 1500;

$E^2$ and $A^2$ are each independently selected from H and $A^1$;

$A^4$ is selected from the group consisting of H, methyl, $CH_2CH_2CH_2NHC(=NH)NH_2$, $CH_2C(=O)NH_2$, $CH_2C(=O)OH$, $CH_2SH$, $CH_2CH_2C(=O)OH$, $CH_2CH_2C(=O)NH_2$, $CH_2(CH_2)_3NH_2$, $CH_2CH_2SCH_3$, $CH_2OH$, or $A^4$, together with the carbon to which it is attached and the nitrogen adjacent to that carbon, forms a pyrrolidine ring;

$A^5$ is H or benzyloxycarbonyl;

$R^6$ is $OR^{12}$, OH or H;

$R^7$ is $OR^{12}$, OH or H; provided that at least one of $R^6$ and $R^7$ is $OR^{12}$; wherein when $R^6$ is $OR^{12}$, $R^7$ is H, $R^8$ is $C_1$-$C_{15}$ alkyl and X is O, then ---------- denotes an optional double bond linking the carbon adjacent to $R^7$ with the carbon adjacent to $R^8$;

$R^8$ is H or $C_1$-$C_{15}$ alkyl having a straight or branched carbon chain, wherein the carbon chain optionally incorporates one or more double bonds, one or more triple bonds, one or more oxygen atoms and/or a terminal or non-terminal optionally substituted aryl group;

$R^{10}$ is glycosyl;

$R^{11}$ is lower alkyl, lower alkenyl or aralkyl;

$R^{12}$ is $C_6$-$C_{30}$ acyl having a straight or branched carbon chain optionally substituted with one or more hydroxy groups at positions 2 and/or 3 of the acyl group and/or an optionally substituted chain terminating aryl group and which optionally incorporates one or more double bonds, one or more triple bonds, and/or one or more optionally substituted arylene groups and wherein the carbon chain is optionally substituted with one or more deuterium atoms; wherein the optional substituents on the aryl and arylene groups may be selected from halogen, cyano, dialkylamino, $C_1$-$C_6$ amide, nitro, $C_1$-$C_6$ alkoxy, $C_1$-$C_6$ acyloxy and $C_1$-$C_6$ thioalkyl;

$R^{14}$ is an optionally substituted alkyl, aryl or aralkyl group;

X is O, $CH_2$ or S;

n is 1 when X is O or S; or n is 0 or 1 when X is $CH_2$;

wherein when X is $CH_2$ then the following must all be true: the stereochemistry of the 6-membered sugar ring in formula (I) is α-D-galacto; $R^1$ is H; $R^2$ and $R^3$ are both OH; $R^4$ is $CH_2OH$, $CH_2OR^{10}$ or $CH_2OR^{11}$; and:

$R^6$ is OH and $R^7$ is $OR^{12}$ and the stereochemistry at carbon atoms 2, 3 and 4 is (2S, 3S, 4R), (2S, 3S, 4S), (2R, 3S, 4S), (2R, 3S, 4R) or (2S, 3R, 4S); or $R^6$ is $OR^{12}$ and $R^7$ is H, and $R^8$ is $C_{13}H_{27}$ and the stereochemistry at carbon atoms 2 and 3 is (2S, 3S);

wherein when X is S then the following must all be true: the stereochemistry of the 6-membered sugar ring in formula (I) is α-D-galacto; $R^1$ is H; $R^2$ and $R^3$ are both OH; $R^4$ is $CH_2OH$, $CH_2OR^{10}$, $CH_2OR^{11}$ or $CO_2H$; and:

$R^6$ is OH and $R^7$ is $OR^{12}$ and the stereochemistry at carbon atoms 2, 3 and 4 is (2S, 3S, 4R); or $R^6$ is $OR^{12}$ and $R^7$ is H and the stereochemistry at the carbon atoms 2 and 3 is (2S, 3S);

or a pharmaceutically acceptable salt thereof.

2. A compound as claimed in claim 1 which is a compound of formula (Ia):

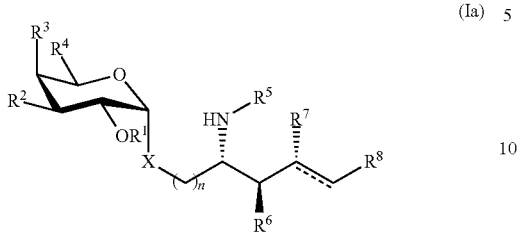

wherein X, $R^1$, $R^2$, $R^3$, $R^4$, $R^5$, $R^6$, $R^7$, $R^8$, $R^{10}$, $R^{11}$, $R^{12}$, $R^{14}$, $R^{15}$, $R^{16}$, Y, Z, $A^1$, $A^2$, $A^4$, $A^5$, $E^1$, $E^2$, $Alk^1$, p, t, m, u and n are all as defined in claim 1.

3. A compound as claimed in claim 1 wherein the stereochemistry of the 6-membered sugar ring of formula (I) is α-D-galacto.

4. A compound as claimed in claim 1 wherein X is O.

5. A compound as claimed in claim 1 wherein n in formula (I) is 1, the stereochemistry of the 6-membered sugar ring of formula (I) is α-D-galacto, $R^6$ is OH, $R^7$ is $OR^{12}$ and the stereochemistry at carbon atoms 2, 3 and 4 is (2S, 3S, 4R).

6. A compound as claimed in claim 1 wherein n in formula (I) is 0, the stereochemistry of the 6-membered sugar ring of formula (I) is α-D-galacto, $R^6$ is OH, $R^7$ is $OR^{12}$ and the stereochemistry at carbon atoms 2, 3 and 4 is (2S, 3S, 4R).

7. A compound as claimed in claim 1 wherein X is O, $R^6$ is $OR^{12}$, $R^7$ is H, $R^8$ is $C_1$-$C_{15}$ alkyl and ------- is a double bond linking the carbon adjacent to $R^7$ with the carbon adjacent to $R^8$, and the stereochemistry at carbon atoms 2, 3 is (2S, 3S).

8. A compound as claimed in claim 1 wherein $R^1$ is H.

9. A compound as claimed in claim 1 wherein $R^2$ is OH.

10. A compound as claimed in claim 1 wherein $R^3$ is OH.

11. A compound as claimed in claim 1 wherein $R^4$ is $CH_2OH$.

12. A compound as claimed in claim 1 wherein $R^5$ is a radical of formula (i):

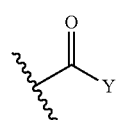

in Y is a radical of formula:

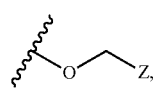

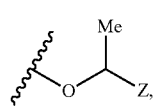

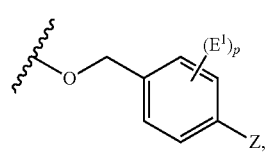

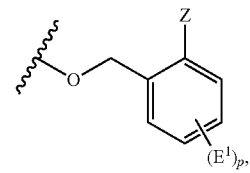

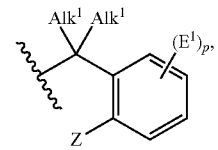

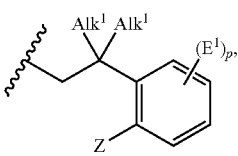

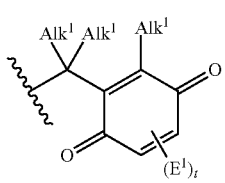

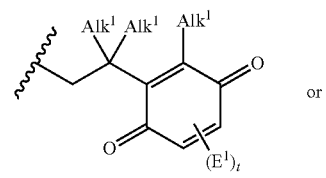

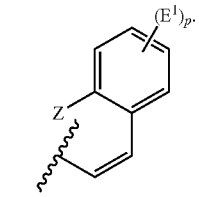

13. A compound as claimed in claim 1 wherein $R^6$ is OH.

14. A compound as claimed in claim 1 wherein $R^7$ is $OR^{12}$.

15. A compound as claimed in claim 1 wherein $R^8$ is $C_1$-$C_{15}$ alkyl having a straight or branched carbon chain, wherein the carbon chain optionally incorporates one or more double bonds, one or more triple bonds, one or more oxygen atoms and/or a terminal or non-terminal optionally substituted aryl group.

16. A compound as claimed in claim 1, selected from the group consisting of:

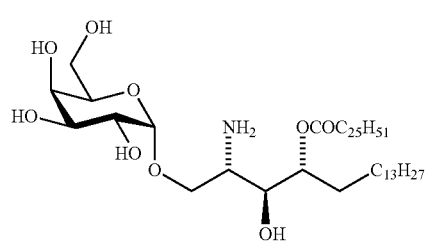

-continued
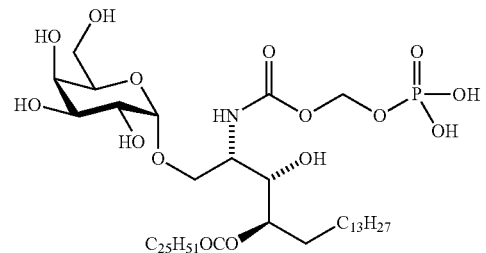
(b)
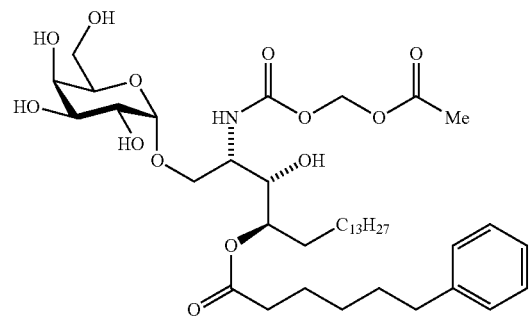
(c)
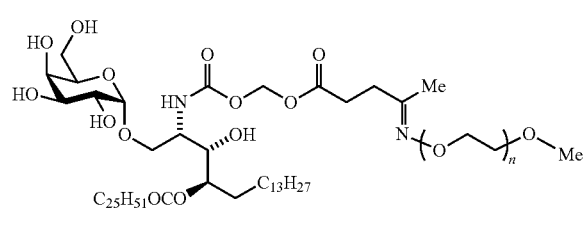
n = ~10-15,
(d)
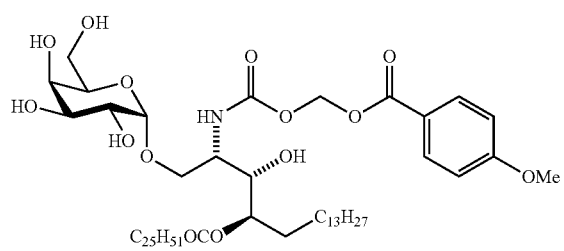
(e)
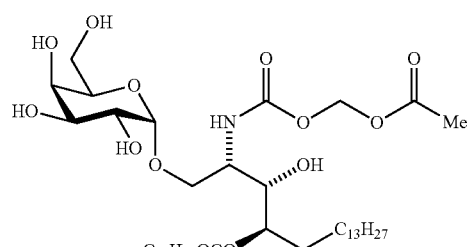
(f)
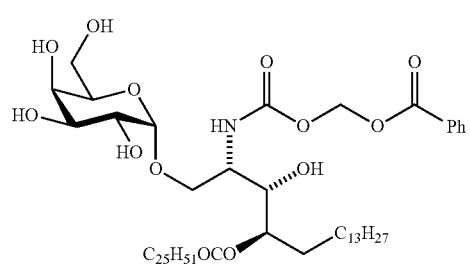
(g)
-continued
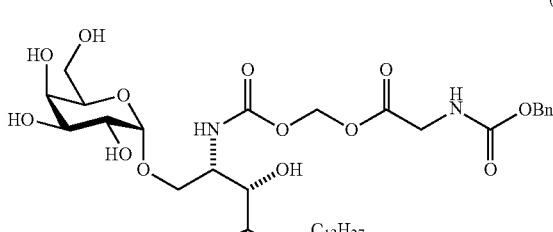
(h)
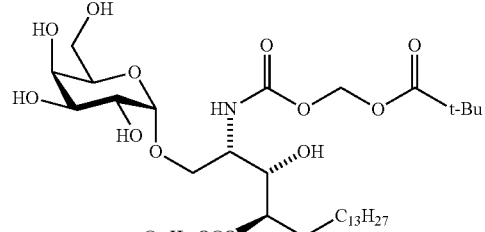
(j)
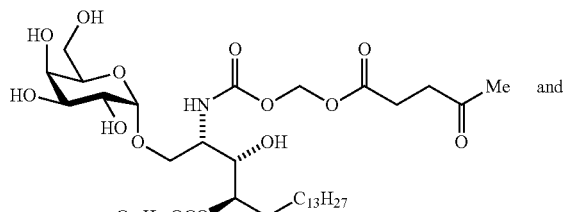
(k)
and
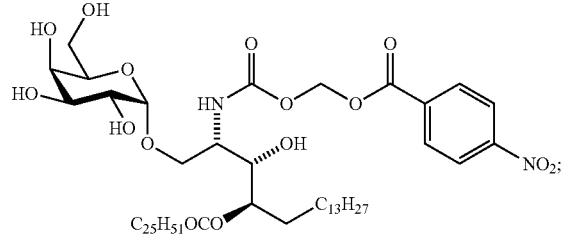
(m)
;
or a pharmaceutically acceptable salt thereof.
17. A compound as claimed in claim 1, selected from the group consisting of:
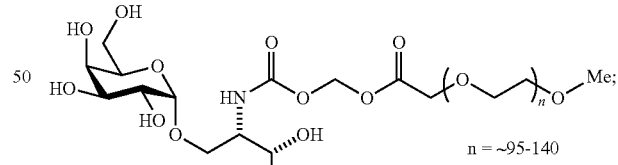
n = ~95-140
(n)
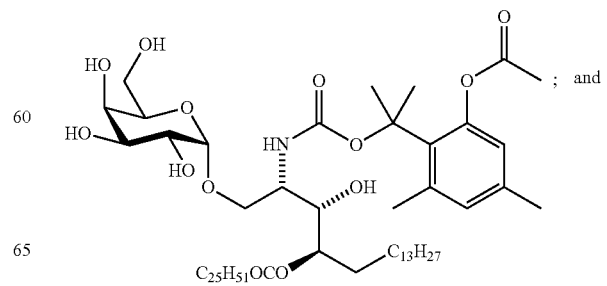
; and
(o)

-continued

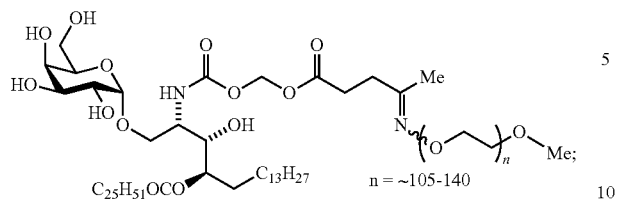
(p)

or a pharmaceutically acceptable salt thereof.

18. A pharmaceutical composition comprising a compound as claimed in claim 1 and optionally a pharmaceutically acceptable carrier.

19. An immunogenic composition comprising a compound as claimed in claim 1, an antigen and a pharmaceutically acceptable diluent.

20. A vaccine comprising a compound as claimed in claim 1 an antigen and a pharmaceutically acceptable diluent.

* * * * *